(12) United States Patent
Huff et al.

(10) Patent No.: US 11,633,738 B2
(45) Date of Patent: Apr. 25, 2023

(54) DEVICES AND METHODS FOR SAMPLE ANALYSIS

(71) Applicant: ABBOTT LABORATORIES, Abbott Park, IL (US)

(72) Inventors: Jeffrey B. Huff, Lincolnshire, IL (US); Mark A. Hayden, Ingleside, IL (US); Peter J. Karabatsos, Glencoe, IL (US); Andrew Fischer, Euless, TX (US); John M. Robinson, Gurnee, IL (US); Shelley R. Holets-McCormack, Waukegan, IL (US); Sophie Laurenson, Basel-Land (CH)

(73) Assignee: ABBOTT LABORATORIES, Abbott Park (IL)

(*) Notice: Subject to any disclaimer, the term of this patent is extended or adjusted under 35 U.S.C. 154(b) by 0 days.

(21) Appl. No.: 15/724,203

(22) Filed: Oct. 3, 2017

(65) Prior Publication Data
US 2018/0104694 A1   Apr. 19, 2018

Related U.S. Application Data

(63) Continuation of application No. PCT/US2016/025785, filed on Apr. 2, 2016.
(Continued)

(51) Int. Cl.
*B01L 3/00* (2006.01)
*G01N 33/543* (2006.01)
*G01N 33/53* (2006.01)

(52) U.S. Cl.
CPC ... *B01L 3/502784* (2013.01); *B01L 3/502707* (2013.01); *B01L 3/502715* (2013.01);
(Continued)

(58) Field of Classification Search
CPC ......... B01L 3/502784; B01L 3/502707; B01L 3/502761; B01L 2400/0427; G01N 33/54373; G01N 33/5302
See application file for complete search history.

(56) References Cited

U.S. PATENT DOCUMENTS

| 5,187,096 A | 2/1993 | Giaever et al. |
| 5,241,070 A | 8/1993 | Law |

(Continued)

FOREIGN PATENT DOCUMENTS

| EP | 2 825 501 A1 | 1/2015 |
| JP | 2007-017155 A | 1/2007 |

(Continued)

OTHER PUBLICATIONS

Fair et al. Integrated chemical/biochemical sample collection, pre-concentration, and analysis on a digital microfluidic lab-on-a-chip platform, Proc. of SPIE vol. 5591, pp. 113-124. (Year: 2004).*
(Continued)

*Primary Examiner* — Melanie Brown
(74) *Attorney, Agent, or Firm* — Baker Botts L.L.P.

(57) ABSTRACT

Integrated devices that include a sample preparation component integrated with a detection component are disclosed. The sample preparation component may be a digital microfluidics module or a surface acoustic wave module which modules are used for combing a sample droplet with a reagent droplet and for performing additional sample preparation step leading to a droplet that contains beads/particles/labels that indicate presence or absence of an analyte of interest in the sample. The beads/particles/labels may be detected by moving the droplet to the detection component of the device, which detection component includes an array of wells.

20 Claims, 32 Drawing Sheets

Related U.S. Application Data

(60) Provisional application No. 62/142,858, filed on Apr. 3, 2015.

(52) U.S. Cl.
CPC .... *B01L 3/502761* (2013.01); *G01N 33/5302* (2013.01); *G01N 33/54373* (2013.01); *B01L 2200/0668* (2013.01); *B01L 2200/0689* (2013.01); *B01L 2200/10* (2013.01); *B01L 2200/142* (2013.01); *B01L 2300/089* (2013.01); *B01L 2300/0829* (2013.01); *B01L 2300/0858* (2013.01); *B01L 2300/0887* (2013.01); *B01L 2300/0893* (2013.01); *B01L 2300/12* (2013.01); *B01L 2300/161* (2013.01); *B01L 2400/0427* (2013.01)

(56) References Cited

U.S. PATENT DOCUMENTS

| | | |
|---|---|---|
| 5,270,163 A | 12/1993 | Gold et al. |
| 5,352,803 A | 10/1994 | Mattingly |
| 5,359,093 A | 10/1994 | Adamczyk et al. |
| 5,468,646 A | 11/1995 | Mattingly et al. |
| 5,475,096 A | 12/1995 | Gold et al. |
| 5,496,925 A | 3/1996 | Mattingly |
| 5,543,524 A | 8/1996 | Mattingly et al. |
| 5,567,588 A | 10/1996 | Gold et al. |
| 5,573,904 A | 11/1996 | Mattingly |
| 5,593,896 A | 1/1997 | Adamczyk et al. |
| 5,595,877 A | 1/1997 | Gold et al. |
| 5,620,850 A | 4/1997 | Bamdad et al. |
| 5,637,459 A | 6/1997 | Burke et al. |
| 5,683,867 A | 11/1997 | Biesecker et al. |
| 5,696,253 A | 12/1997 | Bruice et al. |
| 5,705,337 A | 1/1998 | Gold et al. |
| 5,783,699 A | 7/1998 | Mattingly et al. |
| 6,013,785 A | 1/2000 | Bruice et al. |
| 6,015,714 A | 1/2000 | Baldarelli et al. |
| 6,027,496 A | 2/2000 | Loomis et al. |
| 6,294,063 B1 | 9/2001 | Becker et al. |
| 6,413,792 B1 | 7/2002 | Sauer et al. |
| 6,428,959 B1 | 8/2002 | Deamer |
| 6,464,842 B1 | 10/2002 | Golovchenko et al. |
| 6,565,727 B1 | 5/2003 | Shenderov |
| 6,627,067 B1 | 9/2003 | Branton et al. |
| 6,679,841 B2 | 1/2004 | Bojan et al. |
| 6,773,566 B2 | 8/2004 | Shenderov |
| 6,783,643 B2 | 8/2004 | Golovchenko et al. |
| 6,911,132 B2 | 6/2005 | Pamula et al. |
| 6,942,968 B1 * | 9/2005 | Dickinson .......... G01N 21/6428 435/7.1 |
| 7,070,921 B2 | 7/2006 | Huang et al. |
| 7,591,936 B2 | 9/2009 | Sarrut |
| 7,718,445 B2 | 5/2010 | Martin |
| 7,906,293 B2 | 3/2011 | Mattingly et al. |
| 8,287,808 B2 | 10/2012 | Krupenkin et al. |
| 8,637,242 B2 | 1/2014 | Shen et al. |
| 8,895,292 B2 | 11/2014 | Söderlund et al. |
| 8,940,147 B1 | 1/2015 | Bartsch et al. |
| 9,017,937 B1 | 4/2015 | Turner et al. |
| 2002/0028457 A1 | 3/2002 | Empedocles et al. |
| 2002/0043463 A1 | 4/2002 | Shenderov |
| 2002/0197645 A1 | 12/2002 | Martin |
| 2003/0082633 A1 | 5/2003 | Martin et al. |
| 2003/0141189 A1 | 7/2003 | Lee et al. |
| 2003/0211502 A1 | 11/2003 | Sauer et al. |
| 2004/0149580 A1 | 8/2004 | Flory |
| 2005/0006224 A1 | 1/2005 | Golovchenko et al. |
| 2005/0126905 A1 | 6/2005 | Golovchenko et al. |
| 2006/0121544 A1 | 6/2006 | Boge et al. |
| 2007/0242105 A1 | 10/2007 | Srinivasan et al. |
| 2008/0187915 A1 | 8/2008 | Polonsky et al. |
| 2008/0274513 A1 | 11/2008 | Shenderov et al. |
| 2009/0192044 A1 | 7/2009 | Fouillet et al. |
| 2010/0181195 A1* | 7/2010 | Garcia Tello ....... B01F 13/0071 204/450 |
| 2010/0282609 A1 | 11/2010 | Pollack et al. |
| 2010/0307922 A1 | 12/2010 | Wu |
| 2011/0091989 A1* | 4/2011 | Sista ................. B01L 3/502761 436/174 |
| 2011/0104816 A1* | 5/2011 | Pollack ............. B01L 3/502784 436/174 |
| 2011/0212848 A1* | 9/2011 | Duffy ............... G01N 33/54313 506/9 |
| 2011/0308950 A1 | 12/2011 | Sakai et al. |
| 2012/0031773 A1* | 2/2012 | Miller ................ G01N 33/5438 205/777.5 |
| 2012/0080361 A1 | 4/2012 | Walavalkar et al. |
| 2012/0141997 A1 | 6/2012 | Meagher et al. |
| 2012/0268804 A1 | 10/2012 | Hadwen |
| 2013/0116128 A1 | 5/2013 | Shen et al. |
| 2013/0126358 A1 | 5/2013 | Lee et al. |
| 2013/0217103 A1* | 8/2013 | Bauer ................. B01F 13/0071 435/287.2 |
| 2013/0330247 A1 | 12/2013 | Wilson et al. |
| 2013/0345088 A1 | 12/2013 | Noji et al. |
| 2014/0141409 A1* | 5/2014 | Foley .................. C12Q 1/6806 435/5 |
| 2014/0174927 A1 | 6/2014 | Bashir et al. |
| 2014/0291152 A1 | 10/2014 | Conoci et al. |
| 2015/0069329 A1 | 3/2015 | Jeon et al. |
| 2015/0209779 A1 | 7/2015 | Harr et al. |
| 2016/0041179 A1 | 2/2016 | Ju et al. |
| 2018/0067038 A1* | 3/2018 | Fathollahi .............. G01N 15/06 |
| 2018/0111126 A1 | 4/2018 | Osmus et al. |

FOREIGN PATENT DOCUMENTS

| | | |
|---|---|---|
| JP | 2008-505631 A | 2/2008 |
| JP | 2009-534653 A | 9/2009 |
| JP | 2011-521222 A | 7/2011 |
| JP | 2012-230105 A | 11/2012 |
| JP | 2012-526556 A | 11/2012 |
| JP | 2013-172724 A | 9/2013 |
| JP | 2014-153366 A | 8/2014 |
| JP | 2014-521956 A | 8/2014 |
| JP | 2014-169920 A | 9/2014 |
| WO | WO 00/34527 A2 | 6/2000 |
| WO | WO 02/29076 A1 | 4/2002 |
| WO | WO 2004/085609 A2 | 10/2004 |
| WO | WO 2007/136386 A2 | 11/2007 |
| WO | WO 2009/111431 A2 | 9/2009 |
| WO | WO 2010/040227 A1 | 4/2010 |
| WO | WO 2010/117470 A2 | 10/2010 |
| WO | WO 2011/023 949 A2 | 3/2011 |
| WO | WO 2011/057197 A2 | 5/2011 |
| WO | WO 2011/137533 A1 | 11/2011 |
| WO | WO 2012/121310 A1 | 9/2012 |
| WO | WO 2013/066441 A2 | 5/2013 |
| WO | WO 2013/083621 A1 | 6/2013 |
| WO | WO 2013/167952 A1 | 11/2013 |
| WO | WO 2013/167955 A1 | 11/2013 |
| WO | WO 2014/062551 A1 | 4/2014 |
| WO | WO 2014/066704 A1 | 5/2014 |
| WO | WO 2014/144898 A1 | 9/2014 |
| WO | WO 2015/031849 A1 | 3/2015 |

OTHER PUBLICATIONS

Witters et al. Digital microfluidics-enabled single-molecule detection by printing and sealing single magnetic beads in femtoliter droplets, Lab on a Chip, vol. 13, pp. 2047-2054. (Year: 2013).*
U.S. Appl. No. 15/724,200, Dec. 26, 2018 Non-Final Office Action.
U.S. Appl. No. 15/724,200, Oct. 17, 2018 Response to Restriction Requirement.
U.S. Appl. No. 15/724,200, Aug. 30, 2018 Restriction Requirement.
U.S. Appl. No. 15/724,213, Dec. 21, 2018 Response to Restriction Requirement.
U.S. Appl. No. 15/724,213, Oct. 25, 2018 Restriction Requirement.

(56) References Cited

OTHER PUBLICATIONS

Adamczyk et al., "Chemiluminescence quenching of pteroic acid-N-sulfonyl-acridinium-9-carboxamide conjugates by folate binding protein," Bioorg. Med. Chem. Lett. 14:2313-2317 (2004).

Adamczyk et al., "Chemiluminescent acridinium-9-carboxamide boronic acid probes: Application to a homogeneous glycated hemoglobin assay," Bioorg. Med. Chem. Lett. 16:1324-1328 (2006).

U.S. Appl. No. 15/724,200 (US 2018/0095067), filed Oct. 3, 2017 (Apr. 5, 2018).

U.S. Appl. No. 15/724,213, filed Oct. 3, 2017.

Adamczyk et al., "Chemiluminescent N-Sulfonylacridinium-9-Carboxamides and Their Application in Clinical Assays," Luminescence Biotechnology: Instruments and Applications, CRC Press, pp. 77-105 (2002).

Adamczyk et al., "Intrinsic factor-mediated modulation of cyanocobalamin-N-sulfonyl-acridinium-9-carboxamide chemiluminescence," Biorg. Med. Chem. Lett. 14:3917-3921 (2004).

Adamczyk et al., "Linker-Mediated Modulation of the Chemiluminescent Signal from N10-(3-Sulfopropyl)-N-sulfonylacridinium-9-carboxamide Tracers," Bioconjugate Chem. 11:714-724 (2000).

Adamczyk et al., "Neopentyl 3-Triflyloxypropanesulfonate. A Reactive Sulfopropylation Reagent for the Preparation of Chemiluminescent Labels," J. Org. Chem. 63:5636-5639 (1998).

Adamczyk et al., "Regiodependent Luminescence Quenching of Biotinylated N-Sulfonyl-acridinium-9-carboxamides by Avidin," Org. Lett. 5(21):3779-3782 (2003).

Adamczyk et al., "Synthesis of a Chemiluminescent Acridinium Hydroxylamine (AHA) for the Direct Detection of Abasic Sites in DNA," Org. Lett. 1(5):779-781 (1999).

Adamczyk et al., Modulation of the Chemiluminescent Signal from N10 -(3-Sulfopropyl)-N-Sulfonylacridinium-9-carboxamides, Tetrahedron 55:10899-10914 (1999).

Agasti et al., "Photocleavable DNA Barcode-Antibody Conjugates Allow Sensitive and Multiplexed Protein Analysis in Single Cells," J. Am. Chem. Soc., 134:18499-18502 (2012).

Banta et al., "Replacing Antibodies: Engineering New Binding Proteins," Annu. Rev. Biomed. Eng. 15:93-113 (2013).

Behar et al., "Tolerance of the archaeal Sac7d scaffold protein to alternative library designs: characterization of anti-immunoglobulin G Affitins," Protein Engineering, Design & Selection 26(4):267-275 (2013).

Burgess et al., "An Approach to Photolabile, Fluorescent Protecting Groups," J. Org. Chem. 62:5165-5168 (1997).

Chatteijee et al., "Droplet-based microfluidics with nonaqueous solvents and solutions," Lab Chip, 6:199-206 (2006).

Crawford et al., "Pepetide aptamers: Tools for biology and drug discovery," Brief Funct Genomic Proteomic 2:72-79 (2003).

Dutz et al., "Magnetic particle hyperthermia-a promising tumour therapy?" Nanotechnology, 25:452001 (2014).

Fan et al., "General digital microfluidic platform manipulating dielectric and conductive droplets by dielectrophoresis and electrowetting," Lab Chip, 9:1236-1242 (2009).

Gilbreth et al., "Structural insights for engineering binding proteins based on non-antibody scaffolds," Current Opinion in Structural Biology 22:413-420 (2012).

Gottlin et al., "Isolation of Novel EGFR-Specific VHH Domains," Journal of Biomolecular Screening, 14:77-85 (2009).

Guillier et al., "Linkers and Cleavage Strategies in Solid-Phase Organic Synthesis and Combinatorial Chemistry," Chem. Rev. 100:2091-2157 (2000).

Hall et al., "Hybrid pore formation by directed insertion of α-haemolysin into solid-state nanopores," Nature Nanotechnology, 5:874-877 (2010).

Haugland, Handbook of Fluorescent Probes and Research Chemicals, 6th Edition (1996) (Table of Contents).

Heller, "Electrical Wiring of Redox Enzymes," Acc. Chem. Res. 23(5):128-134 (1990).

Heng et al., "Sizing DNA Using a Nanotube-Diameter Pore," Biophy J 87:2905-2911 (2004).

Hille, B, 2001, Ion Channels of Excitable Membranes, 3rd Ed., Sinauer Associates, Inc., Sunderland, Mass.

Holt et al., "Domain antibodies: proteins for therapy," Trends in Biotechnology 21(11):484-490 (2003).

International Search Report dated Aug. 26, 2016 in International Application No. PCT/US2016/025785.

International Search Report dated Sep. 22, 2016 in International Application No. PCT/US2016/025787.

Jirage et al., "Nanotubule-Based Molecular-Filtration Membranes," Science, 278:655-658 (1997).

Kasianowiscz et al., "Characterization of individual polynucleotide molecules using a membrane channel," PNAS USA 93:13770-13773 (1996).

Kassies et al., "Combined AFM and confocal fluorescence microscope for applications in bio-nanotechnology," J Microsc 217(Part 1):109-116 (2005).

Kazane et al., "Site-specific DNA-antibody conjugates for specific and sensitive immune-PCR," PNAS USA 109(10):3731-3736 (2012).

Kowalczyk et al., "Modeling the conductance and DNA blockade of solid-state nanopores," Nanotech., 22:315101 (2011).

Kwok et al., "Nanopore Fabrication by Controlled Dielectric Breakdown," Supplementary Information Section 8, DNA Translocation (2014).

Kwok et al., "Nanopore Fabrication by Controlled Dielectric Breakdown," PLoS One 9(3):e92880 (2014).

Lee et al., "Studies on a Dithiane-Protected Benzoin Photolabile Safety Catch Linker for Solid-Phase Synthesis," J. Org. Chem. 64:3454-3460 (1999).

Li et al., "DNA molecules and configurations in a solid-state nanopore microscope," Nature Materials 2:611-615 (2003).

Li et al., "Ion-beam sculpting at nanometer length scales," Nature 412:166-169 (2001).

Li et al., "Quantized tunneling current in the metallic nanogaps formed by electrodeposition and etching," Applied Physics Lett. 77(24):3995-3997 (2000).

Lo et al., "Novel roll-to-roll lift-off patterned active-matrix display on flexible polymer substrate," Microelectronic Engineering 86:979-983 (2009).

Mattingly et al., "Chemiluminescent N-Sulfonylacridinium-9-Carboxamides and Their Application in Clinical Assays," Chapter 5, Luminescence Biotechnology: Instruments and Applications; Dyke, K. V. Ed.; CRC Press: Boca Raton, pp. 77-105 (2002).

Mattingly, "Chemiluminescent 10-Methyl-Acridinium-9-(N-Sulphonylcarboxamide) Salts. Synthesis and Kinetics of Light Emission," J. Biolumin. Chemilumin. 6:107-114 (1991).

McCapra et al., "Chemiluminescence Involving Peroxide Decompositions," Photochem. Photobiol. 4:1111-1121 (1965).

McEnaney et al., "Antibody-Recruiting Molecules: An Emerging Paradigm for Engaging Immune Function in Treating Human Disease," ACS Chem. Biol. 7:1139-1151 (2012).

Menon et al., "Fabrication and Evaluation of Nanoelectrode Ensembles," Anal Chem 67:1920-1928 (1995).

Millward et al., "Iterative in Situ Click Chemistry Assembles a Branched Capture Agent and Allosteric Inhibitor for AktI," J. Am. Chem. Soc. 133:18280-18288 (2011).

Murphy et al., "Fast photoinduced electron transfer through DNA intercalation," Proc Natl Acad Sci USA 91:5315-5319 (1994).

Patel et al., "Selection of a high-affinity WW domain against the extracellular region of VEGF receptor isoform-2 from a combinatorial library using CIS display," Protein Engineering, Design & Selection 26(4):307-315 (2013).

Polak and Van Noorden, Introduction to Immunocytochemistry, 2nd ed., Springer Verlag, N.Y. (1997), (Table of Contents).

Rader, "Chemically programmed antibodies," Trends in Biotechnology 32(4): 186-197 (2014).

Rauch et al., "On the Structure of Mitochondrial Porins and its Homologies with Bacterial Porins," Biochem Biophys Res Comm 200(2):908-915 (1994).

Razavi et al., "Stable and versatile active acridinium esters I," Luminescence 15:239-244 (2000).

Razavi et al., "Stable and versatile active acridinium esters II," Luminescence 15: 245-249 (2000).

(56) References Cited

OTHER PUBLICATIONS

Reverdatto et al., "Combinatorial Library of Improved Peptide Aptamers, CLIPs to Inhibit RAGE Signal Transduction in Mammalian Cells," PLoS One 8(6):e65180 (2013).
Shum et al., "Nucleic Acid Aptamers as Potential Therapeutic and Diagnostic Agents for Lymphoma," J Cancer Ther. 4:872-890 (2013).
Storm et al., "Fabrication of solid-state nanopores with single-nanometre precision," Nature Materials 2:537-540 (2003).
Szabo et al., "DNA Translocation Across Planar Bilayers Containing Bacillus subtilis Ion Channels," J. Biol. Chem. 272(40):25275-25282 (1997).
Szabo et al., "Double-stranded DNA can be translocated across a planar membrane containing purified mitochondrial porin," FASEB J. 12:495-502 (1998).
Tiede et al., "Adhiron: a stable and versatile peptide display scaffold for molecular recognition applications," Protein Engineering, Design & Selection 27(5):145-155 (2014).
Tropini et al., "Multi-Nanopore Force Spectroscopy for DNA Analysis," Biophysical Journal, 92:1632-1637 (2007).
Walsh et al., "Laser-assisted photothermal heating of a plasmonic nanaoparticle-suspended droplet in a microchannel," Analyst, 140:1535-1542 (2015).
Wells, High Throughput Bioanalytical Sample Preparation. Methods and Automation Strategies, Progress in Pharmaceutical and Biomedical Analysis, vol. 5, Elsevier (2003) (Table of Contents).
Xiang et al., "A Controllable Electrochemical Fabrication of Metallic Electrodes with a Nanometer/Angstrom-Sized Gap Using an Electric Double Layer as Feedback," Angew. Chem. Int. Ed. 44:1265-1268 (2005).
Zhang et al., "Tumor-Targeted Drug Delivery with Aptamers," Curr Med Chem. 18:4185-4194 (2011).
Zhu et al., "Nucleic Acid Aptamers: An Emerging Frontierin Cancer Therapy," Chem Commun 48:10472-10480 (2012).
U.S. Appl. No. 15/724,213, Mar. 1, 2019 Non-Final Office Action.
U.S. Appl. No. 15/724,200, Jun. 6, 2019 Non-Final Office Action.
U.S. Appl. No. 15/724,213, Oct. 30, 2019 Notice of Allowance.
Fair et al., "Chemical and Biological Applications of Digital Microfluidic Devices," IEEE Design & Test of Computers 24(1):10-24 (2007).
Punnamaraju "Voltage and Photo Induced Effects in Droplet Interface-Bilayer Lipid Membranes," pp. 1-160 (2011).
U.S. Appl. No. 15/724,200, Feb. 6, 2020 Non-Final Office Action.
Tahvildari et al., "Integrating nanopore sensors within microfluidic channel arrays using controlled breakdown," Lab on a Chip 15:1407-1411 (2015).

* cited by examiner

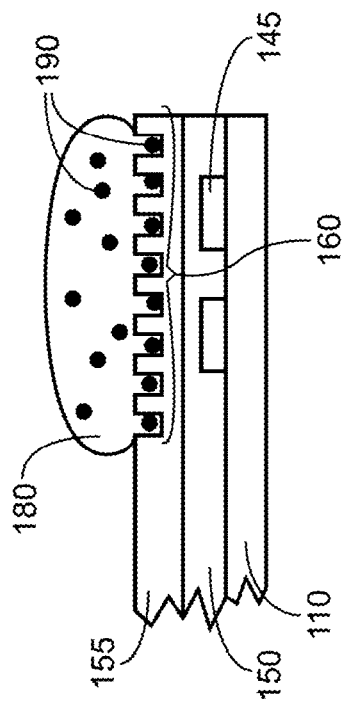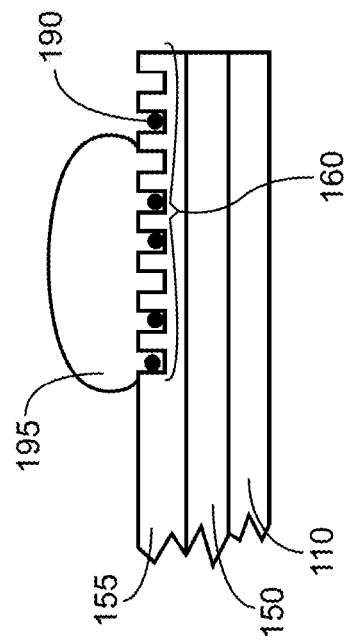
FIG. 4A
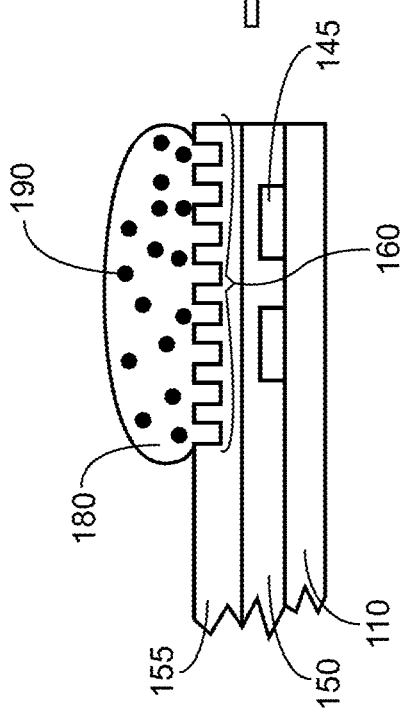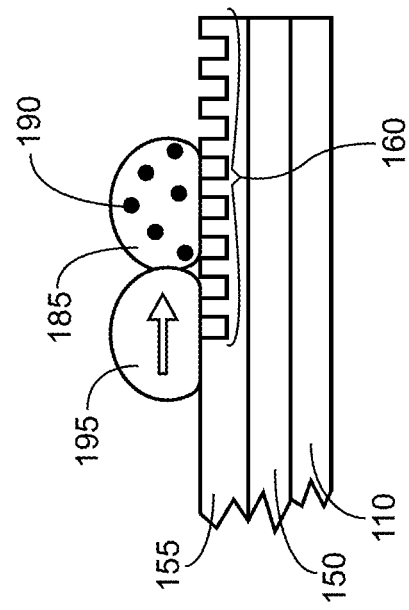
FIG. 4B

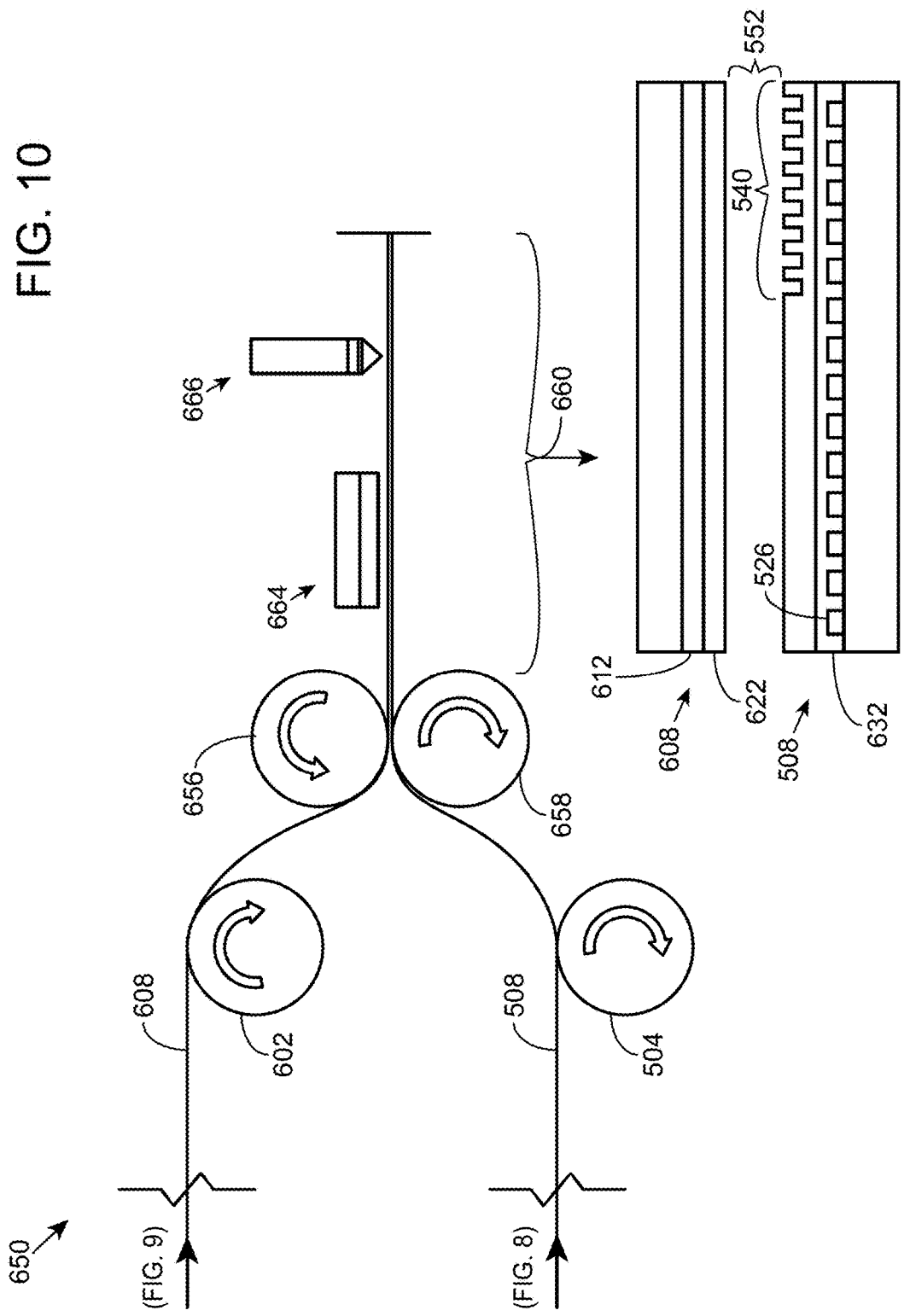

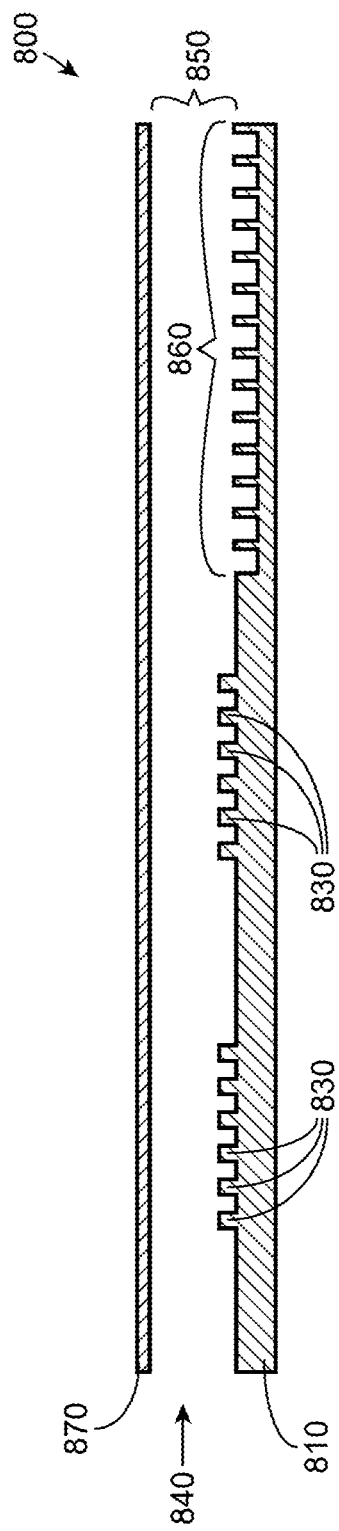
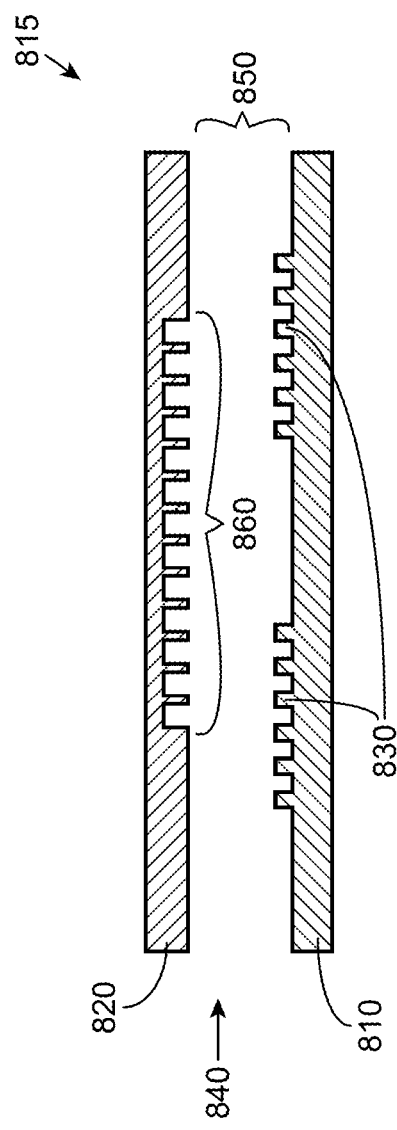
FIG. 13A
FIG. 13B

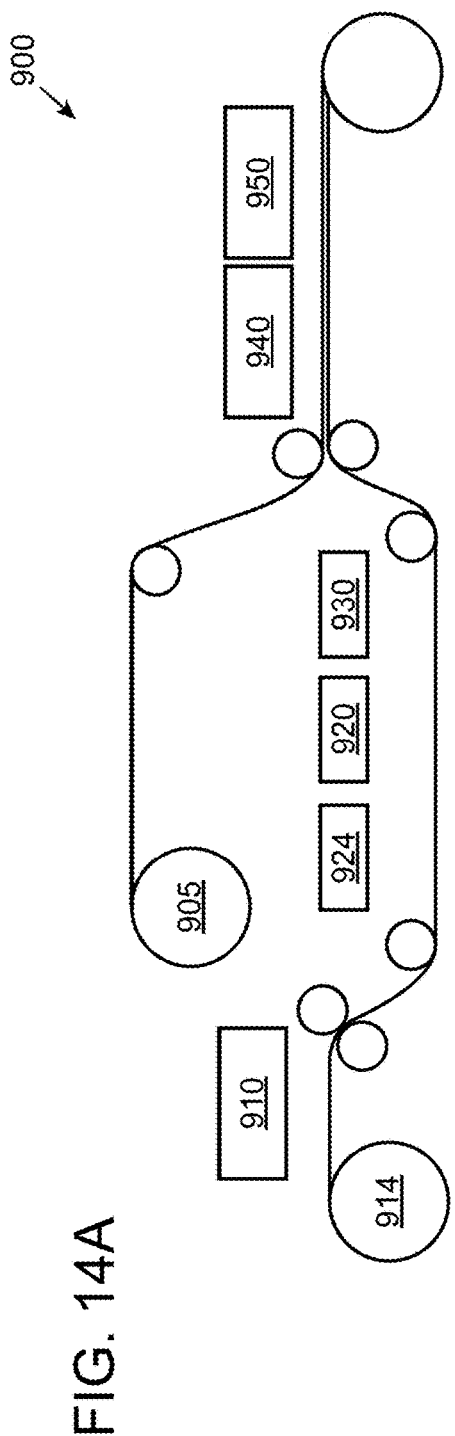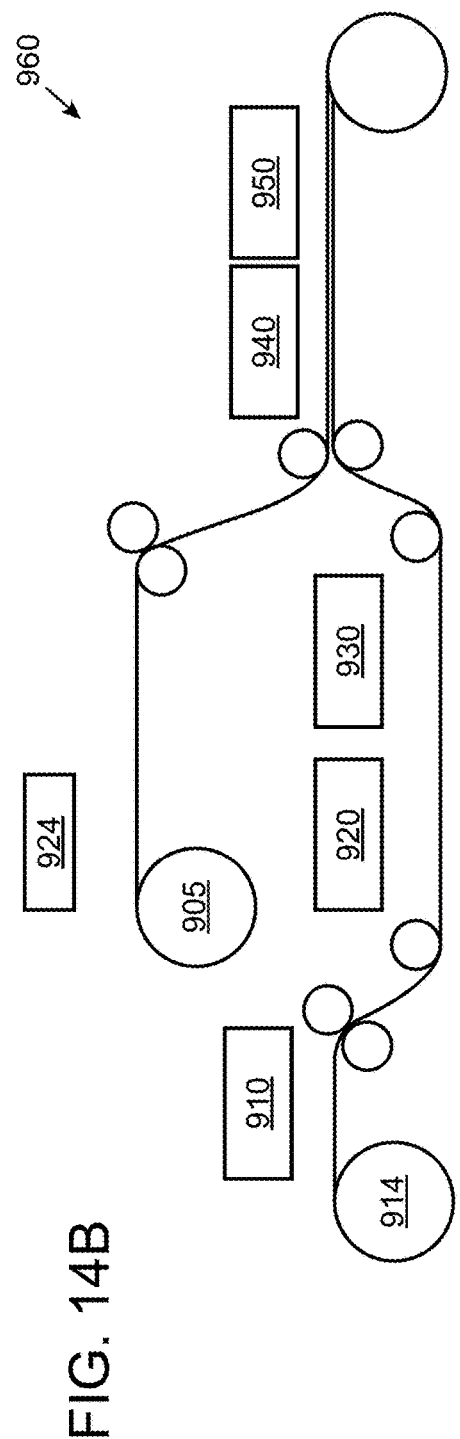
FIG. 14A
FIG. 14B

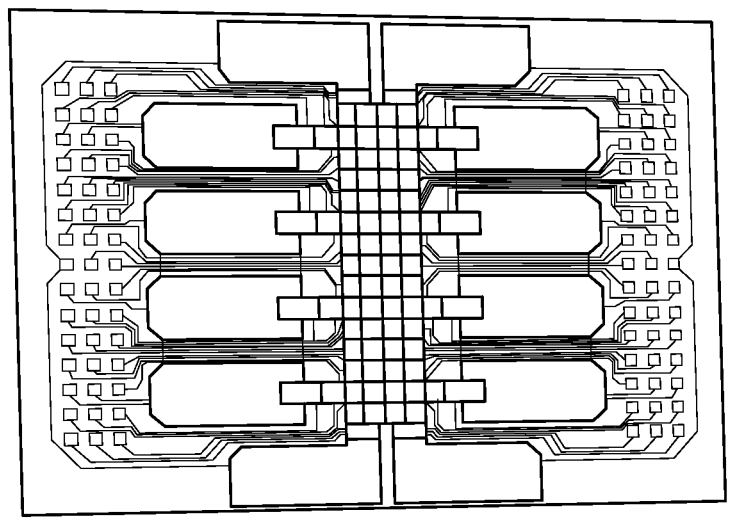
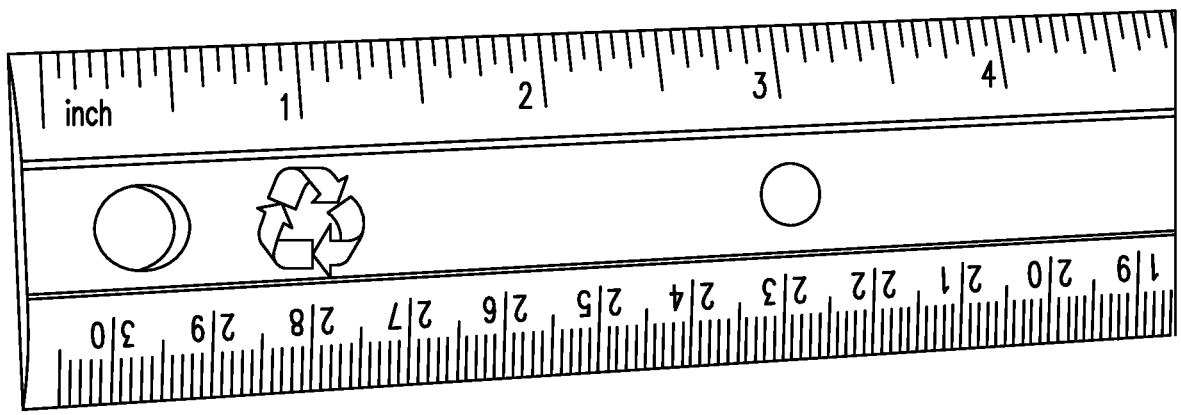
FIG. 19

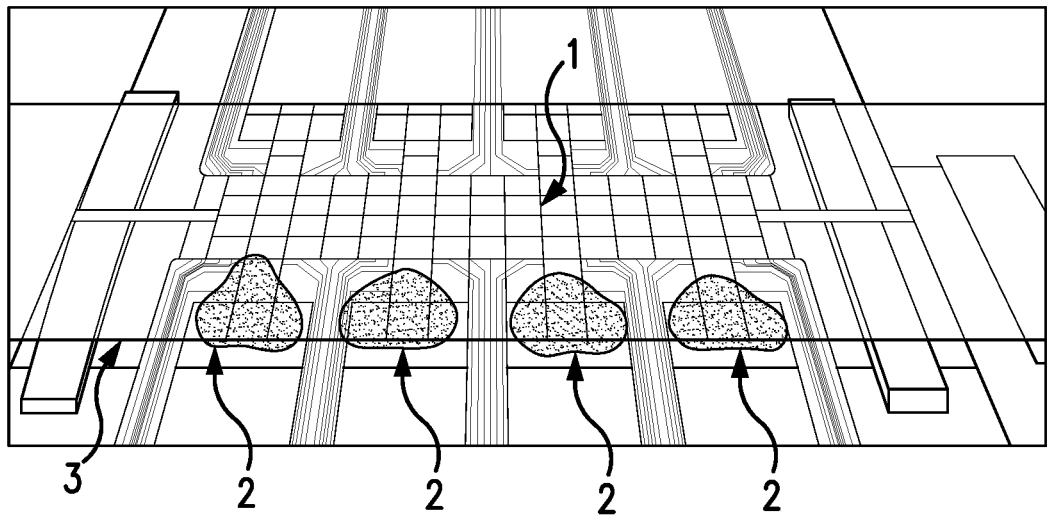
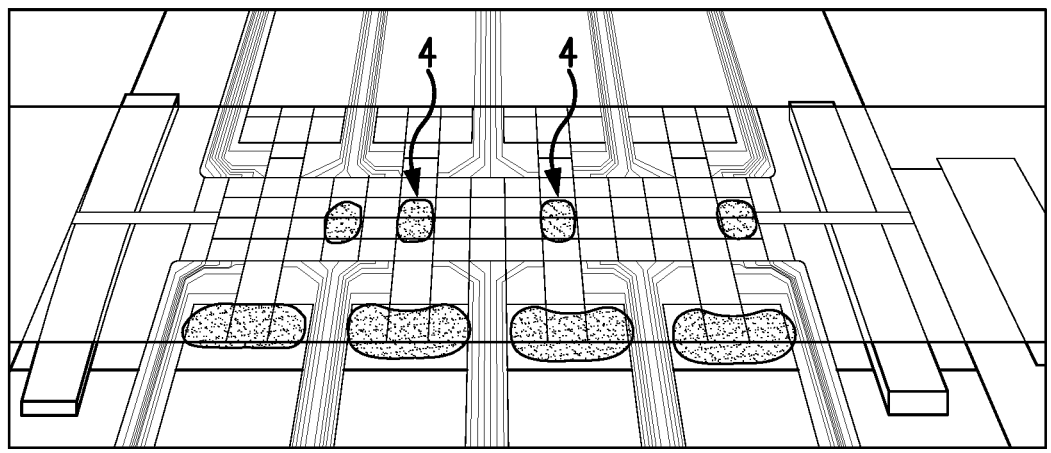
FIG. 20

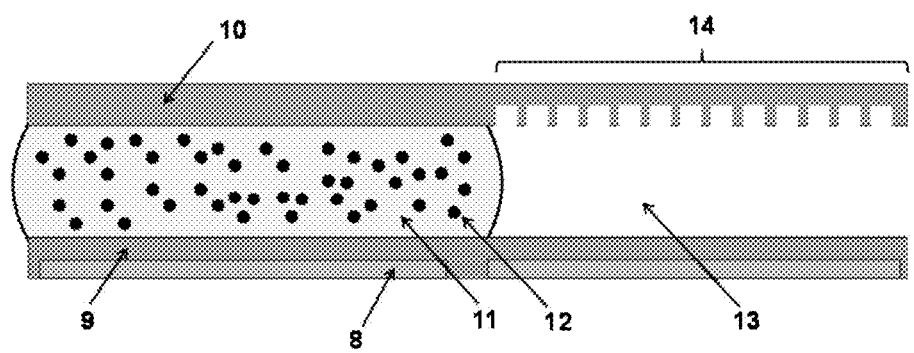
FIG. 29
FIG. 30A
FIG. 30B
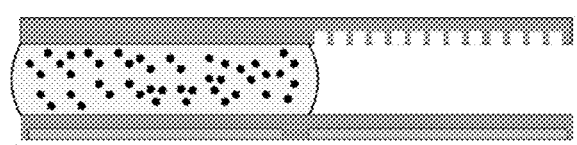
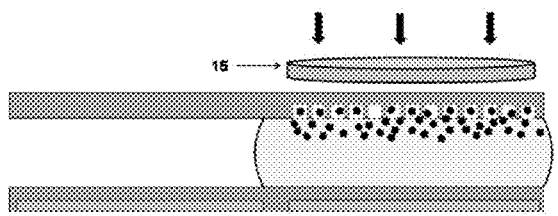
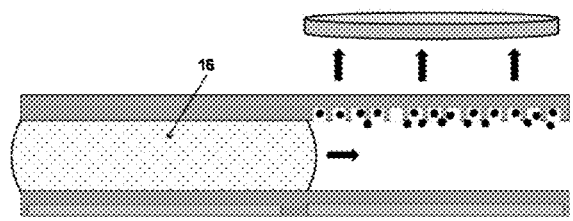
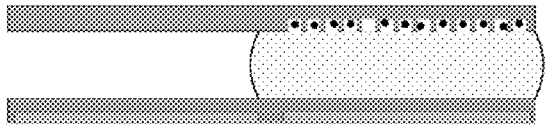
FIG. 30C
FIG. 30D

DEVICES AND METHODS FOR SAMPLE ANALYSIS

CROSS-REFERENCE TO RELATION RELATED APPLICATIONS

This application is a continuation of International Patent Application No. PCT/US2016/025785, filed Apr. 2, 2016, which claims the benefit of U.S. Provisional Patent Application No. 62/142,858 filed Apr. 3, 2015, each of which is incorporated herein by reference in its entirety.

INTRODUCTION

Analyte analysis is usually performed by carrying out a sample preparation step that is either performed manually or using complicated robotics. After sample preparation, the assaying of an analyte in the prepared sample further involves use of expensive and complicated systems for transporting the prepared sample to a machine that then performs analysis of an analyte in the prepared sample.

Integrated devices that can be used to prepare a sample and assay the prepared sample are highly desirable in the field of analyte analysis. Such integrated devices would offer a low cost option and would considerably increase the ease of performing analyte analysis, especially in clinical applications, such as point-of-care applications.

As such, there is an interest in integrated devices for performing analyte analysis.

SUMMARY

An integrated microfluidic and analyte detection device is disclosed. Also provided herein are exemplary methods for using an integrated microfluidic and analyte detection device and associated systems.

Disclosed is a digital microfluidic and analyte detection device, including a first substrate and a second substrate, wherein the second substrate is separated from the first substrate by a gap, the first substrate including a plurality of electrodes to generate electrical actuation forces on a liquid droplet; and an array of wells dimensioned to hold a portion of the liquid droplet, wherein at least a portion of the array of wells is positioned between one or more of the plurality of electrodes and the gap.

In some embodiments, the plurality of electrodes is positioned on a surface of the first substrate. In certain embodiments, the device further includes a first layer disposed on the surface of the first substrate and covering the plurality of electrodes. In some embodiments, the first substrate includes a first portion at which the liquid droplet is introduced and a second portion toward which a liquid droplet is moved. In certain embodiments, the plurality of electrodes and the first layer extend from the first portion to the second portion of the first substrate. In certain embodiments, the array of wells is positioned in the second portion of the first substrate. In certain embodiments, the second substrate includes a first portion and a second portion, wherein the first portion is in facing arrangement with the first portion of the first substrate and the second portion is in facing arrangement with the array of wells. In certain embodiments, the second portion of the second substrate is substantially transparent to facilitate optical interrogation of the array of wells.

In some embodiments, the device further includes a second layer disposed on a surface of the first layer. In certain embodiments, the second layer extends over the first and second portions of the first substrate. In certain embodiments, the first layer is a dielectric layer and the second layer is a hydrophobic layer. In certain embodiments, the array of wells is positioned in the second layer. In certain embodiments, the array of wells is positioned in the first layer. In certain embodiments, the array of wells has a hydrophilic surface.

In some embodiments, the array of wells include a sidewall that is oriented to facilitate receiving and retaining of beads or particles present in droplets moved over the well array. In certain embodiments, the array of wells include a first sidewall opposite to a second side wall, wherein the first sidewall is oriented at an obtuse angle with reference to a bottom of the wells, and wherein the second sidewall is oriented at an acute angle with reference to the bottom of the wells, wherein movement of droplets is in a direction parallel to the bottom of the wells and from the first sidewall to the second sidewall. In certain embodiments, the array of wells have a frustoconical shape with a narrower part of the frustoconical shape providing an opening of the array of wells. In certain embodiments, the array of wells include a first sidewall opposite to a second side wall, wherein a top portion of the first sidewall is oriented at an obtuse angle with reference to a bottom of the wells and a bottom portion of the sidewall is oriented perpendicular to the bottom of the wells, and wherein the second sidewall is oriented perpendicular with reference to the bottom of the wells, wherein the movement of droplets is in a direction parallel to the bottom of the wells and from the first sidewall to the second sidewall, wherein the top portion of the first side wall is at an opening of the wells.

Also disclosed is a digital microfluidic and analyte detection device, including a first substrate and a second substrate defining the device, wherein the second substrate is separated from the first substrate by a gap, wherein the device includes a first portion and a second portion; and the first portion includes a plurality of electrodes to actuate combining of a first liquid droplet containing an analyte of interest from a biological sample and a second liquid droplet containing at least one bead; and the second portion includes an array of wells dimensioned to hold a portion of the liquid droplet.

In some embodiments, the plurality of electrodes are only positioned in the first portion of the device. In certain embodiments, the plurality of electrodes is positioned on a surface of the first substrate. In some embodiments, the device further includes a first layer disposed on the surface of the first substrate and covering the plurality of electrodes. In certain embodiments, the first substrate includes a first portion at which the liquid droplet is introduced and a second portion toward which a liquid droplet is moved. In certain embodiments, the plurality of electrodes and the first layer extend from the first portion to the second portion of the first substrate. In certain embodiments, the array of wells is positioned in the second portion of the first substrate.

In certain embodiments, the second substrate includes a first portion and a second portion, wherein the first portion is in facing arrangement with the first portion of the first substrate and the second portion is in facing arrangement with the array of wells.

In certain embodiments, the second portion of the second substrate is substantially transparent to facilitate optical interrogation of the array of wells. In certain embodiments, the plurality of electrodes are configured to move a droplet placed in the gap towards the second portion of the device, the device includes a capillary portion fluidically connecting the first portion to the second portion, wherein the capillary includes a hydrophilic material to facilitate movement of the droplet from the first portion to the second portion via the capillary portion in absence of an electric force.

In some embodiments, the device further includes a second layer is disposed on an upper surface of the first layer. In certain embodiments, the second layer extends over the first substrate. In certain embodiments, the first layer is a dielectric layer and the second layer is a hydrophobic layer.

In some embodiments, the plurality of wells is positioned in the second layer. In certain embodiments, the array of wells is positioned in the first layer. In certain embodiments, the array of wells has a hydrophilic surface. In certain embodiments, the wells include a sidewall that is oriented to facilitate receiving and retaining of nanobeads or nanoparticles present in droplets moved over the well array. In certain embodiments, the wells include a first sidewall opposite to a second side wall, wherein the first sidewall is oriented at an obtuse angle with reference to a bottom of the wells, and wherein the second sidewall is oriented at an acute angle with reference to the bottom of the wells, wherein the movement of droplets is in a direction parallel to the bottom of the wells and from the first sidewall to the second sidewall. In certain embodiments, the wells have a frustoconical shape with the narrower part of the frustoconical shape providing the opening of the wells. In certain embodiments, the wells include a first sidewall opposite to a second side wall, wherein a top portion of the first sidewall is oriented at an obtuse angle with reference to a bottom of the wells and a bottom portion of the sidewall is oriented perpendicular to the bottom of the wells, and wherein the second sidewall is oriented perpendicular to the bottom of the wells, wherein the movement of droplets is in a direction parallel to the bottom of the wells and from the first sidewall to the second sidewall, wherein the top portion of the first side wall is at an opening of the wells.

Also disclosed herein is a surface acoustic wave microfluidic and analyte detection device, including a first substrate and a second substrate, wherein the second substrate is separated from the first substrate by a gap, wherein the device includes a first portion and a second portion, the first portion including a superstrate coupled to a surface acoustic wave generating component; and the second portion including a plurality of wells positioned on the first substrate or the second substrate.

In some embodiments, the superstrate includes phononic structures on an upper surface of the superstrate. In certain embodiments, the superstrate overlays a piezoelectric crystal layer. In certain embodiments, the second substrate is substantially transparent.

Also disclosed herein is a surface acoustic wave microfluidic and analyte detection device, including a first substrate and a second substrate, wherein the second substrate is separated from the first substrate by a gap, the first substrate including a plurality of wells, and the second substrate including phononic structure, wherein the plurality of wells and the phononic structures are located across to each other.

In some embodiments, the second substrate is a superstrate. In certain embodiments, the superstrate is disposed on the second substrate and the phononic structure are located on the superstrate. In certain embodiments, the first substrate, second substrate and superstrate are substantially transparent.

Also disclosed are methods of detecting or measuring an analyte of interest in a liquid droplet. In certain embodiments, the method involves the steps of providing a first liquid droplet containing an analyte of interest, providing a second liquid droplet containing at least one solid support which contains a specific binding member that binds to the analyte of interest, using energy to exert a force to manipulate the first liquid droplet with the second liquid droplet to create a mixture, moving all or at least a portion of the mixture to an array of wells, wherein one or more wells of the array is of sufficient size to accommodate the at least one solid support, adding a detectable label to the mixture either before or after moving a portion of the mixture to array of wells, and detecting the analyte of interest in the wells.

In certain embodiments, the at least one solid support include at least one binding member that specifically binds to the analyte of interest. In certain embodiments, the method involves adding a detectable label to the mixture before moving at least a portion of the mixture to the array of wells. In certain embodiments, the method involves adding a detectable label to the mixture after moving at least a portion of the mixture to the array of wells. In certain embodiments, the detectable label include at least one binding member that specifically binds to the analyte of interest. In certain embodiments, the detectable label includes a chromagen, a fluorescent compound, an enzyme, a chemiluminescent compound or a radioactive compound. In certain embodiments, the binding member is a receptor or an antibody.

In certain embodiments, the energy used is an electric actuation force or acoustic force. In certain embodiments, the electric actuation force is droplet actuation, electrophoresis, electrowetting, dielectrophoresis, electrostatic actuation, electric field mediated, electrode mediated, capillary force, chromatography, centrifugation, or aspiration. In certain embodiments, the acoustic force is surface acoustic wave.

In certain embodiments, generating an electric actuation force includes generating an alternating current. In certain embodiments, the alternating current has a root mean squared (rms) voltage of 10 V or more. In certain other embodiments, the alternating current has a frequency in a radio frequency range.

In certain embodiments, the first liquid droplet is a polarizable liquid, the second liquid droplet is a polarizable liquid, the mixture is a polarizable liquid or both the first liquid droplet and second liquid droplet are each polarizable liquids.

In certain embodiments, the method further includes positioning the at least a portion of the mixture over the array of wells using an electric actuation force. In certain other embodiments, the method further includes positioning the at least a portion of the mixture over the array of wells using a capillary element configured to facilitate movement of the mixture to the array of wells.

In certain embodiments, the supports are magnetic solid supports. In certain other embodiments, when magnetic solid supports are used, an electric actuation force and a magnetic field are applied from opposite directions relative to the at least a portion of the mixture. In certain embodiments, the method further includes mixing the mixture by moving the mixture back and forth, moving the mixture in a circular pattern, splitting the mixture into two or more submixtures and merging the submixtures. In certain embodiments, the mixture is an aqueous liquid. In certain other embodiments, the mixture is an immiscible liquid. In certain other embodiments the liquid droplet is a hydrophobic liquid droplet. In certain embodiments, the array of wells has a hydrophilic surface. In certain other embodiments, the array of wells has a hydrophobic surface. In certain embodiments, the substrate includes a hydrophilic surface. In certain other embodiments, the substrate includes a hydrophobic surface. In certain embodiments, the method further includes generating an electric actuation force with a series of electrodes to move the mixture to the array of wells to seal the loaded wells.

In certain embodiments, one or more wells of the array are loaded with at least one solid support. In certain other embodiments, the loading includes applying a magnetic field to facilitate movement of at least one solid support into the one or more wells of the array. In certain other embodiments, the method further includes removing any solid supports that are not loaded into a well of the array after the loading. In certain other embodiments, the removing includes generating an electric actuation force with the series of electrodes to move a polarizable fluid droplet to the array of wells to move the at least a portion of the mixture to a distance from the array of wells. In certain other embodiments, the removing includes generating an electric actuation force with the series of electrodes to move an aqueous washing droplet across the array of wells.

In certain embodiments, the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

In other embodiments, the method includes the steps of providing a first liquid droplet containing an analyte of interest, providing a second liquid droplet containing a detectable label which contains a specific binding member that binds to the analyte of interest, using energy to exert a force to manipulate the first liquid droplet and the second liquid droplet to create a mixture, moving all or at least a portion of the mixture to an array of wells, and detecting the analyte of interest in the wells.

In certain embodiments, the detectable label includes a chromagen, a fluorescent compound, an enzyme, a chemiluminescent compound or a radioactive compound. In certain embodiments, the binding member is a receptor or an antibody.

In certain embodiments, the energy used is an electric actuation force or acoustic force. In certain embodiments, the electric actuation force is droplet actuation, electrophoresis, electrowetting, dielectrophoresis, electrostatic actuation, electric field mediated, electrode mediated, capillary force, chromatography, centrifugation, or aspiration. In certain embodiments, the acoustic force is surface acoustic wave.

In certain embodiments, generating an electric actuation force includes generating an alternating current. In certain embodiments, the alternating current has a root mean squared (rms) voltage of 10 V or more. In certain other embodiments, the alternating current has a frequency in a radio frequency range.

In certain embodiments, the first liquid droplet is a polarizable liquid, the second liquid droplet is a polarizable liquid, the mixture is a polarizable liquid or both the first liquid droplet and second liquid droplet are each polarizable liquids.

In certain embodiments, the method further includes positioning the at least a portion of the mixture over the array of wells using an electric actuation force. In certain other embodiments, the method further includes positioning the at least a portion of the mixture over the array of wells using a capillary element configured to facilitate movement of the mixture to the array of wells.

In certain embodiments, the method further includes mixing the mixture by moving the mixture back and forth, moving the mixture in a circular pattern, splitting the mixture into two or more submixtures and merging the submixtures. In certain embodiments, the mixture is an aqueous liquid. In certain other embodiments, the mixture is an immiscible liquid. In certain other embodiments the liquid droplet is a hydrophobic liquid droplet. In certain embodiments, the array of wells has a hydrophilic surface. In certain other embodiments, the array of wells has a hydrophobic surface. In certain embodiments, the substrate includes a hydrophilic surface. In certain other embodiments, the substrate includes a hydrophobic surface. In certain embodiments, the method further includes generating an electric actuation force with a series of electrodes to move the mixture to the array of wells to seal the loaded wells.

In certain embodiments, one or more wells of the array are loaded with at least one detectable label. In certain other embodiments, the removing includes generating an electric actuation force with the series of electrodes to move a polarizable fluid droplet to the array of wells to move the at least a portion of the mixture to a distance from the array of wells. In certain other embodiments, the removing includes generating an electric actuation force with the series of electrodes to move an aqueous washing droplet across the array of wells.

In certain embodiments, the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

In other embodiments, the method includes the steps of measuring an analyte of interest in a liquid droplet, the method includes providing a first liquid droplet containing an analyte of interest, providing a second liquid droplet containing at least one solid support which contains a specific binding member that binds to the analyte of interest, using energy to exert a force to manipulate the first liquid droplet with the second liquid to create a mixture, moving all or at least a portion of the mixture to an array of wells, wherein one or more wells of the array is of sufficient size to accommodate the at least one solid support, adding a detectable label to the mixture either before or after moving a portion of the mixture to array of wells, and measuring the detectable label in the wells.

In certain embodiments, the at least one solid support includes at least one binding member that specifically binds to the analyte of interest. In certain embodiments, the method involves adding a detectable label to the mixture before moving at least a portion of the mixture to the array of wells. In certain embodiments, the method involves adding a detectable label to the mixture after moving at least a portion of the mixture to the array of wells. In certain embodiments, the detectable label includes at least one binding member that specifically binds to the analyte of interest. In certain embodiments, the detectable label includes a chromagen, a fluorescent compound, an enzyme, a chemiluminescent compound or a radioactive compound. In certain embodiments, the binding member is a receptor or an antibody.

In certain embodiments, the energy used is an electric actuation force or acoustic force. In certain embodiments, the electric actuation force is droplet actuation, electrophoresis, electrowetting, dielectrophoresis, electrostatic actuation, electric field mediated, electrode mediated, capillary force, chromatography, centrifugation, or aspiration. In certain embodiments, the acoustic force is surface acoustic wave.

In certain embodiments, generating an electric actuation force includes generating an alternating current. In certain embodiments, the alternating current has a root mean squared (rms) voltage of 10 V or more. In certain other embodiments, the alternating current has a frequency in a radio frequency range.

In certain embodiments, the first liquid droplet is a polarizable liquid, the second liquid droplet is a polarizable liquid, the mixture is a polarizable liquid or both the first liquid droplet and second liquid droplet are each polarizable liquids.

In certain embodiments, the method further includes positioning the at least a portion of the mixture over the array of wells using an electric actuation force. In certain other embodiments, the method further includes positioning the at least a portion of the mixture over the array of wells using a capillary element configured to facilitate movement of the mixture to the array of wells.

In certain embodiments, the supports are magnetic solid supports. In certain other embodiments, when magnetic solid supports are used, an electric actuation force and a magnetic field are applied from opposite directions relative to the at least a portion of the mixture.

In certain embodiments, the method further includes mixing the mixture by moving the mixture back and forth, moving the mixture in a circular pattern, splitting the mixture into two or more submixtures and merging the submixtures.

In certain embodiments, the mixture is an aqueous liquid. In certain other embodiments, the mixture is an immiscible liquid. In certain other embodiments the liquid droplet is a hydrophobic liquid droplet. In certain embodiments, the array of wells has a hydrophilic surface. In certain other embodiments, the array of wells has a hydrophobic surface. In certain embodiments, the substrate includes a hydrophilic surface. In certain other embodiments, the substrate includes a hydrophobic surface. In certain embodiments, the method further includes generating an electric actuation force with a series of electrodes to move the mixture to the array of wells to seal the loaded wells.

In certain embodiments, one or more wells of the array are loaded with at least one solid support. In certain other embodiments, the loading includes applying a magnetic field to facilitate movement of at least one solid support into the one or more wells of the array. In certain other embodiments, the method further includes removing any solid supports that are not loaded into a well of the array after the loading. In certain other embodiments, the removing includes generating an electric actuation force with the series of electrodes to move a polarizable fluid droplet to the array of wells to move the at least a portion of the mixture to a distance from the array of wells. In certain other embodiments, the removing includes generating an electric actuation force with the series of electrodes to move an aqueous washing droplet across the array of wells.

In certain embodiments, the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

In certain embodiments, the measuring involves determining the total number of solid supports in the wells of an array. In certain embodiments, the measuring involves determining the number of solid supports in the wells of the array that contain the detectable label. In certain embodiments, the measuring involves subtracting the number of solid supports that contain a detectable label from the total number of solid supports in the wells of the array to determine the number of solid supports in the wells of the array that do not contain any detectable label. In certain embodiments, the measuring involves determining the ratio of solid supports that contain a detectable label to the number of solid supports that do not contain any detectable label.

Also disclosed herein is a method of loading wells with particles, including generating an electric field with a plurality of electrodes to move a liquid droplet containing microparticles to an array of wells, wherein one or more wells of the array of wells is of sufficient size to have loaded therein a particle; loading one or more wells with a particle; and generating an electric field with the plurality of electrodes to move a polarizable fluid droplet to the array of wells to seal the array of wells.

In some embodiments, the method further includes positioning the liquid droplet over the array of wells using the electric field. In some embodiments, the method further includes positioning the liquid droplet over the array of wells using a capillary element configured to facilitate movement of the liquid droplet to the array of wells. In some embodiments, the particle is a magnetic bead. In some embodiments, the loading includes applying a magnetic field to facilitate movement of the one or more magnetic beads into the one or more wells of the array. In some embodiments, the array of wells has a hydrophilic surface. In some embodiments, the array of wells has a hydrophobic surface. In some embodiments, the generating an electric field includes generating an alternating current. In certain embodiments, the alternating current has a root mean squared (rms) voltage of 10 V or more. In certain embodiments, the alternating current has a frequency in a radio frequency range.

Also disclosed herein is a method of forming a digital microfluidic and analyte detection device, including unwinding a first roll including a first substrate to position a first portion of the first substrate at a first position; forming a plurality of electrodes on the first portion of the first substrate at the first position; and forming an array of wells on a second portion of the first substrate at a second position.

In some embodiments, the method further includes unwinding the first roll to position the second portion adjacent the first portion of the first substrate at the second position prior to forming the array of wells. In some embodiments, the method further includes unwinding a second roll including a second substrate to position a third portion of the third substrate at a third position; and bonding the second substrate with the first substrate at the third position in a manner sufficient to position the second substrate spaced apart from the first substrate.

Also disclosed herein is a method of forming an integrated digital microfluidic and analyte detection device, including unwinding a first roll including a first substrate to position a first portion of the first substrate at a first position, forming a plurality of electrodes on the first portion of the first substrate at the first position; unwinding a second roll including a second substrate to position a second portion of the second substrate at a second position; forming an array of wells on the second portion at the second position; and bonding the second substrate with the first substrate in a manner sufficient to position the second substrate spaced apart from the first substrate; and position the second portion above the first portion, or above a third portion adjacent the first portion of the first substrate, wherein the array of wells faces the first substrate.

In some embodiments, the forming the array of wells includes using thermal or ultraviolet nanoimprint lithography, nanoimprint roller, laser ablation, or by bonding a prefabricated substrate including an array of wells onto the first portion of the first substrate. In some embodiments, the method further includes subjecting the first substrate to intense heat, pressure, or ultraviolet light to form phononic structures on or within the first substrate using a mold.

In some embodiments, the method further includes applying a hydrophobic and/or a dielectric material on electrodes of the series using a printer device. In some embodiments, the hydrophobic and/or dielectric material includes a curing material. In some embodiments, the method further includes applying heat or ultraviolet light to cure the applied hydrophobic and/or dielectric material. In some embodiments, the method further includes dicing the first and second substrates to generate a bonded substrates includes the first and second portions.

Also disclosed herein is a method of detecting an analyte of interest in a liquid droplet, including, providing a first liquid droplet including an analyte of interest; providing a second liquid droplet including a specific binding member and a labeled analyte, wherein the binding member is immobilized on at least one solid support, the specific binding member specifically binds to the analyte of interest, and the labeled analyte is an analyte of interest labeled with a detectable label; using energy to exert a force to manipulate the first liquid droplet with the second liquid droplet to create a mixture; and moving all or at least a portion of the mixture to an array of wells, wherein one or more wells of the array is of sufficient size to accommodate the at least one solid support.

Also disclosed herein is a method of detecting an analyte of interest in a liquid droplet, including providing a first liquid droplet including an analyte of interest; providing a second liquid droplet including an immobilized analyte and at least one specific binding member, wherein the immobilized analyte is an analyte of interest immobilized on at least one solid support, the at least one specific binding member specifically binds to the analyte of interest, and the at least one specific binding member is labeled with a detectable label; using energy to exert a force to manipulate the first liquid droplet with the second liquid droplet to create a mixture; moving all or at least a portion of the mixture to an array of wells, wherein one or more wells of the array is of sufficient size to accommodate the at least one solid support; and detecting the analyte of interest in the wells.

BRIEF DESCRIPTION OF THE DRAWINGS

FIG. 4A illustrates a side view of the device of FIG. 2A with a droplet containing particles/beads being moved onto an array of wells.

FIG. 4B illustrates a side view of the device of FIG. 2B with a droplet containing particles/beads being moved onto an array of wells with a droplet of an immiscible fluid.

FIG. 10 illustrates an example of assembling the top and bottom substrates to manufacture a plurality of digital microfluidic and analyte detection devices.

FIG. 13A illustrates a side view of one embodiment of the surface acoustic component of the integrated microfluidic and analyte device and array of wells.

FIG. 13B illustrates a side view of another embodiment of the surface acoustic component of the integrated microfluidic and analyte device and array of wells.

FIGS. 14A-14B illustrate an example of fabricating the sample preparation component and well array component.

FIG. 19 depicts a single flexible chip fabricated according to the schematic in FIG. 18.

FIG. 20 depicts actuation of droplets in a DMF chip, according to embodiments of the present disclosure.

FIG. 29 is a schematic showing components for DMF-directed top loading of microparticles into a well array, according to embodiments of the present disclosure.

FIGS. 30A-30D are a collection of schematic diagrams showing steps of a thyroid stimulating hormone (TSH) immunoassay using an integrated DMF-well device, according to embodiments of the present disclosure.

DETAILED DESCRIPTION OF THE INVENTION

Figure 1A:
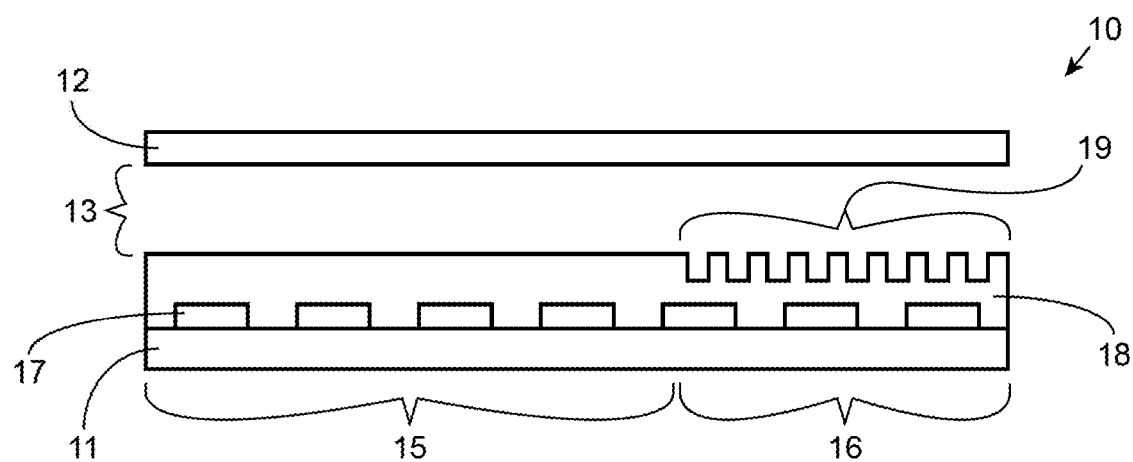
FIG. 1A illustrates a side view of an integrated digital microfluidic and analyte detection device according to one embodiment.

An integrated microfluidic and analyte detection device is disclosed. Also provided herein are exemplary methods for using an integrated microfluidic and analyte detection device and associated systems.

Before the present invention is described in greater detail, it is to be understood that this invention is not limited to a particular embodiment described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an" and "the" include plural referents unless the context clearly dictates otherwise. Thus, for example, refer to "an electrode" includes plurality of such electrodes and reference to "the well" includes reference to one or more wells and equivalents thereof known to those skilled in the art, and so forth.

All publications mentioned herein are incorporated herein by reference to disclose and describe the methods and/or materials in connection with which the publications are cited. The present disclosure is controlling to the extent there is a contradiction between the present disclosure and a publication incorporated by reference.

DETAILED DESCRIPTION

Embodiments of the present disclosure relate to methods, systems, and devices for analysis of analyte(s) in a sample. In certain embodiments, the sample may be a biological sample.

Definitions

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity" and "binding affinity" as used interchangeably herein refer to the tendency or strength of binding of the binding member to the analyte. For example, the binding affinity may be represented by the equilibrium dissociation constant ($K_D$), the dissociation rate ($k_d$), or the association rate ($k_a$).

"Analog" as used herein refers to a molecule that has a similar structure to a molecule of interest (e.g., nucleoside analog, nucleotide analog, sugar phosphate analog, analyte analog, etc.). An analyte analog is a molecule that is structurally similar to an analyte but for which the binding member has a different affinity.

The term "aptamer" as used herein refers to an oligonucleotide or peptide molecule that can bind to pre-selected targets including small molecules, proteins, and peptides among others with high affinity and specificity. Aptamers may assume a variety of shapes due to their propensity to form helices and single-stranded loops. An oligonucleotide or nucleic acid aptamer can be a single-stranded DNA or RNA (ssDNA or ssRNA) molecule. A peptide aptamer can include a short variable peptide domain, attached at both ends to a protein scaffold.

"Bead" and "particle" are used herein interchangeably and refer to a substantially spherical solid support.

"Component," "components," or "at least one component," refer generally to a capture antibody, a detection reagent or conjugate, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum, whole blood, tissue aspirate, or plasma sample, in accordance with the methods described herein and other methods known in the art. Some components can be in solution or lyophilized for reconstitution for use in an assay.

"Digital microfluidics (DMF)," "digital microfluidic module (DMF module)," or "digital microfluidic device (DMF device)" as used interchangeably herein refer to a module or device that utilizes digital or droplet-based microfluidic techniques to provide for manipulation of discrete and small volumes of liquids in the form of droplets. Digital microfluidics uses the principles of emulsion science to create fluid-fluid dispersion into channels (principally water-in-oil emulsion). It allows the production of monodisperse drops/bubbles or with a very low polydispersity. Digital microfluidics is based upon the micromanipulation of discontinuous fluid droplets within a reconfigurable network. Complex instructions can be programmed by combining the basic operations of droplet formation, translocation, splitting, and merging.

Digital microfluidics operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting which relies on the dependence of surface tension between a liquid droplet present on a surface and the surface on the electric field applied to the surface.

"Drag-tag" refers to a mobility modifier. The drag-tag may be genetically engineered, highly repetitive polypeptides ("protein polymers") that are designed to be large, water-soluble, and completely monodisperse. Positively charged arginines may be deliberately introduced at regular intervals into the amino acid sequence to increase the hydrodynamic drag without increasing drag-tag length. Drag-tags are described in U.S. Patent Publication No. 20120141997, which is incorporated herein by reference.

"Enzymatic cleavable sequence" as used herein refers to any nucleic acid sequence that can be cleaved by an enzyme. For example, the enzyme may be a protease or an endonuclease, such as a restriction endonuclease (also called restriction enzymes). Restriction endonucleases are capable of recognizing and cleaving a DNA molecule at a specific DNA cleavage site between predefined nucleotides. Some endonucleases, such as for example Fok1, comprise a cleavage domain that cleaves the DNA unspecifically at a certain position regardless of the nucleotides present at this position. In some embodiments, the specific DNA cleavage site and the DNA recognition site of the restriction endonuclease are identical.

"Globular protein" refers to a water soluble protein that has a roughly spherical shape. Examples of globular proteins include but are not limited to ovalbumin, beta-globulin, C-reactive protein, fibrin, hemoglobin, IgG, IgM, and thrombin.

"Label" or "detectable label" as used interchangeably herein refers to a moiety attached to a specific binding member or analyte to render the reaction between the specific binding member and the analyte detectable, and the specific binding member or analyte so labeled is referred to as "detectably labeled." A label can produce a signal that is detectable by visual or instrumental means. Various labels include: (i) a tag attached to a specific binding member or analyte by a cleavable linker; or (ii) signal-producing substance, such as chromagens, fluorescent compounds, enzymes, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

"Microparticle(s)(s)" and "microbead(s)" are used interchangeably herein and refer to a microbead or microparticle that is allowed to occupy or settle in an array of wells, such as, for example, in an array of wells in a detection module. The microparticle and microbead may contain at least one specific binding member that binds to an analyte of interest and at least one detectable label. Alternatively, the microparticle and microbead may containing a first specific binding member that binds to the analyte and a second specific binding member that also binds to the analyte and contains at least one detectable label.

"Nucleobase" or "base" means those naturally occurring and synthetic heterocyclic moieties commonly known in the art of nucleic acid or polynucleotide technology or peptide nucleic acid technology for generating polymers. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Nucleobases can be linked to other moieties to form nucleosides, nucleotides, and nucleoside/tide analogs.

"Nucleoside" refers to a compound consisting of a purine, deazapurine, or pyrimidine nucleobase, e.g., adenine, guanine, cytosine, uracil, thymine, 7-deazaadenine, 7-deazaguanosine, that is linked to the anomeric carbon of a pentose sugar at the 1' position, such as a ribose, 2'-deoxyribose, or a 2',3'-di-deoxyribose.

"Nucleotide' as used herein refers to a phosphate ester of a nucleoside, e.g., a mono-, a di-, or a triphosphate ester, wherein the most common site of esterification is the hydroxyl group attached to the C-5 position of the pentose.

"Nucleobase polymer" or "nucleobase oligomer" refers to two or more nucleobases that are connected by linkages to form an oligomer. Nucleobase polymers or oligomers include, but are not limited to, poly- and oligonucleotides (e.g., DNA and RNA polymers and oligomers), poly- and oligo-nucleotide analogs and poly- and oligonucleotide mimics, such as polyamide or peptide nucleic acids. Nucleobase polymers or oligomers can vary in size from a few nucleobases to several hundred nucleobases or to several thousand nucleobases. The nucleobase polymers or oligomers may include from about 2 to 100 nucleobases or from about 8000 to 10000 nucleobases. For example, the nucleobase polymers or oligomers may have at least about 2 nucleobases, at least about 5 nucleobases, at least about 10 nucleobases, at least about 20 nucleobases, at least about 30 nucleobases, at least about 40 nucleobases, at least about 50 nucleobases, at least about 60 nucleobases, at least about 70 nucleobases, at least about 80 nucleobases, at least about 90 nucleobases, at least about 100 nucleobases, at least about 200 nucleobases, at least about 300 nucleobases, at least about 400 nucleobases, at least about 500 nucleobases, at least about 600 nucleobases, at least about 700 nucleobases, at least about 800 nucleobases, at least about 900 nucleobases, at least about 1000 nucleobases, at least about 2000 nucleobases, at least about 3000 nucleobases, at least about 4000 nucleobases, at least about 5000 nucleobases, at least about 6000 nucleobases, at least about 7000 nucleobases, at least about 8000 nucleobases, at least about 9000 nucleobases, or at least about 10000 nucleobases.

"Polymer brush" refers to a layer of polymers attached with one end to a surface. The polymers are close together and form a layer or coating that forms its own environment. The brushes may be either in a solvent state, when the dangling chains are submerged into a solvent, or in a melt state, when the dangling chains completely fill up the space available. Additionally, there is a separate class of polyelectrolyte brushes, when the polymer chains themselves carry an electrostatic charge. The brushes may be characterized by the high density of grafted chains. The limited space then leads to a strong extension of the chains, and unusual properties of the system. Brushes may be used to stabilize colloids, reduce friction between surfaces, and to provide lubrication in artificial joints "Polynucleotides" or "oligonucleotides" refer to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof. The term nucleic acid encompasses the terms polynucleotide and oligonucleotides and includes single stranded and double stranded polymers of nucleotide monomers.

"Polynucleotide analog" or "oligonucleotide analog" refers to nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. Nos. 6,013,785 and 5,696,253.

"Receptor" as used herein refers to a protein-molecule that recognizes and responds to endogenous-chemical signals. When such endogenous-chemical signals bind to a receptor, they cause some form of cellular/tissue-response. Examples of receptors include, but not limited to, neural receptors, hormonal receptors, nutrient receptors, and cell surface receptors.

As used herein, "spacer" refers to a chemical moiety that extends the cleavable group from the specific binding member, or which provides linkage between the binding member and the support, or which extends the label/tag from the photocleavable moiety. In some embodiments, one or more spacers may be included at the N-terminus or C-terminus of a polypeptide or nucleotide-based tag or label in order to distance optimally the sequences from the specific binding member. Spacers may include but are not limited to 6-aminocaproic acid, 6-aminohexanoic acid; 1,3-diamino propane; 1,3-diamino ethane; polyethylene glycol (PEG) polymer groups and short amino acid sequences, such as polyglycine sequences, of 1 to 5 amino acids.

"Specific binding partner" or "specific binding member" as used interchangeably herein refer to one of two different molecules that specifically recognizes the other molecule compared to substantially less recognition of other molecules. The one of two different molecules has an area on the surface or in a cavity, which specifically binds to and is thereby defined as complementary with a particular spatial and polar organization of the other molecule. The molecules may be members of a specific binding pair. For example, a specific binding member may include, but not limited to, a protein, such as a receptor, an enzyme, an antibody and an aptamer, a peptide a nucleotide, oligonucleotide, a polynucleotide and combinations thereof.

As used herein, "tag" or "tag molecule" both refer to the molecule (e.g., cleaved from the second binding member dissociated from the target analyte) that is used to provide an indication of the level of analyte in a sample. These terms refer to a single tag molecule or a plurality of the same tag molecule. Likewise "tags", unless specified otherwise, refers to one or one or more tags.

"Tracer" as used herein refers to an analyte or analyte fragment conjugated to a tag or label, wherein the analyte conjugated to the tag or label can effectively compete with the analyte for sites on an antibody specific for the analyte. For example, the tracer may be an analyte or analog of the analyte, such as cyclosporine or its analog ISA247, vitamin D and its analogs, sex hormones and their analogs, etc.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety to disclose and describe the methods and/or materials in connection with which the publications are cited. The materials, methods, and examples disclosed herein are illustrative only and not intended to be limiting.

Methods for Analyte Analysis

Provided herein are methods for analyte analysis. The method may involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Provided herein are methods for detecting an analyte of interest in liquid droplet (wherein the analyte of interest is from a test or biological sample). The method includes providing a first liquid droplet containing an analyte of interest, providing a second liquid droplet containing at least one solid support (such as, for example, a magnetic solid support (such as a bead)) which contains a specific binding member that binds to the analyte of interest, using energy to exert a force to manipulate the first liquid droplet (which contains the analyte of interest) with the second liquid (containing the at least one solid support) to create a mixture, moving all or at least a portion of the mixture to an array of wells (where one or more wells of the array are of sufficient size to accommodate the at least one solid support), adding at least one detectable label to the mixture before, after or both before or after moving a portion of the mixture to the array of wells and detecting the analyte of interest in the wells. In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, if magnetic solid supports are used, an electric actuation force and a magnetic field can be applied and applied from opposition directions, relative to the at least a portion of the mixture. In certain other embodiments, the mixture is mixed by moving it: back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the at least one solid support into the array of wells. In certain embodiments, a magnetic field is used to facilitate movement of the mixture and thus, at least one solid support, into one or more wells of the array. In certain embodiments, after the at least one solid supports are loaded into the wells, any solid supports that are not loaded into a well can be removed using routine techniques known in the art. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove the solid supports not bound to any analyte of interest. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method have a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the at least one solid support comprises at least one binding member that specifically binds to the analyte of interest. In certain embodiments, the detectable label is added to the mixture before moving at least a portion of the mixture to the array of wells. In certain other embodiments, the detectable label is added to the mixture after the moving of at least a portion of the analyte of interest. In certain embodiments, the detectable label comprises at least one binding member that specifically binds to the analyte of interest. In certain embodiments, the detectable label comprises a chromagen, a florescent compound, an enzyme, a chemiluminescent compound or a radioactive compound. In certain embodiments, the binding member is a receptor, aptamer or antibody. In certain embodiments, the method further comprises positioning the at least a portion of the mixture over the array of wells using a capillary element configured to facilitate movement of the mixture to the array of wells.

In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, method described herein is performed using a Robotics based assay processing unit.

Provided herein are methods for detecting an analyte of interest in liquid droplet (wherein the analyte of interest is from a test or biological sample). The method includes providing a first liquid droplet containing an analyte of interest, providing a second liquid droplet containing at least one detectable label which contains a specific binding member that binds to the analyte of interest, using energy to exert a force to manipulate the first liquid droplet (which contains the analyte of interest) with the second liquid (containing the at least one solid support) to create a mixture (namely, an analyte/detectable label-specific binding member complex), moving all or at least a portion of the mixture to an array of wells (where one or more wells of the array are of sufficient size to accommodate the at least one solid support) and detecting the analyte of interest in the wells. In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, the mixture is mixed by moving it: back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the an analyte/detectable label-specific binding member complex into the array of wells. In certain embodiments, a magnetic field is used to facilitate movement of the mixture and thus, at least one an analyte/detectable label-specific binding member complex into one or more wells of the array. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove any detectable label-specific binding members not bound to any analyte. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method have a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the detectable label is bound to at least one solid support. In certain embodiments, the detectable label comprises a chromagen, a florescent compound, an enzyme, a chemiluminescent compound or a radioactive compound. In certain embodiments, the binding member is a receptor, aptamer or antibody. In certain embodiments, the method further comprises positioning the at least a portion of the mixture over the array of wells using a capillary element configured to facilitate movement of the mixture to the array of wells.

In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, method described herein is performed using a Robotics based assay processing unit.

Provided herein are methods for measuring an analyte of interest in liquid droplet (wherein the analyte of interest is from a test or biological sample). The method includes providing a first liquid droplet containing an analyte of interest, providing a second liquid droplet containing at least one solid support (such as, for example, a magnetic solid support (such as a bead)) which contains a specific binding member that binds to the analyte of interest, using energy to exert a force to manipulate the first liquid droplet (which contains the analyte of interest) with the second liquid (containing the at least one solid support) to create a mixture, moving all or at least a portion of the mixture to an array of wells (where one or more wells of the array are of sufficient size to accommodate the at least one solid support), adding at least one detectable label to the mixture before, after or both before or after moving a portion of the mixture to the array of wells and measuring the analyte of interest in the wells. In certain embodiments, "using energy to exert a force to manipulate the first liquid droplet with the second liquid droplet" refers to the use of non-mechanical forces (namely, for example, energy created without the use of pumps and/or valves) to provide or exert a force that manipulates (such as merges or combines) at least the first and second liquid droplets (and optionally, additional droplets) into a mixture. Example of non-mechanical forces that can be used in the methods described herein include electric actuation force (such as droplet actuation, electrophoresis, electrowetting, dielectrophoresis, electrostatic actuation, electric field mediated, electrode mediated, capillary force, chromatography, centrifugation or aspiration) and/or acoustic force (such as surface acoustic wave (or "SAW"). In certain embodiments, the electric actuation force generated is an alternating current. For example, the alternating current can have a root mean squared (rms) voltage of 10 V, 15 V, 20 V, 25 V, 30 V, 35V or more. For example, such alternating current can have a rms voltage of 10 V or more, 15 V or more, 20 V or more, 25 V or more, 30 V or more or 35 V or more. Alternatively, the alternating current can have a frequency in a radio frequency range.

In certain embodiments, if magnetic solid supports are used, an electric actuation force and a magnetic field can be applied and applied from opposition directions, relative to the at least a portion of the mixture. In certain other embodiments, the mixture is mixed by moving it: back and forth, in a circular pattern or by splitting it into two or more submixtures and then merging the submixtures. In certain other embodiments, an electric actuation force can be generated using a series or plurality of electrodes (namely, at least two or more, at least three or more, at least four or more, at least five or more, at least six or more, at least seven or more, at least eight or more, at least nine or more, at least ten or more, at least eleven or more, at least twelve or more, at least thirteen or more, at least fourteen or more, at least fifteen or more, etc.) to move the mixture to the array of wells in order to seal the wells (which are loaded with at least one solid support).

In certain embodiments, the moving of all or at least a portion of the mixture to an array of wells results in the loading (filling and/or placement) of the at least one solid support into the array of wells. In certain embodiments, a magnetic field is used to facilitate movement of the mixture and thus, at least one solid support, into one or more wells of the array. In certain embodiments, after the at least one solid supports are loaded into the wells, any solid supports that are not loaded into a well can be removed using routine techniques known in the art. For example, such removing can involve generating an electric actuation force (such as that described previously herein) with a series or plurality of electrodes to move a fluid droplet (such as a polarizable fluid droplet) to the array of wells to move at least a portion of the mixture to a distance (the length of which is not critical) from the array of wells. In certain embodiments, an aqueous washing liquid can be used to remove the solid supports not bound to any analyte of interest. In such embodiments, the removal involves generating an electric actuation force with a series or plurality of electrodes to move an aqueous wash (or washing) droplet (a third droplet) across the array of wells. The amount and type of aqueous liquid used for said washing is not critical.

In certain embodiments, the mixture in the method is an aqueous liquid. In other embodiments, the mixture is an immiscible liquid. In other embodiments, the liquid droplet is a hydrophobic liquid droplet. In other embodiments, the liquid droplet is a hydrophilic liquid droplet. In certain embodiments, the array of wells used in the method have a hydrophobic surface. In other embodiments, the array of wells has a hydrophilic surface.

In certain embodiments, the first liquid droplet used in the method is a polarizable liquid. In certain embodiments, the second liquid droplet used in the method is a polarizable liquid. In certain embodiments, the first and second liquid droplets used in the method are polarizable liquids. In certain embodiments, the mixture is a polarizable liquid. In certain embodiments one or more of the first droplet, second droplet and mixture is a polarizable liquid.

In certain embodiments, the at least one solid support comprises at least one binding member that specifically binds to the analyte of interest. In certain embodiments, the detectable label is added to the mixture before moving at least a portion of the mixture to the array of wells. In certain other embodiments, the detectable label is added to the mixture after the moving of at least a portion of the analyte of interest to the array of wells. In certain embodiments, the detectable label comprises at least one binding member that specifically binds to the analyte of interest. In certain embodiments, the detectable label comprises a chromagen, a florescent compound, an enzyme, a chemiluminescent compound or a radioactive compound. In certain embodiments, the binding member is a receptor, aptamer or antibody. In certain embodiments, the method further comprises positioning the at least a portion of the mixture over the array of wells using a capillary element configured to facilitate movement of the mixture to the array of wells.

In certain embodiments, the method described herein is performed using a microfluidics device. In certain embodiments, the method described herein is performed using a digital microfluidics device (DMF). In certain embodiments, method described herein is performed using a surface acoustic wave based microfluidics device (SAW). In certain embodiments, method described herein is performed using an integrated DMF and analyte detection device. In certain embodiments, method described herein is performed using an integrated surface acoustic wave based microfluidic device and analyte detection device. In certain embodiments, method described herein is performed using a Robotics based assay processing unit.

In certain embodiments, the measuring first involves determining the total number of solid supports in the well of the array ("total solid support number"). Next, the number of solid supports in the wells of the array that contain the detectable label are determined, such as, for example, determining the intensity of the signal produced by the detectable label ("positives"). The positives are subtracted from the total solid support number to provide the number of solid supports in the array of wells that do not contain a detectable label or are not detected ("negatives"). Then, the ratio of positives to negatives in the array of wells can be determined and then compared to a calibration curve. Alternatively, digital quantitation using the Poisson equation P(x; μ) as shown below:

$$P(x;\mu)=(e^{-\mu})(\mu^x)/x!$$

where:

e: A is a constant equal to approximately 2.71828,

μ: ix ghd mean number of successes that occur in a specified region, and x: is the tactual number of successes that occur in a specified region.

The sample may be any test sample containing or suspected of containing an analyte of interest. As used herein, "analyte", "target analyte", "analyte of interest" are used interchangeably and refer to the analyte being measured in the methods and devices disclosed herein. Analytes of interest are further described below.

"Contacting" and grammatical equivalents thereof as used herein refer to any type of combining action which brings a binding member into sufficiently close proximity with the analyte of interest in the sample such that a binding interaction will occur if the analyte of interest specific for the binding member is present in the sample. Contacting may be achieved in a variety of different ways, including combining the sample with a binding member, exposing a target analyte to a binding member by introducing the binding member in close proximity to the analyte, and the like.

In certain cases, the first binding member may be immobilized on a solid support. As used herein, the term "immobilized" refers to a stable association of the first binding member with a surface of a solid support. By "stable association" is meant a physical association between two entities in which the mean half-life of association is one day or more, e.g., under physiological conditions. In certain aspects, the physical association between the two entities has a mean half-life of two days or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

The solid support having a surface on which the binding reagent is immobilized may be any convenient surface in planar or non-planar conformation, such as a surface of a microfluidic chip, an interior surface of a chamber, an exterior surface of a bead (as defined herein), or an interior and/or exterior surface of a porous bead. For example, the first binding member may be attached covalently or non-covalently to a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. In certain embodiments, the bead may be a magnetic nanobead, nanoparticle, microbead or microparticle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first binding member is immobilized may be stored in dry form or in a liquid. The magnetic beads may be subjected to a magnetic field prior to or after contacting with the sample with a magnetic bead on which the first binding member is immobilized.

After the contacting step, the sample and the first binding member may be incubated for a sufficient period of time to allow for the binding interaction between the binding member and analyte to occur. In addition, the incubating may be in a binding buffer that facilitates the specific binding interaction. The binding affinity and/or specificity of the first binding member and/or the second binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer.

The binding affinity and/or specificity of the first binding member and/or the second binding member may be measured using the disclosed methods and device described below. In some embodiments, the one aliquot of sample is assayed using one set of conditions and compared to another aliquot of sample assayed using a different set of conditions, thereby determining the effect of the conditions on the binding affinity and/or specificity. For instance, changing or altering the condition can be one or more of removing the target analyte from the sample, adding a molecule that competes with the target analyte or the ligand for binding, and changing the pH, salt concentration, or temperature. Additionally or alternatively, a duration of time can be the variable and changing the condition may include waiting for a duration of time before again performing the detection methods.

The binding buffer may include molecules standard for antigen-antibody binding buffers such as, albumin (e.g., BSA), non-ionic detergents (Tween-20, Triton X-100), and/or protease inhibitors (e.g., PMSF). In certain cases, the binding buffer may be added to the microfluidic chip, chamber, etc., prior to or after adding the sample. In certain cases, the first binding member may be present in a binding buffer prior to contacting with the sample. The length of time for binding interaction between the binding member and analyte to occur may be determined empirically and may depend on the binding affinity and binding avidity between the binding member and the analyte. In certain embodiments, the contacting or incubating may be for a period of 5 sec to 1 hour, such as, 10 sec-30 minutes, or 1 minute-15 minutes, or 5 minutes-10 minutes, e.g., 10 sec, 15 sec, 30 sec, 1 minute, 5 minutes, 10 minutes, 15 minutes, 30 minutes, 45 minutes, 1 hour or 2 hours. Other conditions for the binding interaction, such as, temperature, salt concentration, may also be determined empirically or may be based on manufacturer's instructions. For example, the contacting may be carried out at room temperature (21° C.-28° C., e.g., 23° C.-25° C.), 37° C., or 4° C. In certain embodiments, an optional mixing of the sample with the first binding member may be carried out during the contacting step.

Following complex formation between the immobilized first binding member and the analyte, any unbound analyte may be removed from the vicinity of the first binding member along with the sample while the complex of the first binding member and the analyte may be retained due to its association with the solid support. Optionally, the solid support may be contacted with a wash buffer to remove any molecules non-specifically bound to the solid support.

After the first contacting step, and the optional removal of sample and/or optional wash steps, the complex of the first binding member and the analyte may be contacted with a second binding member, thereby leading to the formation of a sandwich complex in which the analyte is bound by the two binding members. An optional mixing of the second binding member with the first binding member-analyte complex may be carried out during the second contacting step. In some embodiments, immobilization of the analyte molecules with respect to a surface may aid in removal of any excess second binding members from the solution without concern of dislodging the analyte molecule from the surface. In some embodiments, the second binding member may include a detectable label comprising one or more signal-producing substances, such as chromagens, fluorescent compounds, chemiluminescent compounds, enzymes, radioactive compounds, and the like.

As noted above, the second contacting step may be carried out in conditions sufficient for binding interaction between the analyte and the second binding member. Following the second contacting step, any unbound second binding member may be removed, followed by an optional wash step. Any unbound second binding member may be separated from the complex of the first binding member-analyte-second binding member by a suitable means such as, droplet actuation, electrophoresis, electrowetting, dielectrophoresis, electrostatic actuation, electric field mediated, electrode mediated, capillary force, chromatography, centrifugation, aspiration or SAW. Upon removal of any unbound second binding member from the vicinity of the complex of the first binding member-analyte-second binding member, the detectable label attached to the second binding member present in the complex of the first binding member-analyte-second binding member may be separated by a suitable means or may be detected using techniques known in the art. In some embodiments, the detectable label comprises a detectable label comprising one or more signal-producing substances, such as chromagens, fluorescent compounds, enzymes, chemiluminescent compounds, radioactive compounds, and the like. Alternatively, in some embodiments, if the detectable label comprises a tag, the tag can be cleaved or disassociated from the complex which remains after removal of unbound reagents. For example, the tag may be attached to the second binding member via a cleavable linker ("cleavable linker" as described herein). The complex of the first binding member-analyte-second binding member may be exposed to a cleavage agent that mediates cleavage of the cleavable linker.

As noted herein, the tag may include a nucleic acid. In certain embodiments, the quantification of the analyte does not include determining the identity of the tag by determining identity of at least a portion of the nucleic acid sequence present in the tag. For example, the counting step may not include determining a sequence of the tag. In other embodiments, the tag may not be sequenced, however, identity of the tag may be determined to the extent that one tag may be distinguished from another tag based on a differentiable signal associated with the tag due its size, conformation, charge, amount of charge and the like. Identification of tag may be useful in methods involving simultaneous analysis of a plurality of different analytes in a sample, for example, two, three, four, or more different analytes in a sample.

In certain embodiments, the simultaneous analysis of multiple analytes in a single sample may be performed by using a plurality of different first and second binding members where a pair of first and second binding members is specific to a single analyte in the sample. In these embodiments, the detectable label associated with the second binding member of a first pair of first and second binding members specific to a single analyte may be distinguishable from the detectable label associated with the second binding member of a second pair of first and second binding members specific to a different analyte. As noted above, a first detectable label may be distinguishable from second detectable label based on difference in signal-producing substances, etc.

In some embodiments, the concentration of an analyte in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less.

In some cases, the limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less.

The upper limit of detection (e.g., the upper concentration of an analyte which may be determined in solution) is at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 µM, at least about 100 µM, at least about 1000 µM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

In certain embodiments, at least some steps of the methods described herein may be carried out on a digital integrated microfluidics and analyte detection device, such as the device described herein. In certain embodiments, the methods of the present disclosure are carried out using a digital integrated microfluidics device in conjunction with an analyte detection device. For example, the digital microfluidics device and the analyte detection device may be separate devices and a droplet containing the detectable label may be generated in the microfluidics device and transported to the analyte detection device.

In certain embodiments, the methods of the present disclosure are carried out using a device in which a digital microfluidics module is integrated with an analyte detection device, such as the device described below. In certain embodiments, the digital integrated microfluidics module and the analyte detection device may be reversibly integrated. For example, the two modules may be combined physically to form the integrated device and which device could then be separated into the individual modules. In certain embodiments, the methods of the present disclosure are carried out using a disposable cartridge that includes a microfluidics module with a built-in analyte detection device. Exemplary embodiments of the devices used for performing the methods provided herein are described further in the next section.

Exemplary embodiments of the present method include merging a sample droplet containing an analyte of interest with a droplet containing a first binding member that binds to the analyte of interest and that may be immobilized on a solid support (such as magnetic particles or beads). The single merged droplet can be incubated for a period of time sufficient to allow binding of the first binding member to the analyte of interest. Optionally, the single droplet may be agitated to facilitate mixing of the sample with the first binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away and replaced with a droplet containing a second binding member, which second binding member can optionally contain a detectable label. An optional wash step may be performed, prior to adding the second binding member, by moving a droplet of wash buffer to the location at which the beads are retained using the magnetic force. After a period of time sufficient for the second binding member to bind the analyte bound to the first binding member, the droplet containing the second binding member may be moved away while the beads are retained at the first location. The beads may be washed using a droplet of wash buffer. Following the wash step, the magnetic force may be removed and the droplet containing labeled beads (containing the first specific binding member/analyte/second specific binding member—an optional detectable label) are moved to a detection module such as that described herein. The labeled beads are allowed to settle into an array of wells in the detection module. The beads may settle via gravitational force or by applying electric or magnetic force. Following a wash step to remove any beads not located inside the wells, the wells may be sealed using a hydrophobic liquid. In the above embodiments, optionally, after the combining, a droplet may be manipulated (e.g., moved back and forth, moved in a circular direction, oscillated, split/merged, exposed to SAW, etc.) to facilitate mixing of the sample with the assay reagents, such as, the first binding member, second binding member, etc. In embodiments where the detectable label is an enzyme, a substrate can be added either before or after moving the complex is moved to the array of wells.

The moving of the droplets in the integrated microfluidic and analyte detection device may be carried out using electrical force (e.g., electrowetting, dielectrophoresis, electrode-mediated, opto-electrowetting, electric-field mediated, and electrostatic actuation) pressure, surface acoustic waves and the like. The force used for moving the droplets may be determined based on the specifics of the device, which are described in the following sections, and for the particular device described herein.

Multiplexing

The methods may include one or more (or alternately two or more) specific binding members to detect one or more (or alternately two or more) target analytes in the sample in a multiplexing assay. Each of the one or more (or alternately two or more) specific binding members binds to a different target analyte and each specific binding member is labeled with a different detectable label. For example, a first specific binding member binds to a first target analyte, a second specific binding member binds to a second target analyte, a third specific binding member binds to a third target analyte, etc. and the first specific binding member is labeled with a detectable label, the second specific binding member is labeled with a second detectable label, the third specific binding member is labeled with a third detectable label, etc. For example the first, second and third detectable labels can each have a different color. Alternatively, different types of labels can be used, such as, for example, the first label is an enzymatic label, the second label is a chromagen and the third label is a chemiluminescent compound.

Exemplary Target Analytes

As will be appreciated by those in the art, any analyte that can be specifically bound by a first and second binding member, may be detected and, optionally, quantified using methods and devices of the present disclosure.

In some embodiments, the analyte may be a biomolecule. Non-limiting examples of biomolecules include macromolecules such as, proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, or the like.

In certain embodiments, the analyte may be a post-translationally modified protein (e.g., phosphorylated, methylated, glycosylated protein) and the first or the second binding member may be an antibody specific to a post-translational modification. A modified protein may be bound to a first binding member immobilized on a solid support where the first binding member binds to the modified protein but not the unmodified protein. In other embodiments, the first binding member may bind to both the unmodified and the modified protein, and the second binding member may be specific to the post-translationally modified protein.

In some embodiments, the analyte may be a cell, such as, circulating tumor cell, pathogenic bacteria, viruses (including retroviruses, herpesviruses, adenoviruses, lentiviruses, Filoviruses (ebola), hepatitis viruses (e.g., A, B, C, D, and E); HPV etc.); spores; etc.

A non-limiting list of analytes that may be analyzed by the methods presented herein include Aβ42 amyloid beta-protein, fetuin-A, tau, secretogranin II, prion protein, Alpha-synuclein, tau protein, neurofilament light chain, parkin, PTEN induced putative kinase 1, DJ-1, leucine-rich repeat kinase 2, mutated ATP13A2, Apo H, ceruloplasmin, Peroxisome proliferator-activated receptor gamma coactivator-1 alpha (PGC-1α), transthyretin, Vitamin D-binding Protein, proapoptotic kinase R (PKR) and its phosphorylated PKR (pPKR), CXCL13, IL-12p40, CXCL13, IL-8, Dkk-3 (semen), p14 endocan fragment, Serum, ACE2, autoantibody to CD25, hTERT, CAI25 (MUC 16), VEGF, sIL-2, Osteopontin, Human epididymis protein 4 (HE4), Alpha-Fetoprotein, Albumin, albuminuria, microalbuminuria, neutrophil gelatinase-associated lipocalin (NGAL), interleukin 18 (IL-18), Kidney Injury Molecule-1 (KIM-1), Liver Fatty Acid Binding Protein (L-FABP), LMP1, BARFI, IL-8, carcinoembryonic antigen (CEA), BRAF, CCNI, EGRF, FGF19, FRS2, GREB1, and LZTS1, alpha-amylase, carcinoembryonic antigen, CA 125, IL8, thioredoxin, beta-2 microglobulin levels—monitor activity of the virus, tumor necrosis factor-alpha receptors—monitor activity of the virus, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin β15, insulin, plasma C-peptide, glycosylated hemoglobin (HBA1c), C-Reactive Protein (CRP), Interleukin-6 (IL-6), ARHGDIB (Rho GDP-dissociation inhibitor 2), CFL1 (Cofilin-1), PFN1 (profilin-1), GSTP1 (Glutathione S-transferase P), S100A11 (Protein S100-A11), PRDX6 (Peroxiredoxin-6), HSPE1 (10 kDa heat shock protein, mitochondrial), LYZ (Lysozyme C precursor), GPI (Glucose-6-phosphate isomerase), HIST2H2AA (Histone H2A type 2-A), GAPDH (Glyceraldehyde-3-phosphate dehydrogenase), HSPG2 (Basement membrane-specific heparan sulfate proteoglycan core protein precursor), LGALS3BP (Galectin-3-binding protein precursor), CTSD (Cathepsin D precursor), APOE (Apolipoprotein E precursor), IQGAPI (Ras GTPase-activating-like protein IQGAP), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAPI, NRG1, ESR1, ESR2, PGR, CDKNIB, MAP2K1, NEDD4-1, FOXO3A, PPPIRIB, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER aka RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm's Tumor-1 protein, Aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin IL, *Clostridium difficile* toxins A and B, etc.

Samples

As used herein, "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, fluid samples e.g. water supplies, etc.), an animal, e.g., a mammal, a plant, or any combination thereof. In a particular example, the source of an analyte is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of an analyte molecule is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

In certain embodiments, the analyte is not amplified (i.e., the copy number of the analyte is not increased) prior to the measurement of the analyte. For example, in cases where the analyte is DNA or RNA, the analyte is not replicated to increase copy numbers of the analyte. In certain cases, the analyte is a protein or a small molecule.

Specific Binding Members

As will be appreciated by those in the art, the binding members will be determined by the analyte to be analyzed. Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, F(ab')$_2$ fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., Journal of Biomolecular Screening, 14:77-85 (2009)), recombinant VHH single-domain antibodies, and $V_{NAR}$ fragments, disulfide-linked Fvs ("sdFv"), and anti-idiotypic ("anti-Id") antibodies, and functionally active epitope-binding fragments of any of the above, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second binding member may be a scaffold protein (e.g., lipocalins) or a receptor. In some cases, binding member for protein analytes may be a peptide. For example, when the target analyte is an enzyme, suitable binding members may include enzyme substrates and/or enzyme inhibitors which may be a peptide, a small molecule and the like. In some cases, when the target analyte is a phosphorylated species, the binding members may comprise a phosphate-binding agent. For example, the phosphate-binding agent may comprise metal-ion affinity media such as those describe in U.S. Pat. No. 7,070,921 and U.S. Patent Application No. 20060121544.

In certain cases, at least one of the binding members may be an aptamer, such as those described in U.S. Pat. Nos. 5,270,163, 5,475,096, 5,567,588, 5,595,877, 5,637,459, 5,683,867, 5,705,337. Nucleic acid aptamers (e.g., single-stranded DNA molecules or single-stranded RNA molecules) may be developed for capturing virtually any target molecule. Aptamers bind target molecules in a highly specific, conformation-dependent manner, typically with very high affinity, although aptamers with lower binding affinity can be selected. Aptamers may distinguish between target analyte molecules based on very small structural differences such as the presence or absence of a methyl or hydroxyl group and certain aptamers can distinguish between D- and L-enantiomers and diastereomers. Aptamers may bind small molecular targets, including drugs, metal ions, and organic dyes, peptides, biotin, and proteins. Aptamers can retain functional activity after biotinylation, fluorescein labeling, and when attached to glass surfaces and microspheres.

Nucleic acid aptamers are oligonucleotides that may be single stranded oligodeoxynucleotides, oligoribonucleotides, or modified oligodeoxynucleotide or oligoribonucleotides. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl;

2'-fluoro-; 2'-halo or 2-azido-ribose, carbocyclic sugar analogues a-anomeric sugars; epimeric sugars such as arabinose, xyloses or lyxoses, pyranose sugars, furanose sugars, and sedoheptulose.

Peptide aptamers may be designed to interfere with protein interactions. Peptide aptamers may be based on a protein scaffold onto which a variable peptide loop is attached, thereby constraining the conformation of the aptamer. In some cases, the scaffold portion of the peptide aptamer is derived from Bacterial Thioredoxin A (TrxA).

When the target molecule is a carbohydrate, potentially suitable capture components (as defined herein) include, for example, antibodies, lectins, and selectins. As will be appreciated by those of ordinary skill in the art, any molecule that can specifically associate with a target molecule of interest may potentially be used as a binding member.

For certain embodiments, suitable target analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, the first binding member may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s).

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; polymer brushes, and nucleic acids, such as salmon sperm DNA.

Certain embodiments utilize binding members that are proteins or polypeptides. As is known in the art, any number of techniques may be used to attach a polypeptide to a wide variety of solid supports. A wide variety of techniques are known to add reactive moieties to proteins, for example, the method outlined in U.S. Pat. No. 5,620,850. Further, methods for attachment of proteins to surfaces are known, for example, see Heller, Acc. Chem. Res. 23:128 (1990).

As explained herein, binding between the binding members and the analyte, is specific, e.g., as when the binding member and the analyte are complementary parts of a binding pair. In certain embodiments, the binding member binds specifically to the analyte. By "specifically bind" or "binding specificity" it is meant that the binding member binds the analyte molecule with specificity sufficient to differentiate between the analyte molecule and other components or contaminants of the test sample. For example, the binding member, according to one embodiment, may be an antibody that binds specifically to an epitope on an analyte.

The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the first binding member may be an antigen and the second binding member may be a secondary antibody that specifically binds to the target antibody or the first binding member may be a secondary antibody that specifically binds to the target antibody and the second binding member may be an antigen.

In some embodiments, the binding member may be chemically programmed antibodies (cpAbs) (described in Rader (2014) Trends in Biotechnology 32:186-197), bispecific cpAbs, antibody-recruiting molecules (ARMs) (described in McEnaney et al. (2012) ACS Chem. Biol. 7:1139-1151), branched capture agents, such as a triligand capture agent (described in Millward et al. (2011) J. Am. Chem. Soc. 133:18280-18288), engineered binding proteins derived from non-antibody scaffolds, such as monobodies (derived from the tenth fibronectin type III domain of human fibronectin), affibodies (derived from the immunoglobulin binding protein A), DARPins (based on Ankyrin repeat modules), anticalins (derived from the lipocalins bilin-binding protein and human lipocalin 2), and cysteine knot peptides (knottins) (described in Gilbreth and Koide, (2012) Current Opinion in Structural Biology 22:1-8; Banta et al. (2013) Annu. Rev. Biomed. Eng. 15:93-113), WW domains (described in Patel et al. (2013) Protein Engineering, Design & Selection 26(4):307-314), repurposed receptor ligands, affitins (described in Behar et al. (2013) 26:267-275), and/or Adhirons (described in Tiede et al. (2014) Protein Engineering, Design & Selection 27:145-155).

According to one embodiment in which an analyte is a biological cell (e.g., mammalian, avian, reptilian, other vertebrate, insect, yeast, bacterial, cell, etc.), the binding members may be ligands having specific affinity for a cell surface antigen (e.g., a cell surface receptor). In one embodiment, the binding member may be an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell, the bound cell may then be detected by using a second binding member that may be the same as the first binding member or may bind to a different molecule expressed on the surface of the cell.

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

Detectable Labels: Tars and Signal-Producing Substances

The methods described herein may include a specific binding member bound to a detectable label, such as a tag to analyze an analyte. The incorporated tag or labels do not substantially interfere with the conduct of the reaction scheme. For example, the incorporated tag or label does not interfere with the binding constant of or the interaction between the analyte and its complementary binding member. The size and number of incorporated tags or labels may be related to the speed of capture and read rate. The speed of capture and read rate may be increased by increasing the size and/or number of incorporated tags or labels. The incorporated tag or labels do not alter the binding member kinetics, for example, antibody kinetics, or the reaction scheme. Exemplary tags include polymers such as, an anionic polymer or a cationic polymer (e.g., a polypeptide with a net positive charge, such as, polyhistidine or polylysine), where the polymer is about 5-1000 residues in length; a protein (e.g., a globular protein) which does not cross react with the binding member and/or interfere with the assay, a dendrimer, e.g., a DNA dendrimer; and a charged particle, e.g., a bead. A polymer tag may include a nucleic acid, such as, a deoxyribonucleic acid or a ribonucleic acid. A polymer tag may include a nucleobase polymer. In certain cases, the tag may be DNA or a RNA aptamer, where the aptamer does not bind to the analyte. A polymer tag or a particle (e.g., a bead) may be sufficiently large to generate a reproducible signal. Aptamers may be 20-220 bases in length, e.g., 20-60 bases long. The size of the particle (e.g., a bead or a dendrimer) may range from about 1 nm to about 950 nm in diameter for example, 10 nm-900 nm, 20 nm-800 nm, 30 nm-700 nm, 50 nm-600 nm, 80 nm-500 nm, 100 nm-500 nm, 200 nm-500 nm, 300 nm-500 nm, or 400 nm-500 nm in diameter, e.g., 10 nm, 20 nm, 30 nm, 50 nm, 100 nm, 200 nm, 300 nm, 400 nm, 500 nm, 600 nm, 700 nm, 800 nm, or 900 nm. In certain cases, the bead/particle may be made of a material that has a net negative or positive charge or can be treated to have a net negative or positive charge. Exemplary beads/particles include those made from organic or inorganic polymers. Organic polymers include polymers such as, polystyrene, carbon, polyacrylamide, etc. Inorganic polymers include silicon or metal beads/particles. In certain cases, the beads/particles may not be magnetic.

In certain cases, the tag may be a single stranded DNA or RNA. The single stranded DNA or RNA may be hybridized to a probe molecule prior to. In certain cases, the method may include analysis of multiple analytes in a single sample. The second binding members that bind to the different analytes in a sample may include different single stranded DNA or RNA attached thereto as tags and the different single stranded DNA or RNA may be hybridized to different probes that further distinguish the different single stranded DNA or RNA from each other. In other embodiments, the tags attached to the different second binding members may have different hairpin structures (e.g., length of the hairpin structure) that are distinguishable. In yet another embodiment, the tags attached to the different second binding members may have different lengths that are distinguishable—for example, the tags may be double stranded DNA of different lengths (e.g., 25 bp, 50 bp, 75 bp, 100 bp, 150 bp, 200 bp, or more). In certain cases, the tags attached to the different second binding members may have different lengths of polyethylene glycol (PEG) or may be DNA or RNA modified differentially with PEG.

It is noted that reference to a tag or a tag molecule encompasses a single tag or a single tag molecule as well as multiple tags (that all may be identical). The tag may be any size or shape. In some embodiments, the tag may be a nanoparticle or a nanobead about 10 and 950 nm in diameter, e.g., 20-900 nm, 30-800 nm, 40-700 nm, 50-600 nm, 60-500 nm, 70-400 nm, 80-300 nm, 90-200 nm, 100-150 nm, 200-600 nm, 400-500 nm, 2-10 nm, 2-4 nm, or 3-4 nm in diameter. The tag may be substantially spherical, for example a spherical bead or nanobead, or hemispherical. The tag may be a protein about 0.5 kDa to about 50 kDa in size, e.g., about 0.5 kDa to about 400 kDa, about 0.8 kDa to about 400 kDa, about 1.0 kDa to about 400 kDa, about 1.5 kDa to about 400 kDa, about 2.0 kDa to about 400 kDa, about 5 kDa to about 400 kDa, about 10 kDa to about 400 kDa, about 50 kDa to about 400 kDa, about 100 kDa to about 400 kDa, about 150 kDa to about 400 kDa, about 200 kDa to about 400 kDa, about 250 kDa to about 400 kDa, about 300 kDa to about 400 kDa, about 0.5 kDa to about 300 kDa, about 0.8 kDa to about 300 kDa, about 1.0 kDa to about 300 kDa, about 1.5 kDa to about 300 kDa, about 2.0 kDa to about 300 kDa, about 5 kDa to about 300 kDa, about 10 kDa to about 300 kDa, about 50 kDa to about 300 kDa, about 100 kDa to about 300 kDa, about 150 kDa to about 300 kDa, about 200 kDa to about 300 kDa, about 250 kDa to about 300 kDa, about 0.5 kDa to about 250 kDa, about 0.8 kDa to about 250 kDa, about 1.0 kDa to about 250 kDa, about 1.5 kDa to about 250 kDa, about 2.0 kDa to about 250 kDa in size, about 5 kDa to about 250 kDa, about 10 kDa to about 250 kDa, about 50 kDa to about 250 kDa, about 100 kDa to about 250 kDa, about 150 kDa to about 250 kDa, about 200 kDa to about 250 kDa, about 0.5 kDa to about 200 kDa, about 0.8 kDa to about 200 kDa, about 1.0 kDa to about 200 kDa, about 1.5 kDa to about 200 kDa, about 2.0 kDa to about 200 kDa in size, about 5 kDa to about 200 kDa, about 10 kDa to about 200 kDa, about 50 kDa to about 200 kDa, about 100 kDa to about 200 kDa, about 150 kDa to about 200 kDa, about 0.5 kDa to about 100 kDa, about 0.8 kDa to about 100 kDa, about 1.0 kDa to about 100 kDa, about 1.5 kDa to about 100 kDa, about 2.0 kDa to about 100 kDa, about 5 kDa to about 100 kDa, about 10 kDa to about 100 kDa, about 50 kDa to about 100 kDa, about 0.5 kDa to about 50 kDa, about 0.8 kDa to about 50 kDa, about 1.0 kDa to about 50 kDa, about 1.5 kDa to about 50 kDa, about 2.0 kDa to about 50 kDa, about 5 kDa to about 50 kDa, about 10 kDa to about 50 kDa. about 10 kDa to about 90 kDa, about 10 kDa to about 80 kDa, about 10 kDa to about 70 kDa, about 10 kDa to about 60 kDa, about 20 kDa to about 90 kDa, about 20 kDa to about 80 kDa, about 20 kDa to about 70 kDa, about 20 kDa to about 60 kDa, about 40 kDa to about 90 kDa, about 40 kDa to about 80 kDa, about 40 kDa to about 70 kDa, or about 40 kDa to about 60 kDa.

In certain embodiments, the tag may be a nanoparticle or nanobead. As noted herein, the nanoparticle may be reversibly (e.g., cleavably) attached to the second binding member. In certain aspects, the nanoparticle may be a nanobead of a defined diameter. In certain cases, the methods, systems, and devices of the present disclosure may be used to simultaneously analyze a plurality of different analytes in a sample. For such analysis a plurality of second binding members that each specifically bind to a cognate analyte may be used. Each of the different second binding member may be attached to a different sized nanobead that may be used to identify the second binding member. For example, the different nanobead tags may have different diameters, such as, 1 nm, 2 nm, 4 nm, 6 nm, 8 nm, 10 nm, 12 nm, 14 nm, or larger, such as up to 20 nm, 30 nm, 50 nm, 100 nm, 200 nm, 300 nm, 400 nm, 500 nm, 600 nm, 700 nm, 800 nm, 900 nm, 950 nm, or 990 nm.

Exemplary nanoparticles that may be used as tags in the present methods include gold nanoparticles or polystyrene nanoparticles ranging in diameter from 5 nm-950 nm.

In certain cases, the tag may be a polymer, such as, a nucleic acid. The presence of the tag may be determined by detecting a signal characteristic of the tag, such as a signal related to the size or length of the polymer tag. The size or length of the polymer tag can be determined by measuring its residence time in the pore or channel, e.g., by measuring duration of transient blockade of current.

Elements which can be part of, all of, associated with, or attached to the tag or label include: a nanoparticle; gold particle; silver particle; silver, copper, zinc, or other metal coating or deposit; polymer; drag-tag (as defined herein); magnetic particle; buoyant particle; metal particle; charged moiety; dielectrophoresis tag, silicon dioxide, with and without impurities (e.g., quartz, glass, etc.); poly(methylmethacrylate) (PMMA); polyimide; silicon nitride; gold; silver; quantum dot (including CdS quantum dot); carbon dot; a fluorophore; a quencher; polymer; polystyrene; Janus particle; scattering particle; fluorescent particle; phosphorescent particle; sphere; cube; insulator; conductor; barcoded or labeled particle; porous particle; solid particle; nanoshell; nanorod; microsphere; analyte such as a virus, cell, parasite and organism; nucleic acid; protein; molecular recognition element; spacer; PEG; dendrimer; charge modifier; magnetic material; enzyme; DNA including aptamer sequence; amplifiable DNA; repeated sequence of DNA; fusion or conjugate of detectable elements with molecular recognition elements (e.g., engineered binding member); anti-antibody aptamer; aptamer directed to antibody-binding protein; absorbed or adsorbed detectable compound; heme; luciferin; a phosphor; an azido, or alkyne (e.g., terminal or non-terminal alkyne) or other click chemistry participant.

In certain embodiments, the tag may be chosen to provide a rate of capture that is sufficiently high to enable a rapid analysis of a sample. In certain embodiments, the capture rate of the tag may be about 1 event per 10 seconds, 1 event per 5 seconds, 1 event per second or higher. In certain embodiments, linear polymer tags, such as, ribose polymers, deoxyribose polymers, oligonucleotides, DNA, or RNA may be used.

In certain cases, linear polymer tags, such as, ribose polymers, deoxyribose polymers, oligonucleotides, DNA, or RNA may not be used as the capture rate for these tags may be too low for certain applications. Tags that are hemispherical, spherical or substantially spherical in shape and thus shorten the assay duration may be used in applications requiring faster tag counting. In certain cases, the size of the spherical or hemispherical tag may be chosen based on the capture rate needed for the assay. For example, for a higher capture rate, spherical or hemispherical tags of larger size may be selected. In certain cases, the tag may be spherical tag, such as, a nanoparticle/nanobead that has a capture rate about a 10 times, 30 times, 50 times, 100 times, 300 times, 500 times, or a 1000 times faster than capture rate for a linear tag, such as, a DNA tag, under the same measurement conditions.

In some embodiments, the tag is may be conjugated to an antibody, for example, a CPSP antibody conjugate. In some embodiments, the tag may be conjugated to an antibody with a spacer, for example, a CPSP antibody conjugate with a spacer. In some embodiments, the tag may be may be conjugated to an oligonucleotide and an antibody, for example, a CPSP oligonucleotide-antibody conjugate. In some embodiments, the tag may be may be conjugated to an oligonucleotide and an antibody with a spacer, for example, a CPSP oligonucleotide-antibody conjugate with spacer. In some embodiments, the tag may be may be conjugated to an oligonucleotide, for example, a CPSP oligonucleotide conjugate.

In certain embodiments methods described herein may include a specific binding member bound to a detectable label, such as, a signal-producing substance, such as chromagens, fluorescent compounds, enzymes, chemiluminescent compounds, radioactive compounds, particles (provided that they have fluorescent properties) and the like. Examples of labels that include moieties that produce light, e.g., acridinium compounds, and moieties that produce fluorescence, e.g., fluorescein.

Any suitable signal-producing substance known in the art can be used as a detectable label. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like (if enzymes are used then a corresponding enzymatic substrate must also be added)), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543, 524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965);

Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

Cleavable Linker

The tags used in the methods described herein may be attached to specific binding member by a generic linker. The cleavable linker ensures that the tag can be removed. The generic linker may be a cleavable linker. For example, the tag may be attached to the second binding member via a cleavable linker. The complex of the first binding member-analyte-second binding member may be exposed to a cleavage agent that mediates cleavage of the cleavable linker. The linker can be cleaved by any suitable method, including exposure to acids, bases, nucleophiles, electrophiles, radicals, metals, reducing or oxidizing agents, light, temperature, enzymes etc. Suitable linkers can be adapted from standard chemical blocking groups, as disclosed in Greene & Wuts, Protective Groups in Organic Synthesis, John Wiley & Sons. Further suitable cleavable linkers used in solid-phase synthesis are disclosed in Guillier et al. (Chem. Rev. 100:2092-2157, 2000). The linker may be acid-cleavable, base-cleavable or photocleavable. A redox reaction may be part of the cleavage scheme. The cleavable linker may be a charged polymer.

The linker may be a photocleavable linker, a chemically cleavable linker, or a thermally cleavable linker. Where the linker is a photocleavable group, the cleavage agent may be light of appropriate wavelength that disrupts or cleaves the photocleavable group. In many embodiments, the wavelength of light used to cleave the photocleavable linking group ranges from about 180 nm to 400 nm, e.g., from about 250 nm to 400 nm, or from about 300 nm to 400 nm. It is preferable that the light required to activate cleavage does not affect the other components of the analyte. Suitable linkers include those based on O-nitrobenzyl compounds and nitroveratryl compounds. Linkers based on benzoin chemistry can also be used (Lee et al., J. Org. Chem. 64:3454-3460, 1999).

Alternatively, where the cleavage linker is a chemically cleavable group, the cleavage agent may be a chemical agent capable of cleaving the group. A chemically cleavable linker may be cleaved by oxidation/reduction-based cleavage, acid-catalyzed cleavage, base-catalyzed cleavage, or nucleophilic displacement. For example, where the linking group is a disulfide, dithiothreitol or betamercaptoethanol may be used to release the tag. In yet other embodiments where the linking group is a restriction site, the agent is a catalytic agent, such as an enzyme which may be a hydrolytic enzyme, a restriction enzyme, or another enzyme that cleaves the linking group. For example, the restriction enzyme may be a type I, type II, type IIS, type III and type IV restriction enzyme.

In some embodiments, the cleavage linker is an enzymatic cleavable sequence. In one aspect of any of the embodiments herein, an enzymatic cleavable sequence is a nucleic acid sequence of 2, 3, 4, 5, 6, 7, 8, 9 or 10 nucleotides in length. In one embodiment, the enzymatic cleavable sequence comprises a sequence of at least 10 nucleotides. In one embodiment, the enzymatic cleavable sequence comprises a sequence of between 2 and 20 nucleotides. In one embodiment, the enzymatic cleavable sequence comprises a sequence of between 2 and 15 nucleotides. In one embodiment, the enzymatic cleavable sequence comprises a sequence of between 4 and 10 nucleotides. In one embodiment, the enzymatic cleavable sequence comprises a sequence of between 4 and 15 nucleotides.

For example, the cleavable linker may be an acridinium, ethers such as substituted benzyl ether or derivatives thereof (e.g., benzylhydryl ether, indanyl ether, etc.) that can be cleaved by acidic or mild reductive conditions (e.g., hydrogen peroxide to produce an acridone and a sulfonamide), a charged polymer generated using P-elimination, where a mild base can serve to release the product, acetals, including the thio analogs thereof, where detachment is accomplished by mild acid, particularly in the presence of a capturing carbonyl compound, photolabile linkages (e.g., O-nitrobenzoyl, 7-nitroindanyl, 2-nitrobenzhydryl ethers or esters, etc.), or peptide linkers, which are subject to enzymatic hydrolysis, particularly where the enzyme recognizes a specific sequence, such as a peptide for Factor Xa or enterokinase. Examples of linkers include, but are not limited to, disulfide linkers, acid labile linkers (including dialkoxybenzyl linkers), Sieber linkers, indole linkers, t-butyl Sieber linkers, electrophilically cleavable linkers, nucleophilically cleavable linkers, photocleavable linkers, cleavage under reductive conditions, oxidative conditions, cleavage via use of safety-catch linkers, and cleavage by elimination mechanisms.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system. The use of thiophilic metals, such as nickel, silver or mercury, in the cleavage of thioacetal or other sulphur-containing protecting groups can also be considered for the preparation of suitable linker molecules.

For nucleophilic cleavage, groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

A linker susceptible to reductive cleavage may be used such as with disulphide bond reduction. Catalytic hydrogenation using palladium-based catalysts has been used to cleave benzyl and benzyloxycarbonyl groups.

Oxidation-based approaches are well known in the art. These include oxidation of p-alkoxybenzyl groups and the oxidation of sulphur and selenium linkers. Aqueous iodine to cleave disulphides and other sulphur or selenium-based linkers may also be used.

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., J. Org. Chem. 62:5165-5168, 1997).

Elimination reactions may also be used. For example, the base-catalysed elimination of groups such as Fmoc and cyanoethyl, and palladium-catalysed reductive elimination of allylic systems, may be used.

Integrated Digital Microfluidic and Analyte Detection Device

Systems, devices, and method are described herein that relate to an integrated digital microfluidic and analyte detection device.

In certain embodiments, the integrated digital microfluidic and analyte detection device may have two modules: a sample preparation module and an analyte detection module. In certain embodiments, the sample preparation module and the analyte detection module are separate or separate and adjacent. In certain embodiments, the sample preparation module and the analyte detection module are co-located, comingled or interdigitated. The sample preparation module may include a series or plurality of electrodes for moving, merging, diluting, mixing, separating droplets of samples and reagents. The analyte detection module may include an array of wells in which an analyte related signal is detected. In certain cases, the detection module may also include the series or plurality of electrodes for moving a droplet of prepared sample to the array of wells. In certain embodiments, the detection module may include an array of wells in a first substrate (e.g., upper substrate) which is disposed over a second substrate (e.g., lower substrate) separated by a gap. In these embodiments, the array of wells is in an upside-down orientation. In certain embodiments, the detection module may include an array of wells in a second substrate (e.g., lower substrate) which is disposed below a first substrate (e.g., upper substrate) separated by a gap. In such embodiments, the first substrate and the second substrate are in a facing arrangement. A droplet may be moved (e.g., by electrical actuation) to the array of wells using electrode(s) present in the first substrate and/or the second substrate. In certain embodiments, the array of wells including the region in between the wells may be hydrophobic. In other embodiments, the series or plurality of electrodes may be limited to the sample preparation module and a droplet of prepared sample (and/or a droplet of immiscible fluid) may be moved to the detection module using other means.

In certain embodiments, the sample preparation module may be used for performing steps of an immunoassay. Any immunoassay format may be used to generate a detectable signal which signal is indicative of presence of an analyte of interest in a sample and is proportional to the amount of the analyte in the sample. Exemplary immunoassays are described herein.

In certain cases, the detection module includes the array of wells that are optically interrogated to measure a signal related to the amount of analyte present in the sample. The array of wells may have sub-femtoliter volume, femtoliter volume, sub-nanoliter volume, nanoliter volume, sub-microliter volume, or microliter volume. For example the array of wells may be array of femoliter wells, array of nanoliter wells, or array of microliter wells. In certain embodiments, the wells in an array may all have substantially the same volume. The array of wells may have a volume up to 100 µl, e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

In certain embodiments, the sample preparation module and the detection module may both be present on a single base substrate and both the sample preparation module and the detection module may include a series or plurality of electrodes for moving liquid droplets. In certain embodiments, such a device may include a first substrate and a second substrate, where the second substrate is positioned over the first substrate and separated from the first substrate by a gap. The first substrate may include a first portion (e.g., proximal portion) at which the sample preparation module is located, where a liquid droplet is introduced into the device, and a second portion (e.g., distal portion) towards which the liquid droplet moves, at which second portion the detection module is located. It will be understood by one skilled in the art that the use of "proximal" in view of "distal" and "first" in view of "second" are relative terms and are interchangeable with respect to each other. In certain embodiments, first portion and the second portion are separate or separate and adjacent. In certain embodiments, the first portion and the second portion are co-located, comingled or interdigitated. The first substrate may include a series or plurality of electrodes overlayed on an upper surface of the first substrate and extending from the first portion to the second portion. The first substrate may include a layer disposed on the upper surface of the first substrate, covering the series or plurality of electrodes, and extending from the first portion to the second portion. The first layer may be made of a material that is a dielectric and a hydrophobic material. Examples of a material that is dielectric and hydrophobic include polytetrafluoroethylene material (e.g., Teflon®) or a fluorosurfactant (e.g., FluoroPel™). The first layer may be deposited in a manner to provide a substantially planar surface. An array of wells may be positioned in the second portion of the first substrate and overlying a portion of the series or plurality of electrodes, and form the detection module. The array of wells may be positioned in the first layer. In certain embodiments, prior to or after fabrication of the array of wells in the first layer, a hydrophilic layer may be disposed over the first layer in the second portion of the first substrate to provide an array of wells that have a hydrophilic surface. The space/gap between the first and second substrates may be filled with air or an immiscible fluid. In certain embodiments, the space/gap between the first and second substrates may be filled with air.

In certain embodiments, the sample preparation module and the detection module may both be fabricated using a single base substrate but a series or plurality of electrodes for moving liquid droplets may only be present only in the sample preparation module. In such an embodiment, the first substrate may include a series or plurality of electrodes overlayed on an upper surface of the first substrate at the first portion of the first substrate, where the series or plurality of electrodes do not extend to the second portion of the first substrate. In such embodiments, the series or plurality of electrodes are only positioned in the first portion. A first layer of a dielectric/hydrophobic material (e.g., Teflon), as described above, may be disposed on the upper surface of the first substrate and may cover the series or plurality of electrodes. In certain embodiments, the first layer may be disposed only over a first portion of the first substrate. In other embodiments, the first layer may be disposed over the upper surface of the first substrate over the first portion as well as the second portion. An array of wells may be positioned in the first layer in the second portion of the first substrate, forming the detection module that does not include a series or plurality of electrodes present under the array of wells.

In certain cases, the first layer may be a dielectric layer and a second layer of a hydrophobic material may be disposed over the dielectric layer. The array of wells may be positioned in the hydrophobic layer. Prior to or after fabrication of the array of wells in the hydrophobic layer, a hydrophilic layer may be disposed over the hydrophobic layer in the second portion of the first substrate.

In certain embodiments, the second substrate may extend over the first and second portions of the first substrate. In such an embodiment, the second substrate may be substantially transparent, at least in region overlaying the array of wells. In other cases, the second substrate may be disposed in a spaced apart manner over the first portion of the first substrate and may not be disposed over the second portion of the first substrate. Thus, in certain embodiments, the second substrate may be present in the sample preparation module but not in the detection module.

In certain cases, the second substrate may include a conductive layer that forms an electrode. The conductive layer may be disposed on a lower surface of the second substrate. The conductive layer may be covered by a first layer made of a dielectric/hydrophobic material, as described above. In certain cases, the conductive layer may be covered by a dielectric layer. The dielectric layer may be covered by a hydrophobic layer. The conductive layer and any layer(s) covering it may be disposed across the lower surface of the second substrate or may only be present on the first portion of the second substrate. In certain embodiments, the second substrate may extend over the first and second portions of the first substrate. In such an embodiment, the second substrate and any layers disposed thereupon (e.g., conductive layer, dielectric layer, etc.) may be substantially transparent, at least in region overlaying the array of wells.

In other cases, the series or plurality of electrodes on the first substrate may be configured as co-planar electrodes and the second substrate may not include an electrode.

In certain cases, the electrodes present in the first layer and/or the second layer may be fabricated from a substantially transparent material, such as indium tin oxide, fluorine doped tin oxide (FTO), doped zinc oxide, and the like.

In some embodiments, the sample preparation module and the detection module may be fabricated on a single base substrate. In other embodiments, the sample preparation module and the detection modules may be fabricated on separate substrates that may subsequently be joined to form an integrated microfluidic and analyte detection device. In certain embodiments, the first and second substrates may be spaced apart using a spacer that may be positioned between the substrates.

The devices described herein may be planar and may have any shape, such as, rectangular or square, rectangular or square with rounded corners, circular, triangular, and the like.

Droplet-based microfluidics refer to generating and actuating (such as moving, merging, splitting, etc.) liquid droplets via active or passive forces. Examples of active forces include, but are not limited to, electric field. Exemplary active force techniques include electrowetting, dielectrophoresis, opto-electrowetting, electrode-mediated, electric-field mediated, electrostatic actuation, and the like or a combination thereof. In some examples, the device may actuate liquid droplets across the upper surface of the first layer (or upper surface of the second layer, when present) in the gap via droplet-based microfluidics, such as, electrowetting or via a combination of electrowetting and continuous fluid flow of the liquid droplets. In other examples, the device may include micro-channels to deliver liquid droplets from the sample preparation module to the detection module. In other examples, the device may rely upon the actuation of liquid droplets across the surface of the hydrophobic layer in the gap via droplet based microfluidics. Electrowetting may involve changing the wetting properties of a surface by applying an electrical field to the surface, and affecting the surface tension between a liquid droplet present on the surface and the surface. Continuous fluid flow may be used to move liquid droplets via an external pressure source, such as an external mechanical pump or integrated mechanical micropumps, or a combination of capillary forces and electrokinetic mechanisms. Examples of passive forces include, but are not limited to, T-junction and flow focusing methods. Other examples of passive forces include use of denser immiscible liquids, such as, heavy oil fluids, which can be coupled to liquid droplets over the surface of the first substrate and displace the liquid droplets across the surface. The denser immiscible liquid may be any liquid that is denser than water and does not mix with water to an appreciable extent. For example, the immiscible liquid may be hydrocarbons, halogenated hydrocarbons, polar oil, non-polar oil, fluorinated oil, chloroform, dichloromethane, tetrahydrofuran, 1-hexanol, etc.

The space between the first and second substrates may be up to 1 mm in height, e.g., 0.1 µm, 0.5 µm, 1 µm, 5 µm, 10 µm, 20 µm, 50 µm, 100 µm, 140 µm, 200 µm, 300 µm, 400 µm, 500 µm, 1 µm-500 µm, 100 µm-200 µm, etc. The volume of the droplet generated and moved in the devices described herein may range from about 10 µl to about 5 picol, such as, 10 µl-1 picol, 7.5 µl-10 picol, 5 µl-1 nL, 2.5 µl-10 nL, or 1 µl-100 nL, 800-200 nL, 10 nL-0.5 µl e.g., 10 µl, 1 µl, 800 nL, 100 nL, 10 nL, 1 nL, 0.5 nL, 10 picol, or lesser.

FIG. 1A illustrates an exemplary integrated digital microfluidic and analyte detection device 10. The device 10 includes a first substrate 11 and a second substrate 12, where the second substrate 12 is positioned over the first substrate 11 and separated from the first substrate by a gap 13. As illustrated in FIG. 1A, the second substrate 12 is the same length as the first substrate 11. However, in other exemplary devices, the first substrate 11 and the second substrate 12 may be of different lengths. The second substrate may or may not include an electrode. The first substrate 11 includes a first portion 15, where liquid droplet, such as, a sample droplet, reagent droplet, etc., is introduced onto the first substrate 11. The first substrate 11 includes a second portion 16, towards which a liquid droplet is moved. The first portion 15 may also be referred to as the sample preparation module and the second portion 16 may be referred to as the analyte detection module. The first substrate 11 includes a series or plurality of electrodes 17 positioned on the upper surface of the first substrate 11. A layer 18 of dielectric/hydrophobic material (e.g., Teflon which is both dielectric and hydrophobic) is disposed on the upper surface of the first substrate and covers the series or plurality of electrodes 17. An array of wells 19 is positioned in the layer 18 on the second portion 16 of the first substrate.

Figure 1B:
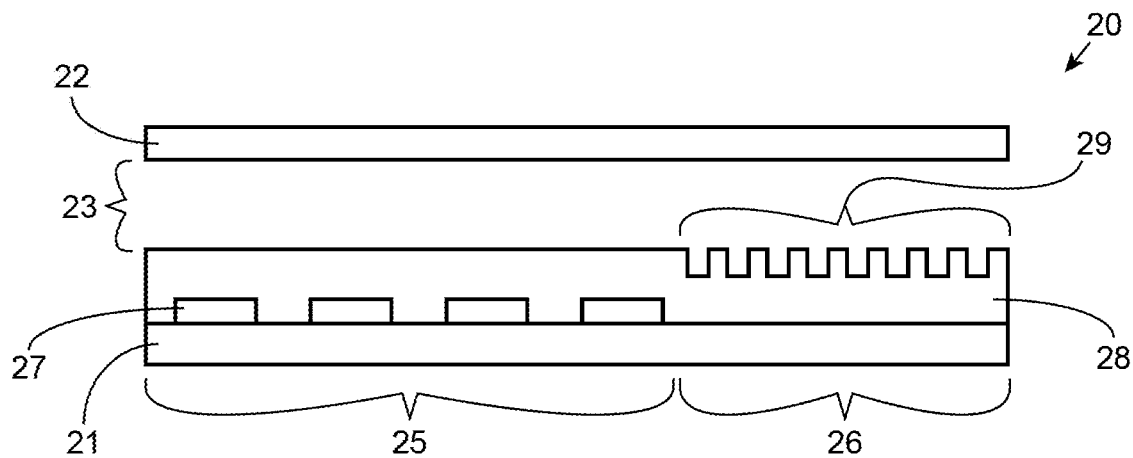
FIG. 1B illustrates a side view of the integrated digital microfluidic and analyte detection device according to another embodiment.

FIG. 1B illustrates another example of an integrated digital microfluidic and analyte detection device 20 that includes a first substrate 21 and a second substrate 22, where the second substrate 22 is positioned over the first substrate 20 and separated from an upper surface of the first substrate by a gap 23. The first substrate 21 includes a first portion 25, where a liquid is introduced onto the first substrate 21, and a second portion 26, towards which liquid is directed for detection of an analyte related signal. The first substrate 21 includes a series or plurality of electrodes 27 positioned on the upper surface of the first substrate. A layer 28 of dielectric material is positioned on the upper surface of the first substrate 21 and covers the series or plurality of electrodes 27. In this exemplary device, the series or plurality of electrodes 27 is positioned on only the first portion of the first substrate 21. The second substrate 22 may or may not include an electrode.

Figure 2A:
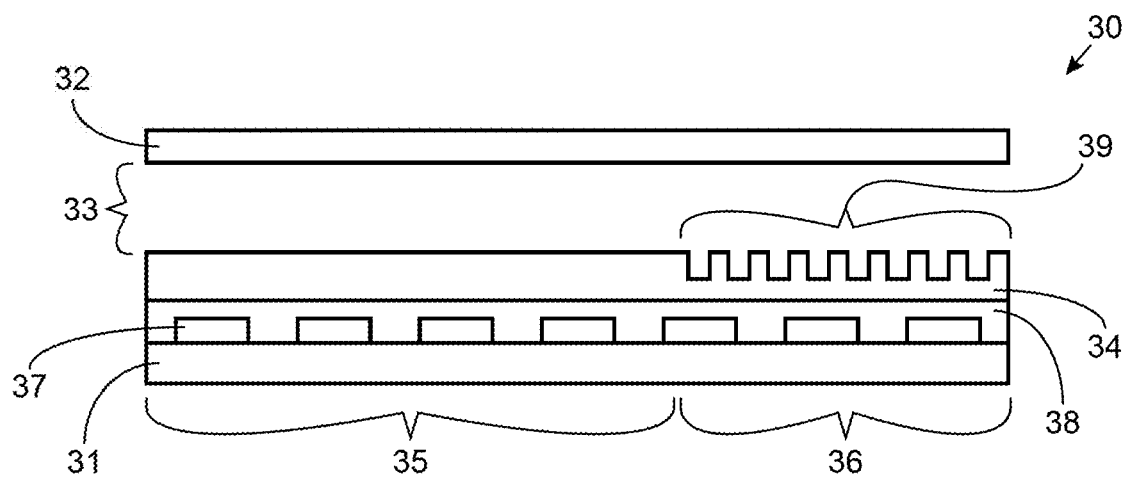
FIG. 2A illustrates a side view of an integrated digital microfluidic and analyte detection device according to an embodiment.

FIG. 2A illustrates another exemplary integrated digital microfluidic and analyte detection device 30. The device 30 includes a first substrate 31 and a second substrate 32, where the second substrate 32 is positioned over the first substrate 31 and separated from an upper surface of the first substrate by a gap 33. The first substrate 31 includes a first portion 35, where liquid droplet, such as, a sample droplet, reagent droplet, etc., is introduced onto the first substrate 31. The first substrate 31 includes a second portion 36, towards which a liquid droplet is moved. The first portion may also be referred to as the sample preparation module and the second portion may be referred to as the detection module. The first substrate 31 includes a series or plurality of electrodes 37 positioned on the upper surface of the first substrate. A layer 38 of dielectric material is disposed on the upper surface of the first substrate and covers the series or plurality of electrodes 37. A layer 34 of hydrophobic material is overlayed on the dielectric layer 38. An array of wells 39 is positioned in the hydrophobic layer 34 on the second portion of the first substrate 31. The array of wells may have a hydrophilic or hydrophobic surface.

Figure 2B:
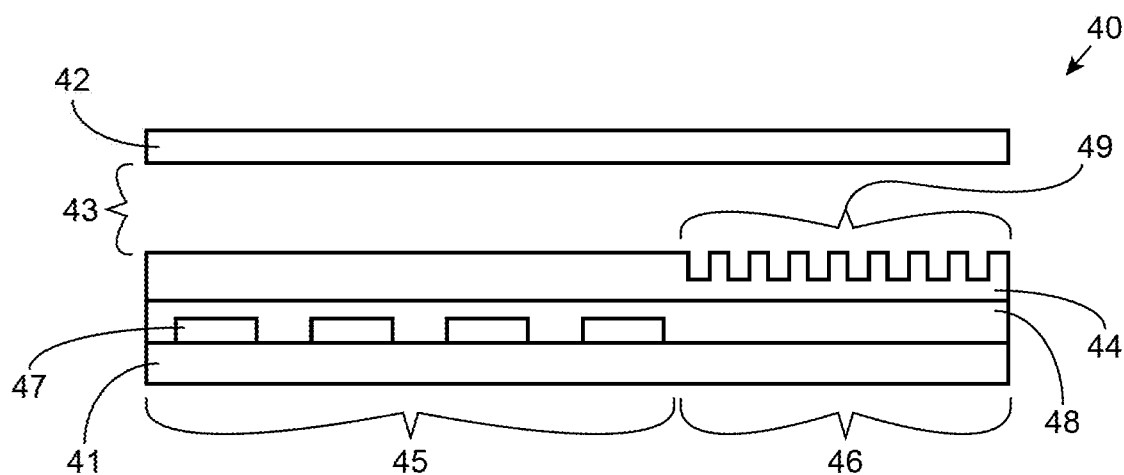
FIG. 2B illustrates a side view of the integrated digital microfluidic and analyte detection device according to another embodiment.

FIG. 2B illustrates another example of an integrated digital microfluidic and analyte detection device 40 that includes a first substrate 41 and a second substrate 42, where the second substrate 42 is positioned over the first substrate 40 and separated from an upper surface of the first substrate by a gap 43. The first substrate includes a first portion 45, where a liquid is introduced onto the first substrate 41, and a second portion 46, towards which liquid is directed for detection of an analyte related signal. The first substrate 41 includes a series or plurality of electrodes 47 positioned on the upper surface of the first substrate. A layer 48 of dielectric material is positioned on the upper surface of the first substrate 41 and covers the series or plurality of electrodes 47. In this exemplary device, the series or plurality of electrodes 47 is positioned on only the first portion 45 of the first substrate 41. The dielectric layer 48 covers the entire upper surface of the first substrate 41 and the hydrophobic layer 44 covers the entire upper surface of the dielectric layer. An array of wells 49 is positioned in the hydrophobic layer 44, and the array of wells 49 are positioned at only a portion of the hydrophobic layer overlaying the second portion 46 of the first substrate 41. In this example, the dielectric layer 48 is shown as extending over the entire upper surface of the first substrate 41. In other examples, the dielectric layer and the hydrophobic layer may be limited to the first portion and the wells may be positioned in a hydrophilic layer positioned on the second portion of the first substrate.

In some examples, liquid may be introduced into the gap via a droplet actuator (not illustrated). In other examples, liquid may be into the gap via a fluid inlet, port, or channel. Additional associated components of the device are not illustrated in the figures. Such figures may include chambers for holding sample, wash buffers, binding members, enzyme substrates, waste fluid, etc. Assay reagents may be contained in external reservoirs as part of the integrated device, where predetermined volumes may be moved from the reservoir to the device surface when needed for specific assay steps. Additionally, assay reagents may be deposited on the device in the form of dried, printed, or lyophilized reagents, where they may be stored for extended periods of time without loss of activity. Such dried, printed, or lyophilized reagents may be rehydrated prior or during analyte analysis.

In some examples, the first substrate can be made from a flexible material, such as paper (with ink jet printed electrodes) or polymers. In other examples, the first substrate can be made from a non-flexible material, such as for example, printed circuit board, plastic or glass or silicon. In some examples, the first substrate is made from a single sheet, which then may undergo subsequent processing to create the series or plurality of electrodes. In some examples, multiple series or plurality of electrodes may be fabricated on a first substrate which may be cut to form a plurality of first substrates overlayed with a series or plurality of electrodes. In some examples, the electrodes may be bonded to the surface of the conducting layer via a general adhesive agent or solder. The second substrate may be made from any suitable material including but not limited to a flexible material, such as paper (with or without ink jet printed electrodes), polymers, printed circuit board, and the like.

In some examples, the electrodes are comprised of a metal, metal mixture or alloy, metal-semiconductor mixture or alloy, or a conductive polymer. Some examples of metal electrodes include copper, gold, indium, tin, indium tin oxide, and aluminum. In some examples, the dielectric layer comprises an insulating material, which has a low electrical conductivity or is capable of sustaining a static electrical field. In some examples, the dielectric layer may be made of porcelain (e.g., a ceramic), polymer or a plastic. In some examples, the hydrophobic layer may be made of a material having hydrophobic properties, such as for example Teflon and generic fluorocarbons. In another example, the hydrophobic material may be a fluorosurfactant (e.g., FluoroPel). In embodiments including a hydrophilic layer deposited on the dielectric layer, it may be a layer of glass, quartz, silica, metallic hydroxide, or mica.

One having ordinary skill in the art would appreciate that the array (e.g., series) of electrodes may include a certain number of electrodes per unit area of the first substrate, which number may be increased or decreased based on size of the electrodes and a presence or absence of inter-digitated electrodes. Electrodes may be fabricated using a variety of processes including, photolithography, atomic layer deposition, laser scribing or etching, laser ablation, flexographic printing and ink-jet printing of electrodes.

In some examples, a special mask pattern may be applied to a conductive layer disposed on an upper surface of the first substrate followed by laser ablation of the exposed conductive layer to produce a series or plurality of electrodes on the first substrate.

In some examples, the electrical potential generated by the series or plurality of electrodes transfer liquid droplets formed on an upper surface of the first layer (or the second layer when present) covering the series or plurality of electrodes, across the surface of the digital microfluidic device to be received by the array of wells. Each electrode may be capable of independently moving the droplets across the surface of the digital microfluidic device.

Figure 3A:
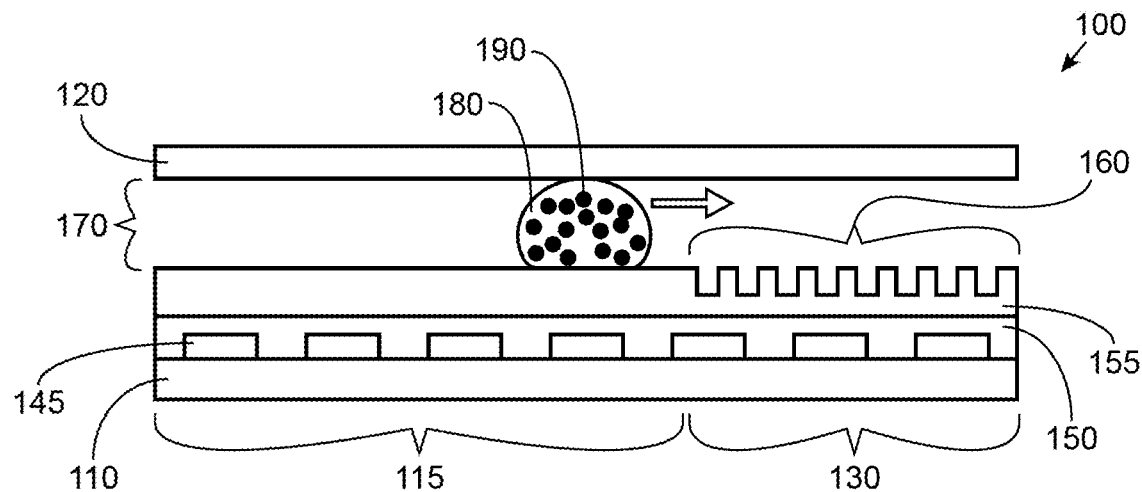
FIG. 3A illustrates a side view of the device of FIG. 2A with a liquid droplet being moved in the device.

FIG. 3A illustrates a side view of an exemplary integrated digital microfluidic and analyte detection device 100 with a liquid droplet being moved in the gap 170. The device 100 includes a first substrate 110 and a second substrate 120, where the second substrate 120 is positioned over the first substrate 110 and separated from an upper surface of the first substrate by a gap 170. The first substrate 110 includes a first portion 115, where liquid droplet, such as, a sample droplet, reagent droplet, etc., is introduced onto the first substrate 110. The first substrate 110 includes a second portion 130, towards which a liquid droplet is moved. The first portion may also be referred to as the sample preparation module and the second portion may be referred to as the detection module. The first substrate 110 includes a series or plurality of electrodes 145 positioned on the upper surface of the first substrate. A layer 150 of dielectric material is disposed on the upper surface of the first substrate and covers the series or plurality of electrodes 145. A layer 155 of hydrophobic material is overlayed on the dielectric layer 150. An array of wells 160 is positioned in the hydrophobic layer 155 on the second portion of the first substrate 110. The array of wells may have a hydrophilic or hydrophobic surface. As illustrated in FIG. 3A, a liquid droplet is illustrated as being actuated from the first portion 115 to the second portion 130 containing the array of wells 160. A liquid droplet 180 containing a plurality of beads or particles 190 is being moved across the first portion 115 and over to the second portion 130 via active directional movement using the series or plurality of electrodes 145. The arrow indicates the direction of movement of the liquid droplet. Although not shown here, polarizable oil may be used to move the droplet and seal the wells. Although beads/particles are illustrated here, the droplet may include analyte molecules instead of or in addition to the solid supports.

Figure 3B:
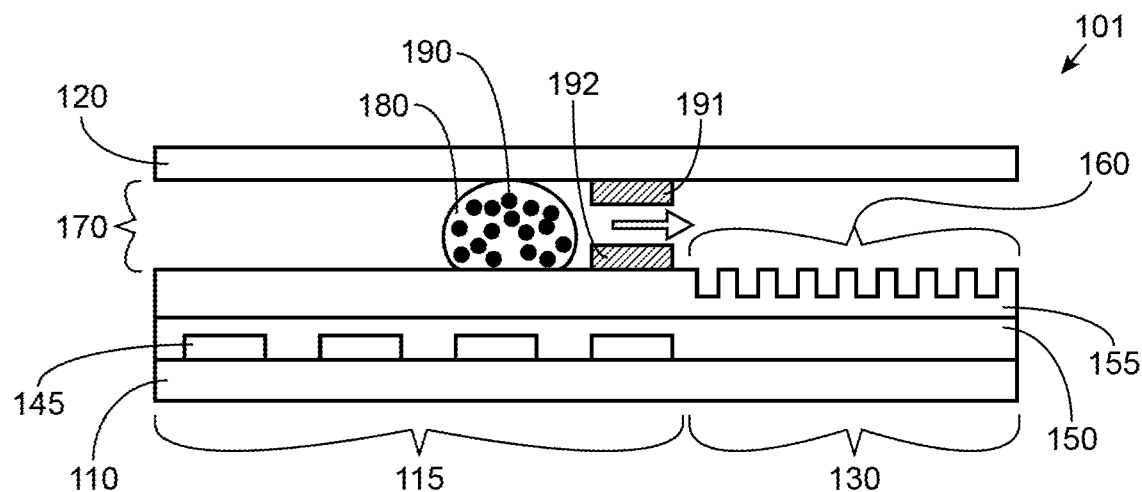
FIG. 3B illustrate a side view of the device of FIG. 2B with of droplet being moved in the device.

FIG. 3B illustrates a side view of an exemplary integrated digital microfluidic and analyte detection device 101 with a droplet 180 being moved in the gap 170 from the first portion 115 to the second portion 130 that includes the array of wells 160. The device 101 includes a first substrate 110 and a second substrate 120, where the second substrate 120 is positioned over the first substrate 110 and separated from an upper surface of the first substrate by a gap 170. The first substrate 110 includes a first portion 115, where liquid droplet, such as, a sample droplet, reagent droplet, etc., is introduced onto the first substrate 110. The first substrate 110 includes a second portion 130, towards which a liquid droplet is moved. The first portion may also be referred to as the sample preparation module and the second portion may be referred to as the detection module. The first substrate 110 includes a series or plurality of electrodes 145 positioned on the upper surface at the first portion 115 of the first substrate. A layer 150 of dielectric material is disposed on the upper surface of the first substrate and covers the series or plurality of electrodes 145. A layer 155 of hydrophobic material is overlayed on the dielectric layer 150. An array of wells 160 is positioned in the hydrophobic layer 155 on the second portion of the first substrate 110. The array of wells may have a hydrophilic or hydrophobic surface. Movement across the surface of the first portion of the device is via the electrodes 145 and then the droplet 180 is moved to the second portion using passive fluid force, such as capillary movement through capillary element formed by 191 and 192. In some examples, the capillary element may include a hydrophilic material for facilitating movement of the aqueous droplet from the first portion to the second portion in the absence of an applied electric field generated by the series or plurality of electrodes. In some examples, a striping of a hydrophobic material may be disposed next to the hydrophilic capillary space. The striping of hydrophobic material may be used to move a droplet of immiscible fluid over to the array of wells in absence of the digital microfluidics electrodes. Some examples of liquids that may flow through a hydrophobic capillary element includes heavy oil fluids, such as fluorinated oils, can be used to facilitate liquid droplet movement over the array of wells. In other examples, oil droplets may also be utilized to remove excess droplets.

In addition to moving aqueous-based fluids, immiscible fluids, such as organic based immiscible fluids, may also be moved by electrical-mediated actuation. It is understood that droplet actuation is correlated with dipole moment and dielectric constant, which are interrelated, as well as with conductivity. In certain embodiments, the immiscible liquid may have a molecular dipole moment greater than about 0.9 D, dielectric constant greater than about 3 and/or conductivities greater than about $10^{-9}$ S m$^{-1}$. Examples of movable immiscible liquids and characteristics thereof are discussed in Chatterjee, et al. Lab on Chip, 6, 199-206 (2006). Examples of use of the immiscible liquid in the analyte analysis assays disclosed herein include aiding aqueous droplet movement, displacing aqueous fluid positioned above the wells, displacing undeposited beads/particles/analyte molecules from the wells prior to optical interrogation of the wells, sealing of the wells, and the like. Some examples of organic-based immiscible fluids that are moveable in the devices disclosed herein include 1-hexanol, dichloromethane, dibromomethane, THF and chloroform. Organic-based oils that satisfy the above mentioned criteria would also be expected to be moveable under similar conditions. In some embodiments using immiscible fluid droplets, the gap/space in the device may be filled with air.

FIG. 4A illustrates a liquid droplet 180 containing beads or particles 190 that has been moved to the second portion of the integrated device of FIG. 3A and is positioned over the array of wells 160. The droplet may be continuously moved over the array of wells in linear or reciprocating motion or movement and may be paused over the array of wells. Moving of the droplet and/or pausing the droplet over the array of wells facilitates the deposition of the particles or beads 190 into the array of wells 160. The wells are dimensioned to include one bead/particle. In the device illustrated in FIG. 4A, the droplet is moved over the array of wells using the series or plurality of electrodes 145. Although beads/particles are depicted here, droplets contain analyte molecules may also be moved in a similar manner, and by pausing the droplet containing the analyte molecules above the wells for a sufficient period of time to allow for the analyte molecules to diffuse into the wells before the immiscible fluid seals the wells. The wells are dimensioned to include one bead/particle. The wells can also be dimensioned to include one analyte molecule per well.

FIG. 4B illustrates a liquid droplet 185 containing beads or particles 190 that has been moved to the second portion of the integrated device of FIG. 3B and is positioned over the array of wells without using a series or plurality of electrodes. In FIG. 4B, a droplet of hydrophobic liquid 195 (such as an immiscible fluid) is being used to move the liquid droplet over the well array to facilitate deposition of the beads/particles 190 into the wells 160. The direction of the arrow indicates the direction in which the droplet 185 is being moved.

Figure 5:
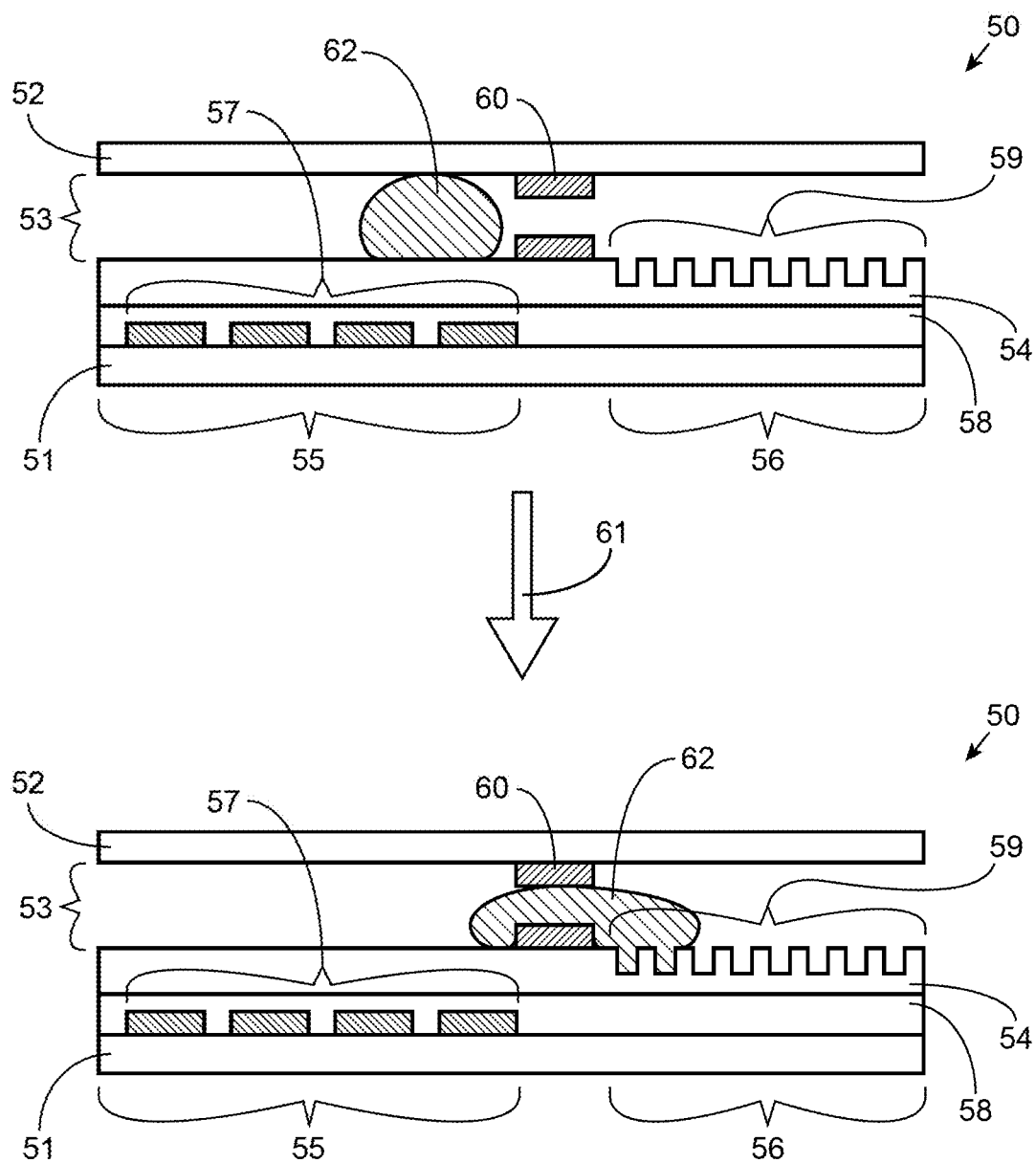
FIG. 5 illustrates an aqueous droplet being moved over the array of wells using a hydrophilic capillary region of the device.

FIG. 5 shows a hydrophobic fluid droplet 62 (e.g., polarizable fluid) being moved over the first portion 55 using the series or plurality of electrodes 57. The depicted device 50 includes a first substrate 51 and a second substrate 52, where the second substrate 52 is positioned over the first substrate 51 and separated from an upper surface of the first substrate by a gap 53. The first substrate 51 includes a first portion 55, where liquid droplet, such as, a sample droplet, reagent droplet, etc., is introduced onto the first substrate 51. The first substrate 51 includes a second portion 56, towards which a liquid droplet is moved. The first substrate 51 includes a series or plurality of electrodes 57 positioned on the upper surface at the first portion 55 of the first substrate. A layer 58 of dielectric material is disposed on the upper surface of the first substrate and covers the series or plurality of electrodes 57. A layer 54 of hydrophobic material is overlayed on the dielectric layer 58. An array of wells 59 is positioned in the hydrophobic layer 54 on the second portion of the first substrate 51. The array of wells may have a hydrophilic or hydrophobic surface. A capillary element 60 is formed by deposition of two stripes of a hydrophobic material on the first 51 and second substrates 52. The hydrophobic capillary facilitates movement of the hydrophobic fluid droplet 62 to the array of wells 59, in absence of the series or plurality of electrodes in the second portion 56. In other embodiments, the capillary element may be formed by deposition of two stripes of a hydrophilic material on the first 51 and second substrates 52. The hydrophilic material facilitates movement of an aqueous droplet to the array of wells 59, in absence of the series or plurality of electrodes in the second portion 56. In certain embodiments, the capillary element may include a pair of stripes of hydrophilic material alternating with a pair of stripes of hydrophobic material. An aqueous droplet may be directed to the region at which a pair of hydrophilic stripes is positioned, while a droplet of immiscible fluid may be directed to the region at which a pair of hydrophobic stripes is positioned.

Figure 6:
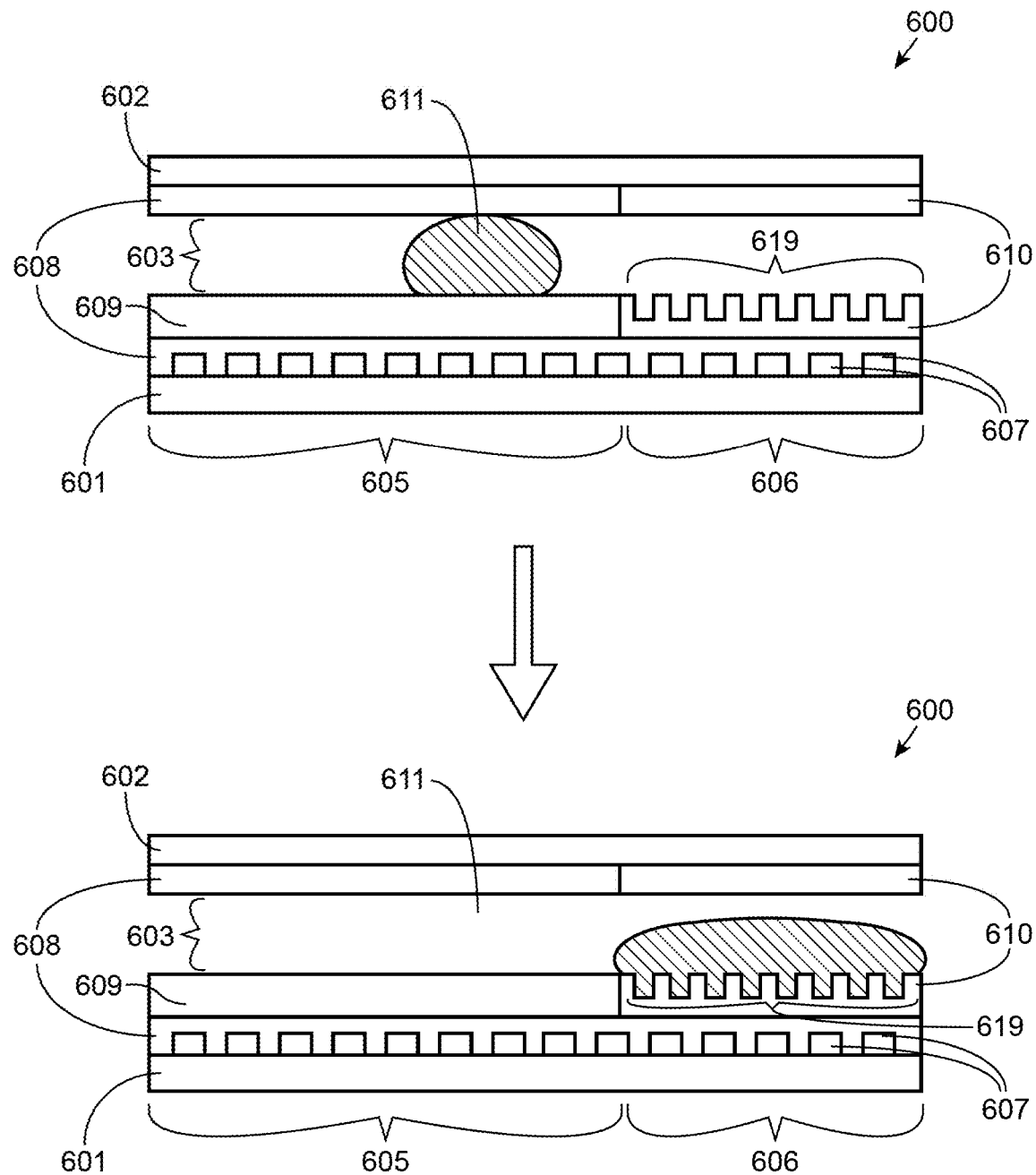
FIG. 6 illustrates an aqueous droplet being moved over the array of wells.

FIG. 6 depicts another embodiment of an integrated digital microfluidics and analyte detection device. The device 600 includes a bottom layer 601 over which an array of electrodes 607 is formed. The array of electrodes is covered by a dielectric layer 608. A hydrophobic layer 609 is disposed only in the first portion 605 of the bottom substrate. A hydrophilic layer 610 is disposed on the second portion 606 of the bottom substrate 601. An array of wells is located in the second portion in the hydrophilic layer 610. A top substrate 602 separated from the bottom substrate by a gap/space 603 is also depicted. The top substrate 602 includes a dielectric layer 608 disposed on a bottom surface of the top substrate over the first portion of the bottom substrate. The top substrate includes a hydrophilic layer 610 disposed on a bottom surface of the top substrate across from the second portion of the bottom substrate. An aqueous droplet 611 does not wet the hydrophobic layer and upon reaching the hydrophilic second portion the droplet 611 spreads over the array of wells 619, thereby facilitating movement of the aqueous phase via passive capillary forces. In a similar manner, the above concept may be reversed to facilitate wetting and spreading of an organic-based immiscible fluid over the wells. In this case, the top and bottom substrate on the second portion can be coated with a hydrophobic material/coating, thereby allowing an organic-based immiscible fluid to flow over the wells via passive capillary forces.

As used herein, digital microfluidics refers to use of a series of electrodes to manipulate droplets in a microfluidics device, e.g., move droplets, split droplets, merge droplets, etc. in a small space. As used herein, the terms "droplet(s)" and "fluidic droplet(s)" are used interchangeably to refer to a discrete volume of liquid that is roughly spherical in shape and is bounded on at least one side by a wall or substrate of a microfluidics device. Roughly spherical in the context of the droplet refers to shapes such as spherical, partially flattened sphere, e.g., disc shaped, slug shaped, truncated sphere, ellipsoid, hemispherical, or ovoid. The volume of the droplet in the devices disclosed herein may range from about 10 μl to about 5 μL, such as, 10 μl-1 pL, 7.5 μl-10 pL, 5 μl-1 nL, 2.5 μl-10 nL, or 1 μl-100 nL, e.g., 10 μl, 5 μl, 1 μl, 800 nL, 500 nL, or lesser.

In some examples, the array of wells includes a plurality of individual wells. The array of wells may include a plurality of wells that may range from 10 to $10^9$ in number per 1 $mm^2$. In certain cases, an array of about 100,000 to 500,000 wells (e.g., femtoliter wells) covering an area approximately 12 $mm^2$ may be fabricated. Each well may measure about 4.2 m wide×3.2 m deep (volume approximately 50 femtoliters), and may be capable of holding a single bead/particle (about 3 μm diameter). At this density, the femtoliter wells are spaced at a distance of approximately 7.4 μm from each other. In some examples, the well array may be fabricated to have individual wells with a diameter of 10 nm to 10,000 nm.

The placement of single beads/particles/analyte molecules in the wells allows for either a digital readout or analog readout. For example, for a low number of positive wells (<~70% positive) Poisson statistics can be used to quantitate the analyte concentration in a digital format; for high numbers of positive wells (>~70%) the relative intensities of signal-bearing wells are compared to the signal intensity generated from a single bead/particle/analyte molecule, respectively, and used to generate an analog signal. A digital signal may be used for lower analyte concentrations, whereas an analog signal may be used for higher analyte concentrations. A combination of digital and analog quantitation may be used, which may expand the linear dynamic range. As used herein, a "positive well" refers to a well that has a signal related to presence of a bead/particle/analyte molecule, which signal is above a threshold value. As used herein, a "negative well" refers to a well that may not have a signal related to presence of a bead/particle/analyte molecule. In certain embodiments, the signal from a negative well may be at a background level, i.e., below a threshold value.

The wells may be any of a variety of shapes, such as, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a microbead or microparticle present liquid droplets that have been moved over the well array. In some examples, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall.

In some examples, the array of wells can be fabricated through one or more of molding, pressure, heat, or laser, or a combination thereof. In some examples, the array of wells may be fabricated using nanoimprint/nanosphere lithography. Other fabrication methods well known in the art may can also be used.

Figure 7A:
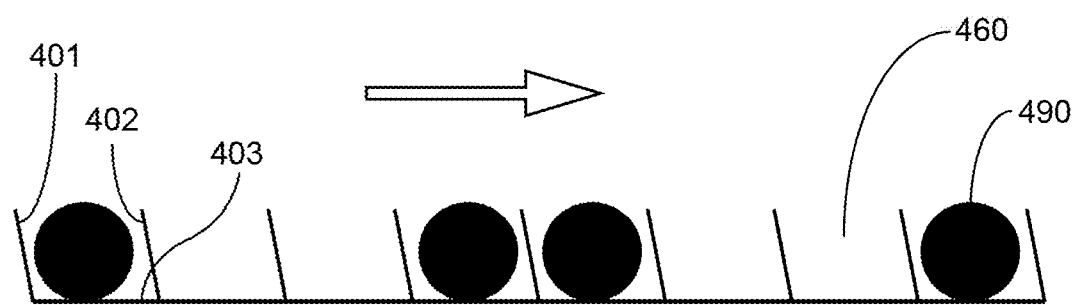
FIGS. 7A-7B illustrate various exemplary orientations of the sidewalls of the wells.
Figure 7B:
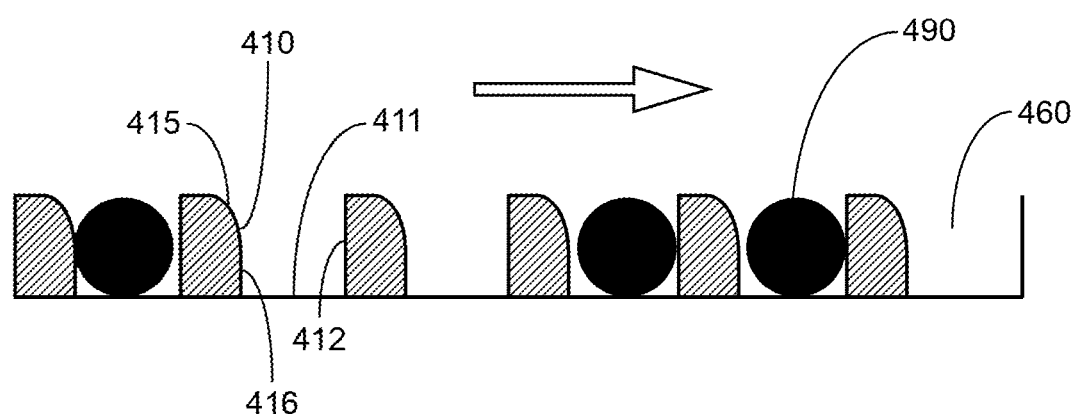

FIGS. 7A-7B illustrate several exemplary sidewall orientations of the wells. As illustrated in FIGS. 7A-B, the wells comprise a first sidewall opposite to a second sidewall. FIG. 7A illustrates a vertical cross-section showing individual wells 460 in the array of wells. FIG. 7A illustrates a first sidewall 401 and a second sidewall 402. The first side wall is at an obtuse angle with reference to a bottom surface 143 of the well and the second side wall is at an acute angle with reference to a bottom surface 143 of the well. The arrow illustrates the direction in which a liquid droplet moves across the array. This orientation of the sidewalls of the wells facilitates receiving and retaining beads/particles/analyte molecules 490.

In FIG. 7B, a top portion 415 of the first sidewall 410 is oriented at an obtuse angle with reference to a bottom 412 of the wells and a bottom portion 416 of the first sidewall 410 is oriented perpendicular to the bottom 412 of the wells, and the second sidewall 411 is oriented perpendicular to the bottom 412 of the wells, where movement of liquid droplets is in a direction parallel to the bottom of the wells and from the first sidewall to the second sidewall, where the top portion of the first sidewall is at an opening of the wells.

The integrated devices described herein may be fabricated by a number of methods. In certain cases, the methods may involve a combination of laser ablation, spray coating, roll to roll, flexographic printing, and nanoimprint lithography (NIL) to construct the first substrate, series or plurality of electrode, dielectric layer and hydrophobic layer.

In some examples, a plurality of rollers may unwind a first roll to drive the first substrate to a first position. A conductive material may then be applied to the first substrate. The conductive material may be patterned into a series or plurality of electrodes. In some examples, the printer device comprising one or more coating rollers to apply the at least one of the hydrophobic or the dielectric material to the at least one electrode pattern on the first substrate. In some examples, the coating rollers are to apply an anti-fouling material to the first substrate.

In some examples, the system further comprises a merger to align the first substrate with the second substrate. In some examples, the merger comprises two rollers. Also, some of the disclosed examples include a curing station to cure the hydrophobic material or the dielectric material. Some of the disclosed examples also include a bonding station to bond at least a first portion of the first substrate with at least a first portion of the second substrate. The bonded portions include the electrode pattern. The method also includes associating the first substrate and the second substrate at a spaced apart distance. The space between the first and second substrates may be about 0.01 mm to 1 mm in height, e.g., 0.1 µm, 0.5 µm, 1 µm, 5 µm, 10 µm, 20 µm, 50 µm, 100 µm, 140 µm, 200 µm, 300 µm, 400 µm, 500 µm, 1 µm-500 µm, 100 µm-200 µm, etc.

In some examples, the method includes embossing the first substrate to create one or more projections on the first substrate. In such examples, the projections are to separate the first substrate and the second substrate at the spaced apart distance.

The devices of the present disclosure may be operated manually or automatically or semiautomatically. In certain cases, the devices may be operated by a processor that runs a program for carrying out the steps required for generating an analyte related signal and detecting the signal. As used hereon, the phrase "analyte related signal" or "analyte associated signal" refers to a signal that is indicative of presence of an analyte and is proportional to the amount of the analyte in a sample. The signal may be fluorescence, chemiluminescence, colorimetric, turbidimetric, etc. In certain cases, the read out may be digital, for example, the number of positive counts (e.g., wells) is compared to the number of negative counts (e.g., wells) to obtain a digital count.

Figure 8:
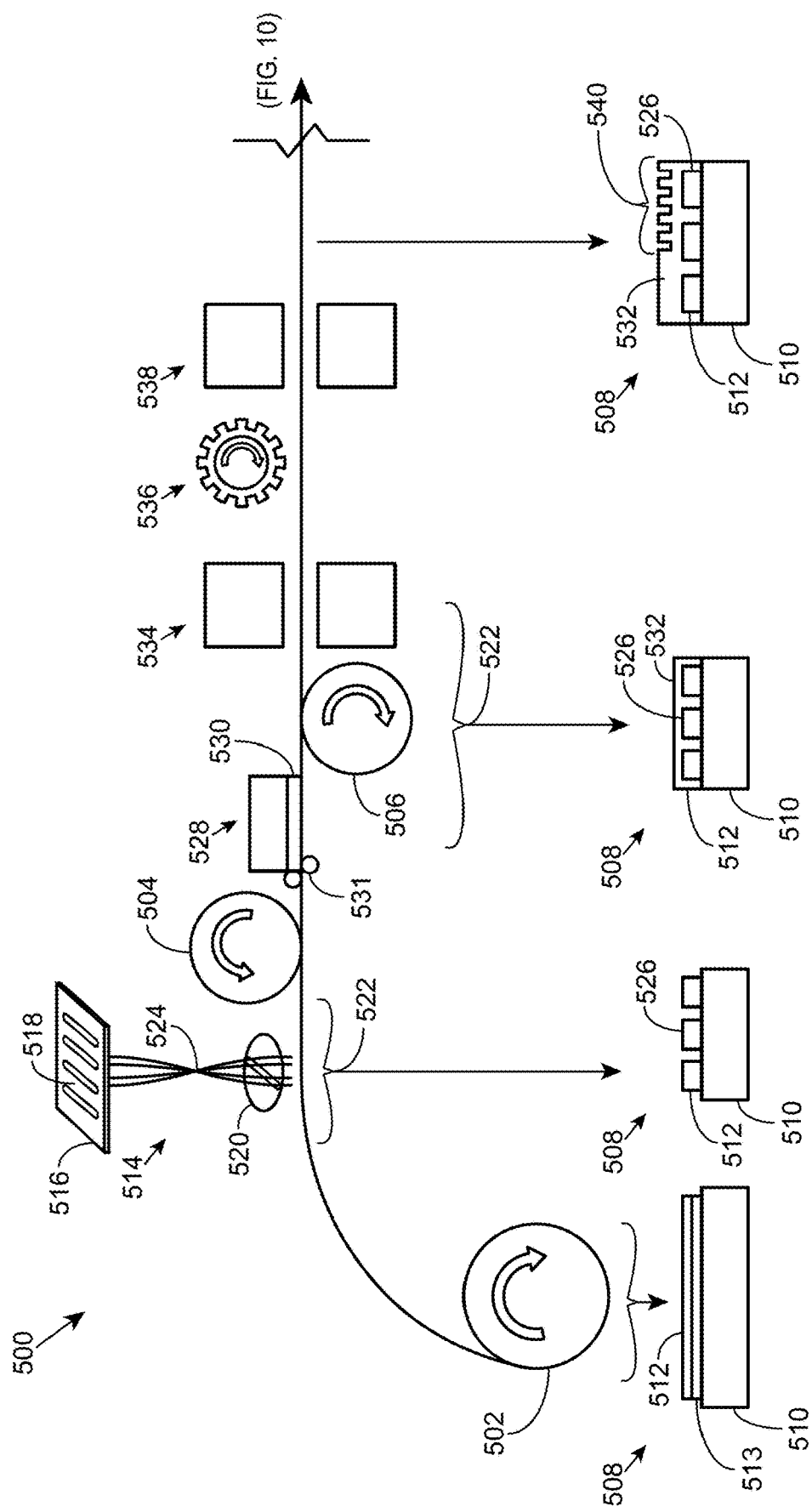
FIG. 8 illustrates an example of fabricating a second (e.g., bottom) substrate of the digital microfluidic and analyte detection device.

FIG. 8 is a diagram of a first exemplary system or assembly 500 for creating a base substrate of an integrated digital microfluidics and analyte detection device. The first example assembly 500 includes a series or a plurality of rollers, including a first roller 502, a second roller 504, and a third roller 506, which operate in synchronized rotation to drive a base substrate 508 through the first example assembly 500. The first example assembly 500 can include rollers in addition to the first through third rollers 502, 504, 506 to move the base substrate 508 through the assembly using roll-to-roll techniques. Other examples may use conveyors, pulleys and/or any other suitable transport mechanism(s).

In the first example assembly 500, the first roller 502 rotates to unwind the base substrate 508, which, in some examples, is a single sheet in a rolled configuration. The base substrate 508 includes a first layer 510 and a second layer 512. In this example, the first layer 510 comprises a non-conductive flexible substrate or web, such as for example a plastic, and the second layer 512 includes a conductive material. The conductive material of the second layer 512 can be, for example, a metal such as gold, silver, or copper, or a non-metallic conductor, such as a conductive polymer. In other examples different metal(s) or combination(s) of metal(s) and/or conductive polymer(s) may be used. In some examples, the base substrate 508 includes an optional adhesive layer 513 disposed between the non-conductive first layer 510 and the conductive second layer 512. As an example, the adhesive layer 513 can comprise chrome, with a layer of gold disposed on top of the chrome adhesive layer 513 to form the conductive second layer 512. Thus, in the base substrate 508 of FIG. 8, the non-conductive first layer 510 and the conductive second layer 512 are pre-adhered to form the base substrate 508 prior to being unwound by the first roller 502.

In the example base substrate 508 of FIG. 8, the non-conductive first layer 510 has a thickness of less than about 500 nm. As will be described below, such a thickness allows for the base substrate 508 to move through the example first assembly 500 via the plurality of rollers. Also, in some examples, the thickness of the nonconductive first layer 510 is greater than a thickness of the conductive second layer 512. As an example, the thickness of the conductive second layer 512 can be approximately 30 nm. In other examples, the thickness of the conductive second layer 512 is less than about 500 nm. In some examples, the thickness of the non-conductive first layer 510 and/or the conductive second layer 512 is selected based on, for example, the materials of the first and/or second layers 510, 512 and/or an operational purpose for which the droplet actuator formed from the base substrate 508 is to be used.

The first roller 502 drives the base substrate 508 to a laser ablation station 514. The laser ablation station 514 includes a mask 516 containing a master pattern 518 that is to be projected onto the conductive second layer 512 of the base substrate 508. The master pattern 518 associated with the mask 516 may be predefined based on characteristics such as resolution (e.g., number of electrodes per an area of the base substrate 508 to be ablated), electrode size, configuration of lines defining the electrode pattern, inter-digitation of the electrodes, gaps or spacing between the electrodes, and/or electrical traces for connecting the electrodes to an instrument, such as, a power source. In some examples, the characteristics of the master pattern 518 are selected based on one or more operational uses of the droplet actuator with which the base substrate 508 is to be associated (e.g., for use with biological and/or chemical assays). Also, in some examples, the master pattern 518 is configurable or reconfigurable to enable the laser ablation station 514 to form different patterns on the base substrate 508. Additionally or alternatively, in some examples the mask 516 is replaceable with one or more alternative masks.

The laser ablation station 514 includes a lens 520. As the base substrate 508 encounters the laser ablation station 514 as result of the rotation of the rollers (e.g., the first roller 502), a portion 522 of the base substrate 508 passes under or past the lens 520. The portion 522 may be, for example, a rectangular or square section of the base substrate 508 having an area less than the area of the base substrate 508 and including the conductive second layer 512. The lens 520 images or projects at least a portion of the master pattern 518 onto the conductive second layer 512 associated with the portion 522. A laser beam 524 is directed onto the portion 522 via the mask 516 and the lens 520 such that the laser beam 524 selectively penetrates the conductive second layer 512 based on the projected master pattern 518. In some examples, the non-conductive first layer 500 or a portion (e.g., a fraction of the thickness of the non-conductive first layer 510) may also be penetrated by the laser beam 524 based on the projected master pattern 518. The solid portions of the mask 516 block the laser beam 524, and the open portions of the mask 516 allow the laser beam 524 to pass through the mask 516 and into contact with the base substrate 508. The laser beam 524 can be associated with, for example, an excimer laser.

As a result of exposure to the laser beam 524, the irradiated nonconductive first layer 510 of the portion 522 absorbs energy associated with the laser beam 524. The irradiated non-conductive first layer 510 undergoes photochemical dissociation, resulting in a selective breaking up of the structural bonds of nonconductive first layer 510 and ejection of fragments of the non-conductive first layer 510 and portions of the conductive second layer 512 overlaying the irradiated non-conductive first layer 510 in accordance with the master pattern 518. In some examples, a depth (e.g., a radiation intensity) to which the laser beam 524 penetrates the base substrate 508 is predefined based on a depth (e.g., a thickness) of the non-conductive first layer 510 and/or the conductive second layer 512. In some examples, the laser beam 524 penetration depth is adjustable to change the depth at which the laser beam 524 ablates the conductive second layer 512 as a result of the fragmentation of the underlying nonconductive first layer 510. In some examples, this adjustment is dynamic as the example system 500 operates. Also, in some examples, the base substrate 508 undergoes cleaning after exposure to the laser beam 524 to remove particles and/or surface contaminants.

As illustrated in FIG. 8, after exposure to the laser ablation station 514, the portion 522 of the base substrate 508 includes an electrode array 526. The electrode array 526 is made up of a plurality of electrodes formed into the conductive second layer 512. As a result of the exposure to the laser beam 524 and fragmentation of the non-conductive first layer 510, portions of the conductive second layer 512 are removed from the base substrate 508. The removed portions associated with the electrode array 526 are based on the master pattern 518. In some examples, the removed portions match the open portions of the mask 516.

Returning to FIG. 8, after the portion 522 undergoes laser ablation at the laser ablation station 514 to form the electrode array 526, the portion 522 is moved, via rotation of the first through third rollers 502, 504, 506, to a printer 528. In the first example assembly 500, the printer 528 includes an apparatus or an instrument capable of applying at least one layer of material 530 having a hydrophobic and/or a dielectric property to the electrode array 526. In the first example assembly 500, the printer 528 can deposit the hydrophobic and/or dielectric material 530 via deposition techniques including, but not limited to, web-based coating (e.g., via rollers associated with the printer 528), slot-die coating, spin coating, chemical vapor deposition, physical vapor deposition, and/or atomic layer deposition. The printer 528 can also apply other materials in addition to the hydrophobic and/or dielectric material 530 (e.g., anti-fouling coatings, anti-coagulants). Also, the printer 528 can apply one or more layers of the material(s) with different thicknesses and/or covering different portions of the base substrate 508.

As described above, in the first example assembly 500, at least one of the first through third rollers 502, 504, 506 advance the base substrate 508 to the printer 528 for application of the hydrophobic and/or dielectric material 530 to the electrode array 526. In some examples, the printer 528 includes a plurality of registration rollers 531 to facilitate accuracy in feeding and registration of the base substrate 508 as part of operation of the printer 528 in applying the hydrophobic and/or dielectric material 530, for example, via roller coating methods.

In the first example assembly 500, the hydrophobic and/or dielectric material 530 is applied to the electrode array 526 to completely or substantially completely insulate the electrode array 526.

In some examples, the hydrophobic and/or dielectric material 530 is deposited via the printer 528 in substantially liquid form. To create a structural or treated layer 532 on the base substrate 508 to support a droplet, the portion 522 is moved via the rollers (e.g., the first through third rollers 502, 504, 506) through a curing station 534. At the curing station 534, the hydrophobic and/or dielectric material is treated and/or modified to form the first treated layer 532. Treating and/or modifying the hydrophobic and/or dielectric material can include curing the material. For example, at the curing station 534, heat is applied to facilitate the hardening of the hydrophobic and/or dielectric material 530. In some examples, the portion 522 is exposed to an ultraviolet light to cure the hydrophobic and/or dielectric material 530 and form the treated layer 532 to insulate the electrode array 526. In other examples, the curing and/or modification of the hydrophobic and/or dielectric material is accomplished without heat and/or a photon source. In some examples, the treated layer 532 supports a droplet as an electric field is applied (e.g., in connection with electrode array 526) to manipulate the droplet. For example, during an electrowetting process, a contact angle of the droplet with respect to the treated layer 532 changes as a result of an applied voltage, which affects the surface tension of the droplet on the treated surface 532. Electrowetting is merely exemplary, the droplet may be moved using other forces as well.

After passing through the curing station 534, the portion 522 is prepared to serve as a bottom substrate of a droplet actuator and/or as a digital microfluidic chip. Because the base substrate 508 includes the non-conductive first layer 510 bonded with the conductive second layer 512, as disclosed above, additional adhesion of, for example the electrode array 526 to the non-conductive first layer 510 is not required. Such a configuration increases the efficiency of the preparation of the base substrate 508 for the droplet actuator by reducing processing steps. Also, as described above, when the portion 522 is at any one of the laser ablation station 514, the printer 528, or the curing station 534, other portions of the base substrate 508 are concurrently moving through the others of the respective stations 514, 528, 534 of the first example assembly 500. For example, when the portion 522 is at the curing station 534, the first through third rollers 502, 504, 506 are continuously, periodically, or aperidiocally advancing one or more other portions of the base substrate 508 through, for example, the laser ablation station 514 and/or the printer 528. In such a manner, preparation of the base substrate 508 for the droplet actuator is achieved via a substantially continuous, high-speed, automated process.

After the curing step, a pattern roller is rolled over a second portion of the base substrate to create an array of wells 540. The array wells 540 may subsequently be coated with a hydrophilic material (not shown).

Although the base substrate 508 may be considered as including successive portions, during some example operations of the first example assembly 500, the base substrate 508 remains as a single sheet as the successive portions undergo processing to create the electrode arrays 526 (e.g., via the electrode pattern) and receive the coating of hydrophobic and/or dielectric material 530. Thus, to create one or more droplet actuators using the processed base substrate 508, the base substrate 508, in some examples, is cut (e.g., diced) to form individual units comprising the electrode arrays 526, as will be further disclosed below. In some examples, prior to dicing, the base substrate 508, including the portion 522, is rewound in a rolled configuration similar to the initial rolled configuration of the base substrate 508 prior to being unwound by the first roller 502. Such rewinding may be accomplished via one or more rollers as part of the roll-to-roll processing. In such examples, the base substrate 508 may be diced or otherwise separated at a later time. In other examples, the rollers (e.g., the second and third rollers 504, 506), advance the base substrate 508 for merging with a top substrate.

Figure 9:
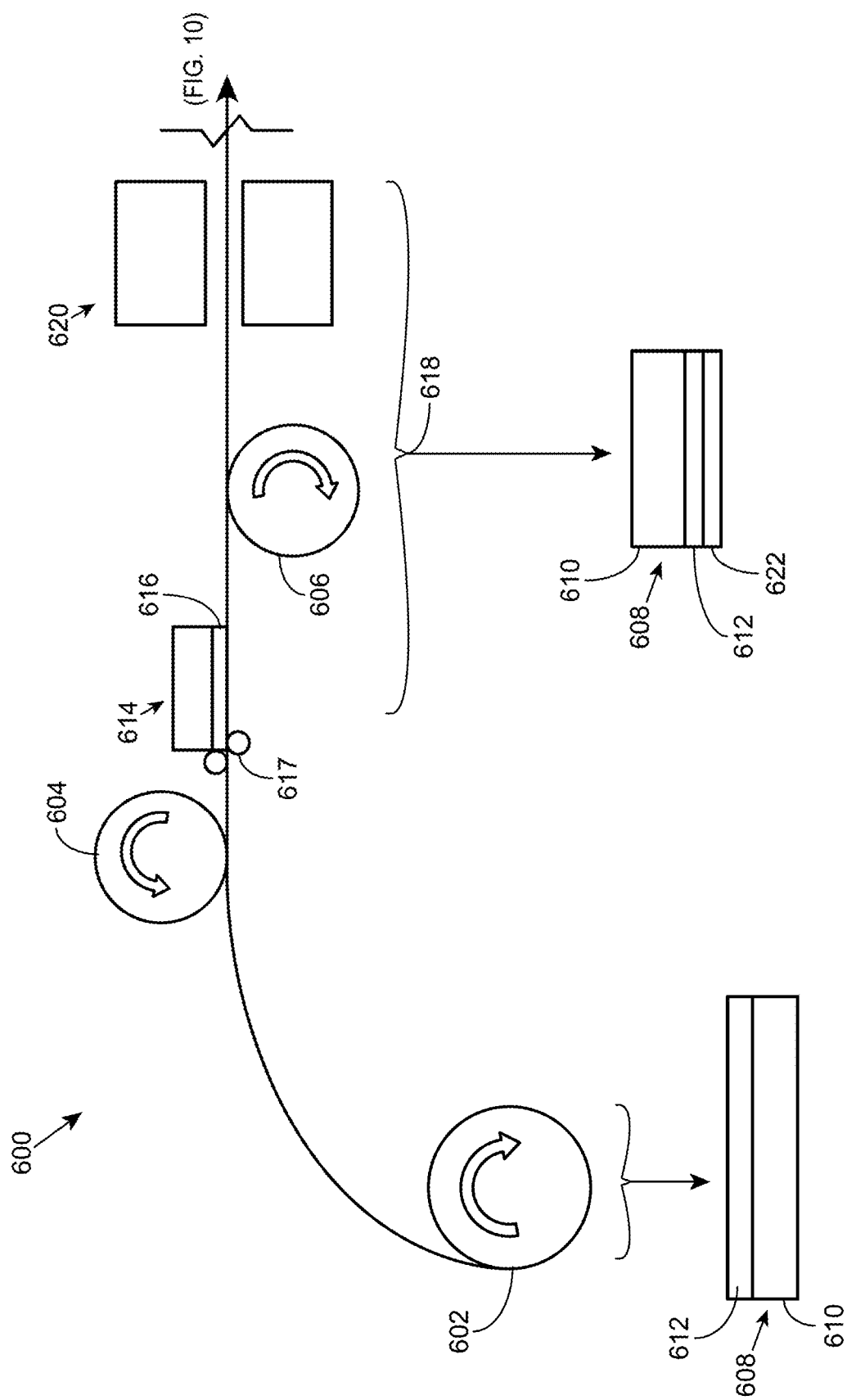
FIG. 9 illustrates an example of fabricating a first (e.g., top) substrate of the digital microfluidic and analyte detection device.

FIG. 9 illustrates a second example assembly 600 for creating an example top substrate of a droplet actuator having a single electrode. The second example assembly 600 includes a series or a plurality of rollers, including a first roller 602, a second roller 604, and a third roller 606, which operate in synchronized rotation to drive a top substrate 608 through the second example assembly 600. The second example assembly 600 can include rollers in addition to the first through third rollers 602, 604, 606 to move the top substrate 608 through the assembly 600.

In the second example assembly 600, the first roller 602 rotates to unwind the top substrate 608, which, in some examples, is a sheet in a rolled configuration. The example top substrate 608 of FIG. 9 includes a first layer 610 and a second layer 612. As with the example base substrate 508, in this example, the example first layer 610 of the top substrate 608 comprises a non-conductive material such as, for example, a plastic, and the example second layer 612 includes a conductive material, such as a metal including, for example, one or more of gold, chrome, silver, indium tin oxide, or copper and/or any other suitable metal(s), conductive polymer(s), or combination(s) of metal(s) and/or conductive polymer(s). In some examples, the conductive second layer 612 is adhered to the nonconductive first layer via an adhesive layer (e.g., chrome).

In the second example assembly 600, the first through third rollers 602, 604, 606 rotate to advance the top substrate 612 to a printer 614. The printer 614 coats the conductive second layer 612 with a hydrophobic and/or dielectric material 616 (e.g. Teflon® or parylene C, or a dielectric such as a ceramic). The printer 614 is substantially similar to the printer 528 of the first example assembly 500 of FIG. 8. For example, the printer 614 can apply the hydrophobic and/or dielectric material 616 to the top substrate 608 via web-based coating, slot-die coating, spin coating, chemical vapor deposition, physical vapor deposition, atomic layer deposition, and/or other deposition techniques. The printer 614 can include registration rollers 617 to facilitate alignment of the top substrate 608 with respect to the printer 614 during application of the hydrophobic and/or dielectric material 616 and/or other coating materials.

After receiving the coating of the hydrophobic and/or dielectric material 616, the second roller 504 and the third roller 506 advance the portion 618 to a curing station 620. As disclosed in connection with the curing station 534 of FIG. 8, the curing station 620 of the second example assembly 600 facilitates the modification (e.g., curing) of the hydrophobic material via heat to form a treated layer 622. The treated layer 622 insulates the conductive second layer 612, which serves as the single electrode of the top substrate 608, by completely or substantially completely covering the conductive second layer 612. Thus, in coating the second layer 612 of the portion 618, electrical potential conducting portion of the top substrate 608 is insulated from a droplet that may be applied to a droplet actuator that includes the portion 618.

After passing through the curing station 620, the portion 618 is prepared to serve as a top substrate of a droplet actuator. Because the top substrate 608 includes the non-conductive first layer 610 pre-adhered to the conductive second layer 612, additional adhesion of, for example, an electrode to the non-conductive first layer 610 is not required, thereby increasing the efficiency of the preparation of the top substrate 608 for the droplet actuator.

In the second example assembly 600, the first through third rollers 602, 604, 606 rotate to advance the top substrate 608 such that portions of the top substrate pass through one of the printer 614 or the curing station 620 in substantially continuous, periodic and/or aperiodic succession as part of the roll-to-roll operation of the second example assembly 60. Thus, although the second example assembly 600 is described in association with the portion 618, it is to be understood that successive portions of the top substrate 608 are prepared in substantially the manner as the portion 618 as a result of rotation of the first through third rollers 602, 604, 606. In such as manner, the top substrate 308 is provided with a treated layer 622 along the length of the top substrate 608.

In the example top substrate 608, the conductive second layer 612 serves an electrode. However, in some examples, the conductive second layer 612 undergoes laser ablation to form one or more electrode arrays. In such examples, the second example assembly 600 includes a laser ablation station. Thus, prior to receiving the hydrophobic material 616, the top substrate 608 is exposed to a laser beam, which creates an electrode pattern in the irradiated conductive second layer 612. Also, in some examples, the electrode array is not formed on/in the base substrate but only on/in the top substrate 608.

During operation of the second example assembly 600, the top substrate remains single sheet as successive portions of the top substrate 608 are coated with the hydrophobic material 616. As part of the fabrication of one or more droplet actuators, the top substrate 608 is aligned with the base substrate. In some examples, after passing through the curing station 620, the top substrate is rewound into a rolled configuration via one or more rollers. In such examples, the finished roll may be diced or otherwise cut and/or separated into individual units that are aligned at a spaced apart distance and bonded with individual diced units of the base substrate to create a droplet actuator.

In other examples, after passing through the curing station 620, the rollers (e.g., the first through third rollers 602, 604, 606) continue to advance the top substrate 608 to merge the top substrate 608 with the base substrate via automated roll-to-roll processing. In such examples, to prepare the top substrate 608 for alignment with the base substrate 508, the first through third rollers 602, 604, 606 rotate so as to reverse the orientation of the top substrate relative to the base substrate such that the treated layer of the base substrate faces the treated layer 622 of the top substrate 608 when the base substrate 508 and the top substrate 608 are aligned in parallel configuration.

As show in FIG. 10, the third example assembly 650 includes a third roller 656 and a fourth roller 608 that form a pair of merging rollers to which the base substrate 508 and the top substrate 608 are fed via the respective first roller 652 and the second roller 654 of the third example assembly 650. As each of the merging rollers 656, 658 rotates, the base substrate 658 and the top substrate 658 are aligned in a parallel configuration at a predetermined spaced apart distance, or gap.

The example third assembly 650 includes a bonding station 664. The bonding station 664 joins, or bonds, the base substrate 508 and the top substrate 608 as part of fabricating the droplet actuator. For example, at the bonding station 664, one or more adhesives may be selectively applied to a predefined portion of the base substrate 508 and/or the top substrate 608 (e.g., a portion of the base substrate 508 and/or the top substrate 608 defining a perimeter of the resulting droplet actuator) to create a bond between the base substrate 508 and the top substrate 608 while preserving the gap 662. In some examples, bonding the substrates 508, 608 at the bonding station 664 including forming the gap 662 (e.g., in advance of applying the adhesive).

Examples of adhesive(s) that may be used at the bonding station 664 include epoxies, foils, tapes, and/or ultraviolet curable adhesives. In some examples, layers of polymers such as SU-8 and/or polydimethylsiloxane (PDMS) are applied to the base substrate 508 and/or the top substrate 608 to bond the substrates. Also, in some examples, the bonding station 664 provides for curing of the adhesive(s) via, for example, ultraviolet light. The bonding station 664 may apply one more methods involving, for example, heat (e.g. thermal bonding), pressure, curing, etc. to bond the base substrate 658 and the top substrate 608.

In the example third assembly 650, the merged portion 660 can be selectively cut, diced or otherwise separated to form one or more droplet actuators, as substantially represented in FIG. 10 by the merged portion 660. The example third assembly 650 includes a dicing station 666. The dicing station 666 can be, for example, a cutting device, a splitter, or more generally, an instrument to divide the continuous merged portion 660 into discrete units corresponding to individual droplet actuators. The merged portion 660 may be cut into individual droplet actuators based on, for example, the electrode pattern such that each droplet actuator includes a footprint of the electrode array and the other electrodes that are formed via the electrode pattern.

Figure 11B:
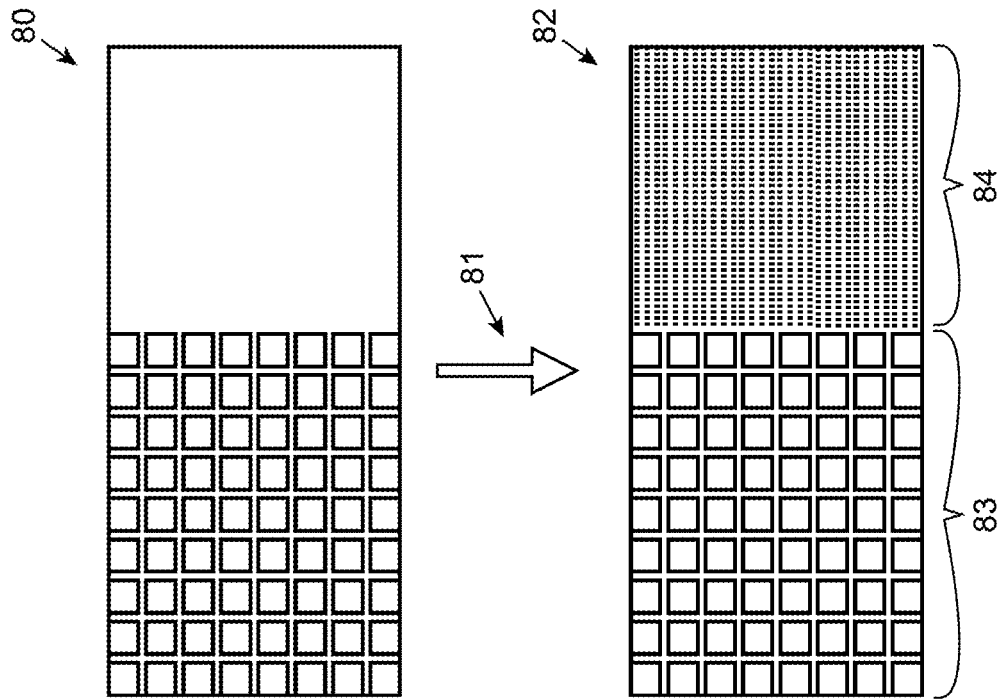
FIG. 11A and FIG. 11B show a view from the top of a bottom substrate of exemplary digital microfluidic and analyte detection devices of the present disclosure.
Figure 11A:
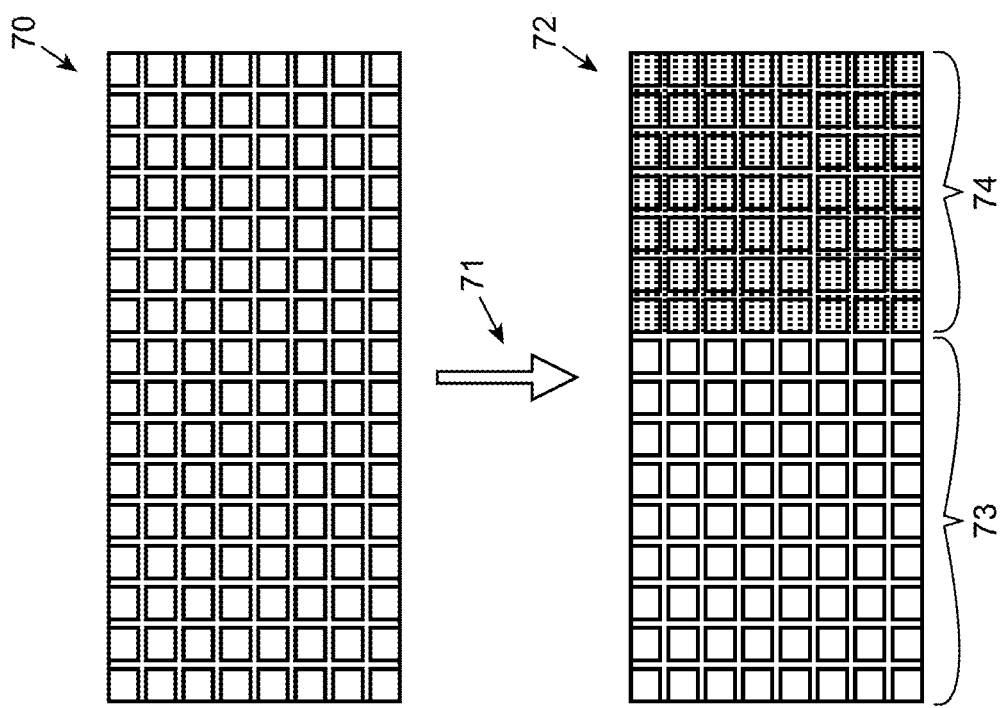

FIG. 11A depicts a top view of the bottom substrate 70 on which an array of electrodes is present in the first portion 73 and second portion 74. The bottom substrate 72, after step 71 of fabrication of an array of wells on the second portion, is shown. FIG. 11B depicts a top view of a bottom substrate 80 with an array of electrodes disposed only in the first portion 83. The bottom substrate 82 is depicted after the step 81 in which an array of wells is formed in the second portion 84.

Figure 12A:
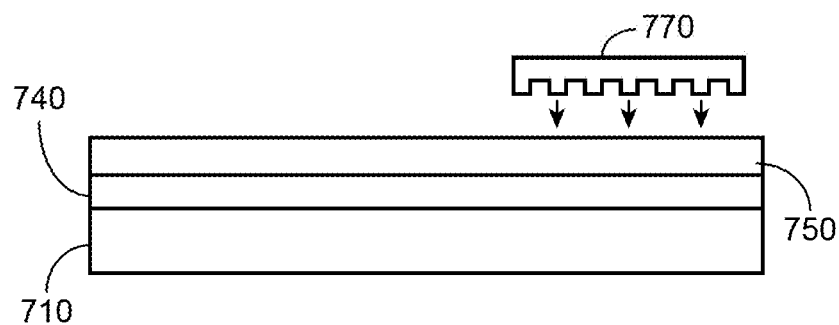
FIGS. 12A-12D illustrate examples of fabricating the array of wells into the integrated digital microfluidic and analyte detection device.

The well array may be fabricated onto the dielectric/hydrophobic layer, hydrophobic layer (if present), or hydrophilic layer (if present). One exemplary method for fabricating a well array onto the hydrophobic layer of the first substrate uses thermal or ultraviolet nanoimprint lithography. FIG. 12A illustrates one exemplary method for fabricating a well array by utilizing a flat nanoimprint mold 770 to apply sufficient pressure to the hydrophobic layer 750 at the second portion of the first substrate 710 in order to form the well array 760 pattern. In this example, the nanoimprint stamper may be a flat stamping element whose stamping contours correspond to the upper surface of the second layer.

Figure 12B:
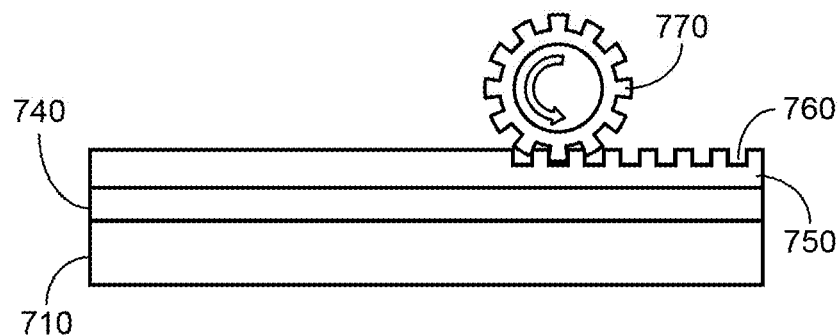

FIG. 12B illustrates another exemplary method in which a nanoimprint roller 775 may be utilized to apply the pattern of well arrays to the hydrophobic layer of the second portion of the first substrate. The nanoimprint roller may imprint the pattern onto the hydrophobic layer 750 of the first substrate 710 by advancing the roller 775 in one direction. As the roller advances in the one direction, the roller leaves behind an imprint of a pattern of the well array 760 that corresponds to the imprint pattern on the roller. In one example, the roller 775 rolls in a counter clock-wise direction as the roller 775 imprints pattern onto the hydrophobic layer 750 of the first substrate 710. It is understood that the roller or stamper may be changed to form wells of suitable volume, for example, a femtolitre roller or stamper may be used for forming femtoliter wells.

Figure 12C:
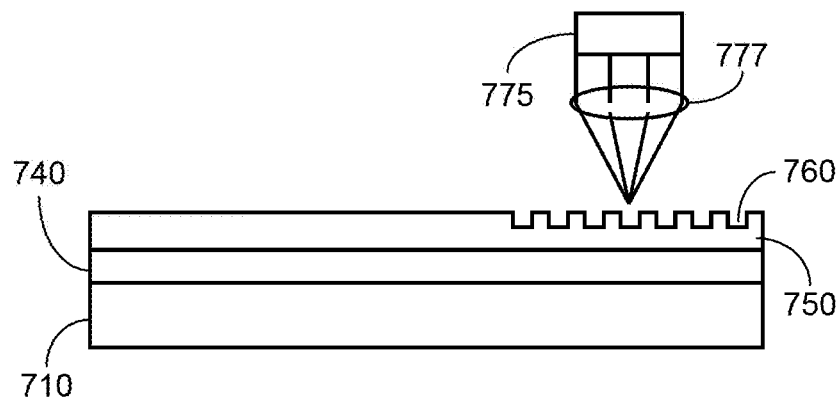

FIG. 12C illustrates another exemplary method of forming a pattern of well arrays to the hydrophobic layer of the second portion of the first substrate. In this example, a laser may be applied to ablate the upper surface of the hydrophobic layer 750. The laser ablation step can produce a well array 760 pattern on the second layer. Some examples of suitable lasers for ablating the second layer include parameters with femtosecond and picosecond lasers. In some examples, the laser ablation step includes use of a special mask to define the well array pattern required. In some examples, the laser 775 utilizes a focusing element 777 (e.g., lens) to accurately target and ablate the pattern. In some examples, following the laser ablation step, the well array may be coated with a dielectric and/or hydrophobic layer.

Figure 12D:
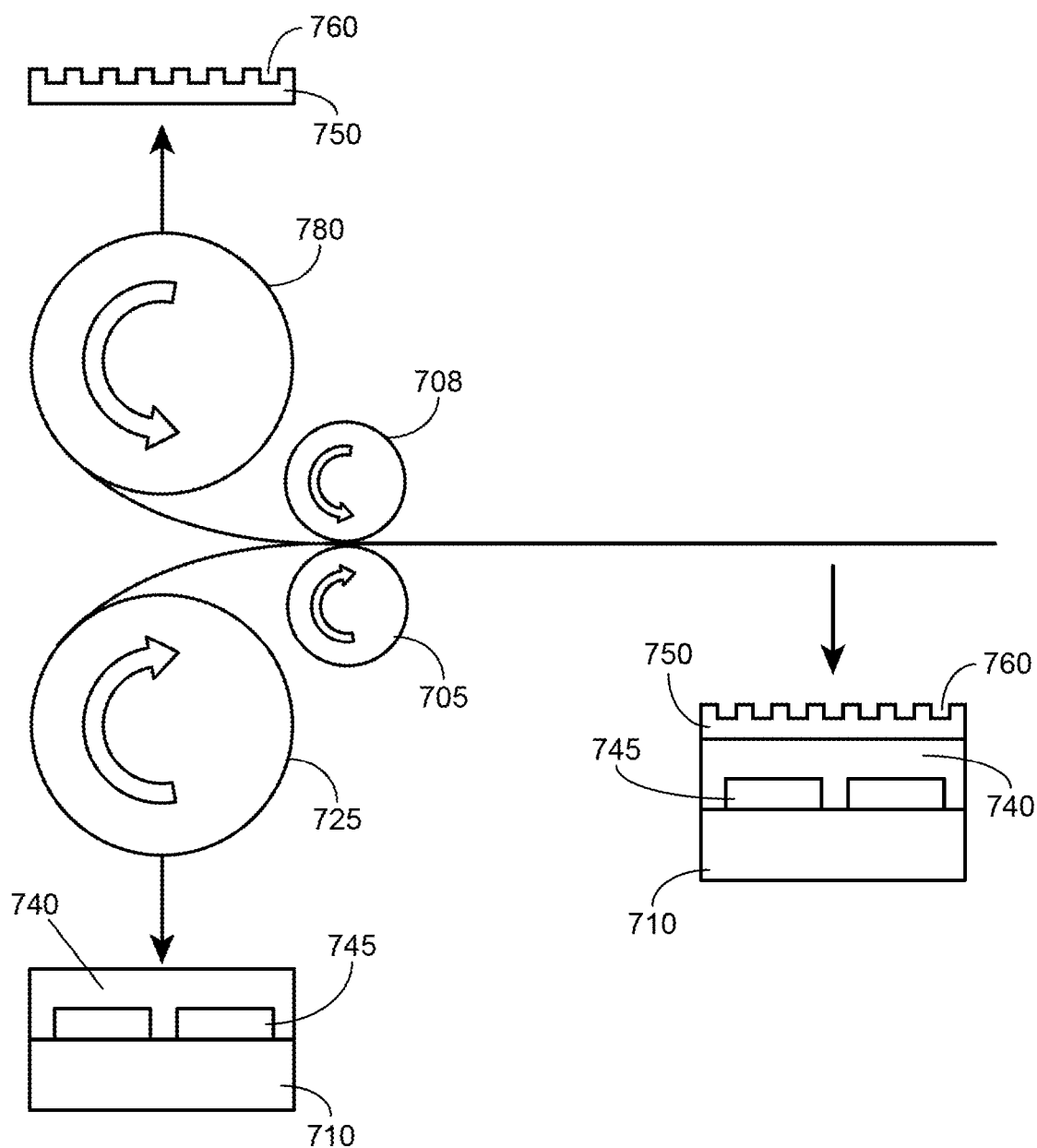

FIG. 12D illustrates yet another example of forming a pattern of well arrays 760 onto the dielectric layer 740 of the second portion of the first substrate 710. As illustrated in FIG. 12D, the method utilizes roll-to-roll fabrication to separately fabricate microfluidic component and the well array. In one example, a first roll 725 contains a microfluidic component, which includes the first substrate 710, where the first substrate comprises a series or plurality of electrodes 745, and a dielectric layer 740 disposed over the upper surface of the first substrate and covering the series or plurality of electrodes 745. A second roll 780 contains a substrate 750 with the pattern of well array 760 already included on the substrate. In some examples, the pattern of well array 760 previously included on the substrate 750 can be applied through thermal or UV nanoimprint lithography. In other examples, the pattern of well array can be previously included on the substrate through laser ablation. As illustrated in FIG. 12D, the imprinted second roll 780 may also include a hydrophobic coating imprinted onto the substrate of the well array. The separate rolls are unwound via rollers 705 and 708, and then subject to a lamination process where the two films may be laminated together by overlying the well substrate over the microfluidic component substrate to form a stacked configuration of the well array and microfluidic components.

As described herein, "roll-to-roll" may include the equivalent term "reel-to-reel" and operates by moving a substrate through various components at high speeds, including, for example, rates of meters per second. Roll-to-roll assemblies facilitate the unwinding of a rolled substrate, the advancement of the substrate through the components, and the rewinding of the processed substrate into a roll.

As previously noted, the detection module formed by the second portions of the first and second substrates is used for detecting an analyte related signal. In some examples, detection of the analyte or biological sample of interest may occur through optical signal detection. For example, shining an excitation light (e.g., laser) in order to measure the signal intensity result. In other examples, the analyte desired may be detected by measuring an optical signal emanating from each well chamber and quantified by quantifying the result. For example, the number of positive counts (e.g., wells) is compared to the number of negative counts (e.g., wells) via digital analysis. A variety of signals from the wells of the device may be detected. Exemplary signals include fluorescence, chemiluminescence, colorimetric, turbidimetric, etc.

Figure 15:
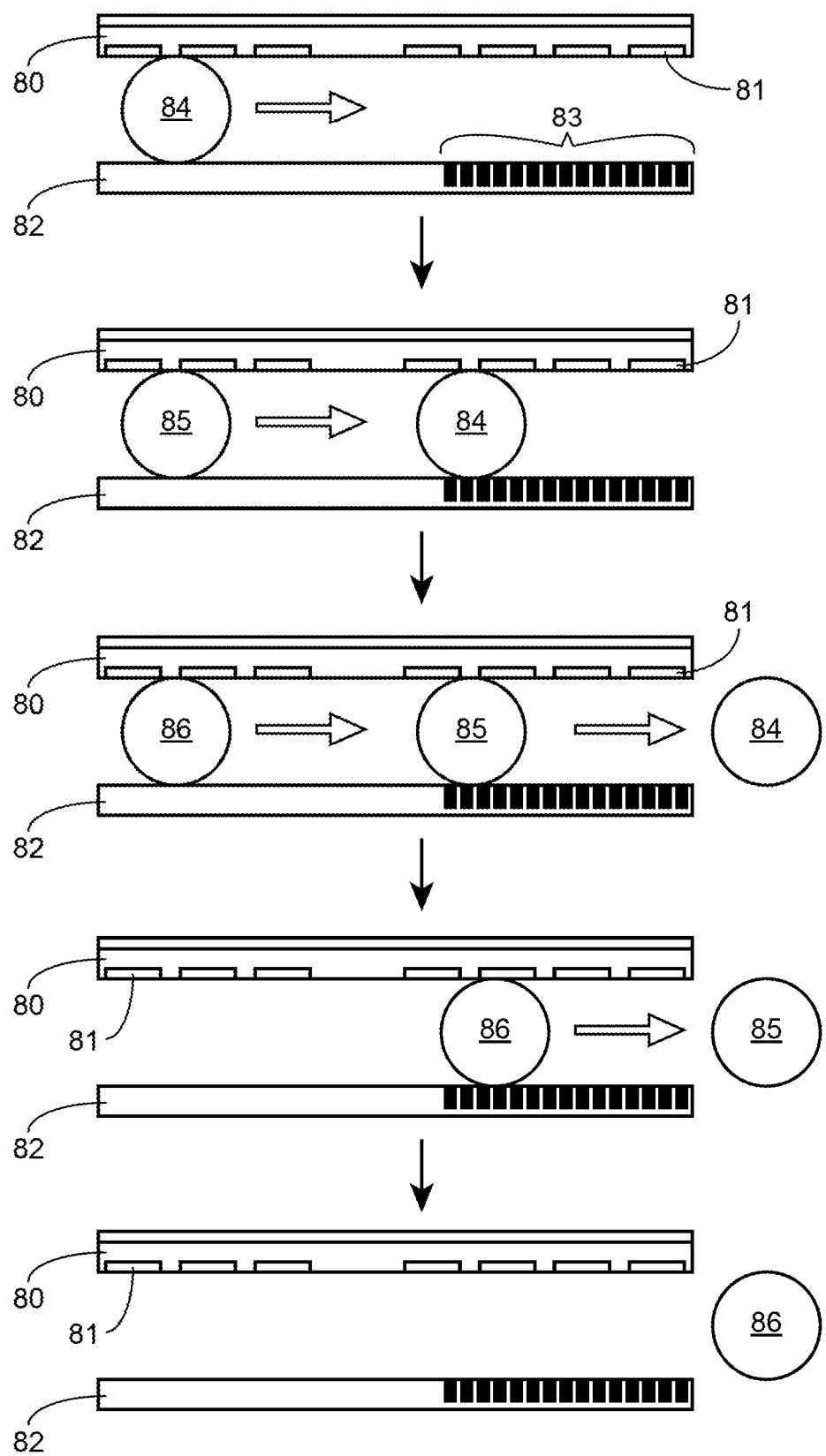
FIG. 15 depicts an exemplary method of the present disclosure.

The devices described herein may be used to generate an analyte related signal and quantitate the signal. Exemplary method is depicted in FIG. 15. The device in FIG. 15 includes a top substrate 80 with an array of electrodes 81. The top substrate is positioned in a spaced apart manner from the bottom substrate 82 which includes an array of wells 83 in a second portion of the device. A droplet 84 containing particles or beads or analyte molecules (not shown) may be moved to the array of wells 83 using the electrodes 81. After a sufficient period of time to allow the particles or beads or analyte molecules to move into the wells, the droplet 84 may be moved to a waste chamber/absorption pad and the like. A droplet of buffer 85 may then be moved to the array of wells to remove any particles or beads not deposited into the wells. In some cases, the buffer droplet may push the droplet 84 over to the waste chamber. A droplet of immiscible fluid 86 may be moved over the array of wells and seal the wells. Any excess droplet 86 may be removed prior to optically interrogating the wells.

Figure 16:
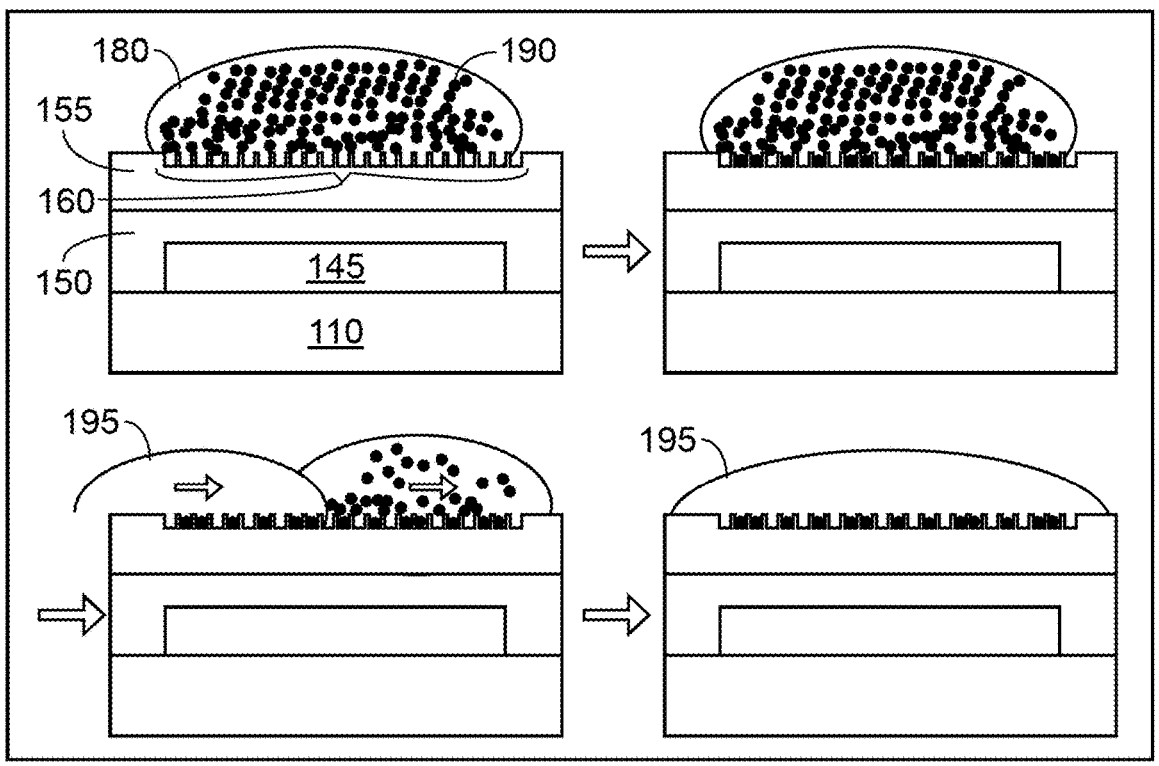
FIG. 16 illustrates an exemplary method for removing beads not located in the wells of the depicted device.

FIG. 16 depicts a method in which the digital microfluidics electrodes (e.g. electrode 145) position the droplet 180 containing particles/beads or analyte molecules 190 over the array of wells 160. After a period of time sufficient for deposition of particles/beads/analyte molecules into the wells, the droplet is displaced by a droplet of immiscible liquid 195 (or an immiscible liquid as explained herein). The droplet of immiscible liquid functions to move droplet 180 with any bead/particles/analyte molecules not deposited into the wells away from the wells and to cover the wells.

Figure 17:
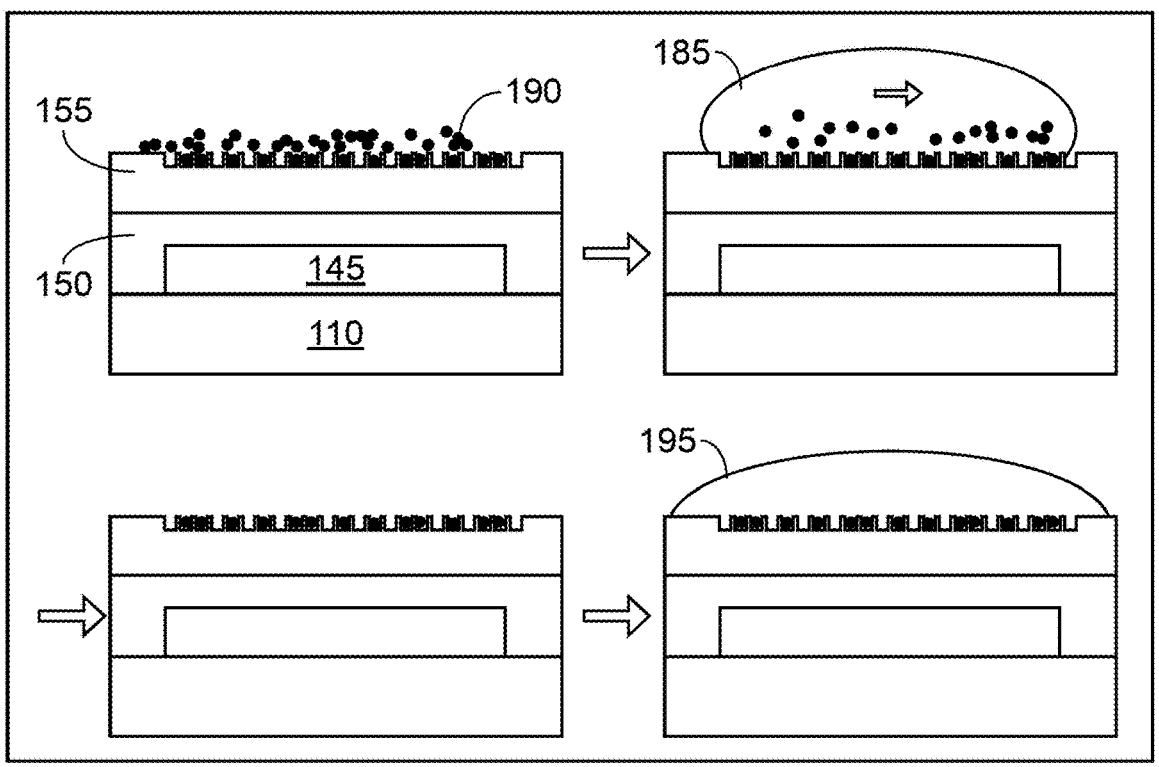
FIG. 17 illustrates another exemplary method for removing beads not located in the wells of the depicted device.

FIG. 17 depicts another method for removing any beads not deposited into wells. In FIG. 17, many beads 190 are remaining over the wells after removal of the droplet containing the beads. These beads are washed away using an aqueous droplet. 185 After removal of the aqueous droplet, the array of wells contains the deposited beads. An immiscible fluid 195 is then moved over the array of wells to seal the wells.

A number of forces may be utilized to facilitate the movement of particles/beads from a droplet positioned over the array of wells into the wells. Such forces include gravity, electrical force, magnetic force, etc. Permanent magnets or electromagnets may be used as source of magnetic force. In certain embodiments, the magnets are not located on the integrated microfluidic and detection chip. Analyte molecules may be deposited into the wells via diffusion.

Variations on Methods and on Use of the Device

The disclosed methods of determining the presence or amount of analyte of interest present in a sample, and the use of the microfluidics device, may be as described above. The methods and use of the disclosed microfluidics device may also be adapted in view of other methods for analyzing analytes. Examples of well-known variations include, but are not limited to, immunoassay, such as sandwich immunoassay (e.g., monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

Immunoassay

The analyte of interest, and/or peptides or fragments thereof, may be analyzed using an immunoassay. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, a detectable label (e.g., such as one or more fluorescent labels one or more tags attached by a cleavable linker (which can be cleaved chemically or by photocleavage)) is attached to the capture antibody and/or the detection antibody.

A heterogeneous format may be used. For example, after the test sample is obtained from a subject, a first mixture is prepared. The mixture contains the test sample being assessed for analyte of interest and a first specific binding partner, wherein the first specific binding partner and any analyte of interest contained in the test sample to form a first specific binding partner-analyte of interest complex. Preferably, the first specific binding partner is an anti-analyte of interest antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a nanobead, a microbead, a nanoparticle, a microparticle, a membrane, a scaffolding molecule, a film, a filter paper, a disc, or a chip (e.g., a microfluidic chip).

After the mixture containing the first specific binding partner-analyte of interest complex is formed, any unbound analyte of interest is removed from the complex using any technique known in the art. For example, the unbound analyte of interest can be removed by washing. Desirably, however, the first specific binding partner is present in excess of any analyte of interest present in the test sample, such that all analyte of interest that is present in the test sample is bound by the first specific binding partner.

After any unbound analyte of interest is removed, a second specific binding partner is added to the mixture to form a first specific binding partner-analyte of interest-second specific binding partner complex. The second specific binding partner is preferably an anti-analyte of interest (such as an antibody) that binds to an epitope on analyte of interest that differs from the epitope on analyte of interest bound by the first specific binding partner. Moreover, also preferably, the second specific binding partner is labeled with or contains a detectable label (e.g., a detectable label, a tag attached by a cleavable linker, etc.).

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

Sandwich Immunoassay

A sandwich immunoassay measures the amount of antigen between two layers of antibodies (i.e., a capture antibody (i.e., at least one capture antibody) and a detection antibody (i.e. at least one detection antibody)). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a test sample. More specifically, the at least two antibodies bind to certain epitopes of analyte of interest or an analyte of interest fragment forming an immune complex which is referred to as a "sandwich". One or more antibodies can be used to capture the analyte of interest in the test sample (these antibodies are frequently referred to as a "capture" antibody or "capture" antibodies), and one or more antibodies with a detectable label (e.g., a fluorescent label, a tag attached by a cleavable linker, etc.) that also bind the analyte of interest (these antibodies are frequently referred to as the "detection" antibody or "detection" antibodies) can be used to complete the sandwich. In some embodiments, an aptamer may be used as the second binding member. In a sandwich assay, the binding of an antibody to its epitope desirably is not diminished by the binding of any other antibody in the assay to its respective epitope. In other words, antibodies are selected so that the one or more first antibodies brought into contact with a test sample suspected of containing analyte of interest do not bind to all or part of an epitope recognized by the second or subsequent antibodies, thereby interfering with the ability of the one or more second detection antibodies to bind to the analyte of interest.

In one embodiment, a test sample suspected of containing analyte of interest can be contacted with at least one capture antibody (or antibodies) and at least one detection antibodies either simultaneously or sequentially. In the sandwich assay format, a test sample suspected of containing analyte of interest (such as a membrane-associated analyte of interest, a soluble analyte of interest, fragments of membrane-associated analyte of interest, fragments of soluble analyte of interest, variants of analyte of interest (membrane-associated or soluble analyte of interest) or any combinations thereof)) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the test sample.

Optionally, prior to contacting the test sample with the at least one first capture antibody, the at least one capture antibody can be bound to a solid support which facilitates the separation the antibody-analyte of interest complex from the test sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the test sample suspected of containing analyte of interest is brought into contact with the at least one capture antibody, the test sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a detectable label (e.g., a fluorescent label, a tag attached by a cleavable linker, etc.). The detectable label can be bound to the at least one detection antibody prior to, simultaneously with or after the formation of the capture antibody (antibodies)-analyte of interest-detection antibody (antibodies) complex. Any detectable label known in the art can be used, e.g., a fluorescent label, a cleavable linker as discussed herein, and others known in the art.

The order in which the test sample and the specific binding partner(s) are added to form the mixture for assay is not critical. If the first specific binding partner is detectably labeled (e.g., a fluorescent label, a tag attached with a cleavable linker, etc.), then detectably-labeled first specific binding partner-analyte of interest complexes form. Alternatively, if a second specific binding partner is used and the second specific binding partner is detectably labeled (e.g., a fluorescent label, a tag attached with a cleavable linker, etc.), then detectably-labeled complexes of first specific binding partner-analyte of interest-second specific binding partner form. Any unbound specific binding partner, whether labeled or unlabeled, can be removed from the mixture using any technique known in the art, such as washing.

Next, signal, indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

Provided herein are methods for measuring or detecting an analyte of interest present in a biological sample. In such methods, a sample droplet containing the target analyte of interest may be merged with a droplet containing beads (such as magnetic beads) on which a first specific binding partner that specifically binds to the target analyte of interest present in the sample is attached. Merging creates a single droplet which may be incubated for a time sufficient to allow binding of the first specific binding partner to an analyte of interest present in the sample droplet. Optionally, the single droplet may be agitated to facilitate mixing of the sample with the first specific binding partner. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away to a waste chamber or pad and replaced with a droplet containing a second binding member. The second specific binding partner may be detectably labeled. The label may be any label that can be optically detected. For example, the label may be a fluorescent label. An optional wash step may be performed, prior to adding the second binding member, by moving a droplet of wash buffer to the location at which the beads are retained using the force, e.g., magnetic. The beads may or may not be resuspended in the wash buffer. If magnetic beads are used, a magnetic force can be applied to the magnetic beads and the wash buffer is transported to a waste location. After a period of time sufficient for the second specific binding partner to bind the analyte of interest bound to the first binding member, the droplet containing the second specific binding partner may be moved away while the beads are retained at the location. The beads may be washed using a droplet of wash buffer. Following the wash step, a droplet containing the labeled beads which has a complex of the first binding member, analyte of interest and the second binding partner may be moved over to the detection module (such as by removal of the magnetic force if magnetic beads are used). As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using a hydrophobic liquid.

Forward Competitive Inhibition

In a forward competitive format, an aliquot of labeled analyte of interest (e.g., analyte having a fluorescent label, a tag attached with a cleavable linker, etc.) of a known concentration is used to compete with analyte of interest in a test sample for binding to analyte of interest antibody.

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

Provided herein are methods for measuring or detecting an analyte of interest present in a biological sample. In such methods, a sample droplet containing the target analyte of interest may be merged with a droplet containing magnetic beads on which a first specific binding partner that specifically binds to the target analyte of interest present in the sample is attached and analyte labeled with a detectable label (such as a fluorescent label). Optionally, the single droplet may be agitated to facilitate mixing of the sample with the first specific binding partner and the labeled analyte. Mixing may be achieved by moving the single droplet back and forth, moving the single droplet around over a plurality of electrodes, splitting a droplet and then merging the droplets, or using SAWs, and the like. Next, the single droplet may be subjected to a force (such as a magnetic force) to retain the beads at a location in the device while the droplet may be moved away to a waste chamber or pad and replaced with a droplet containing a second binding member. An optional wash step may be performed by moving a droplet of wash buffer to the location at which the beads are retained using the magnetic force. The beads may or may not be resuspended in the wash buffer; a force is applied to the beads (such as a magnetic force if magnetic beads are used) and the wash buffer is transported to a waste location. After a period of time sufficient for the first specific binding partner to bind to the analyte of interest, the droplet may be moved away while the beads are retained at the location. Following the optional wash step, a droplet containing the labeled beads which has a complex of the first binding member and analyte of interest may be moved over to the detection module (such as by removing a magnetic force if magnetic beads are used). As explained herein, the immunoassay may be carried out in the sample preparation module. The labeled beads may be allowed to settle into the array of wells in the detection module. The beads may settle using gravitational force or by applying a force, e.g., electric or magnetic. Following a wash step to remove any beads not located inside the wells, the wells may be sealed by using a hydrophobic liquid.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

Reverse Competition Assay

In a reverse competition assay, an immobilized analyte of interest can either be sequentially or simultaneously contacted with a test sample and at least one labeled antibody.

Provided herein are methods for measuring or detecting an analyte of interest present in a biological sample. In such methods, a sample droplet containing the target analyte of interest may be merged with a droplet containing a first specific binding partner that specifically binds to the target analyte of interest present in the sample and is labeled with a detectable label (such as a fluorescent label, enzymatic label, etc.) and magnetic beads to which the analyte of interest is attached. Merging creates a single droplet which may be incubated for a time sufficient to allow binding of the first specific binding partner to an analyte of interest present in the sample droplet. Optionally, the single droplet may be agitated to facilitate mixing of the sample with the first specific binding partner. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away to a waste chamber or pad and replaced with a droplet containing a second binding member. An optional wash step may be performed by moving a droplet of wash buffer to the location at which the beads are retained using the magnetic force. The beads may or may not be resuspended in the wash buffer; a magnetic force is applied to the magnetic beads and the wash buffer is transported to a waste location. After a period of time sufficient for the first specific binding partner to bind the analyte of interest bound, the magnetic force may be removed and a droplet containing the labeled beads which has a complex of the first binding member, analyte of interest may be moved over to the detection module. As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using a hydrophobic liquid.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

One-Step Immunoassay or "Capture on the Fly"

In a capture on the fly immunoassay, a solid substrate is pre-coated with an immobilization agent. The capture agent, the analyte and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is strepativdin, the ligand on the first specific binding member may be biotin) and also binds to the analyte of interest. The second specific binding member comprises a detectable label and binds to an analyte of interest. The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected.

The use of a capture on the fly assay can be done in a variety of formats as described herein, and known in the art. For example the format can be a sandwich assay such as described above, but alternately can be a competition assay, can employ a single specific binding member, or use other variations such as are known.

Combination Assays (Co-Coating of Microparticles with Ag/Ab)

In a combination assay, a solid substrate, such as a microparticle is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods and devices disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacteria, or a portion thereof. The methods and devices also may be used for measuring analyte present in a biological sample. The methods and devices also may be used in blood screening assays to detect a target analyte. The blood screening assays may be used to screen a blood supply.

Surface Acoustic Wave Device, System, and Methods

Systems, device, and methods related to an integrated surface acoustic wave (SAW) sample preparation and analyte detection device are provided by the subject disclosure.

In one example, the device includes a sample preparation component, e.g., a substrate with a surface that allows for liquid or fluids to propagate across the surface thereof via manipulation by acoustic forces. In the same example, the device includes an analyte detection component configured to receive the propagated liquid and perform analyte detection on the received liquid.

"Surface acoustic waves (SAW)" and grammatical equivalents thereof as used herein refer generally to propagating acoustic waves in a direction along a surface. "Traveling surface acoustic waves" (TSAWs) enable coupling of surface acoustic waves into a liquid. In some examples, the coupling may be in the form of penetration or leaking of the surface acoustic waves into the liquid. In some examples, the surface acoustic waves are Raleigh waves. Propagation of the surface acoustic waves can be performed by streaming the surface acoustic waves through a liquid. Propagation of surface acoustic waves may be conducted in a variety of different ways and by using different materials, including generating an electrical potential by a transducer, such as a series or plurality of electrodes.

The electrodes may be patterned onto a planar substrate. In some examples, the planar substrate may be a piezoelectric layer. In some examples, the electrodes may be fabricated onto the piezoelectric layer using standard lithography and lift off/wet etching processes. The structure of the electrodes, spacing between electrodes, the number of electrodes (i.e., resolution) on the substrate may vary. In some examples, interdigitated (IDT) transducers or electrodes are used. In some examples, the sample preparation component may include a liquid. In some examples, there may be multiple layers. The different layers may have different arrangement or configuration of scattering structures for scattering surface acoustic waves. As a result, liquid droplet movement across the different layers may differ due to the varied scattering structures present.

In some examples, SAW are propagated when a single transducer or electrode is activated. In other examples, a plurality (e.g., pair) of electrodes fabricated on the substrate surface may generate two traveling SAWs propagating towards each other. In some examples, SAW displacement is activated when a radio frequency (RF) range is applied to the electrodes. Upon being activated, the electrodes or transducers emit an electric potential across the surface of the substrate, where the substrate is subjected to mechanical stress. Examples of mechanical stress are continuous contraction and expansion of the surface of the substrate. As a result of this continuous deformation of the substrate, surface acoustic waves are propagated across the surface.

Surface acoustic waves can be measured according to amplitude and frequency. Therefore, the frequency and amplitude of the electric potential generated by the electrodes is responsible for the amplitude and frequency of SAW.

Propagation of SAW may be in a linear direction. In some examples, SAW may propagate across the longitudinal length of the substrate surface. In other examples, SAW may propagate across the width of the substrate surface. In other examples, propagation of SAW may be in a non-linear direction and motion. Because fluid is a dissipative system, the response to harmonic forcing via SAW may not necessarily be harmonic.

When a TSAW contacts liquid, the liquid absorbs part of the SAW's energy and may refract it in the form of longitudinal waves. Absorption of the refracted acoustic energy induces fluid flow or propagation across the surface of the substrate. When a surface acoustic wave is propagated along the surface of the sample preparation component, the SAW may come into contact with the liquid. As a result of the liquid interacting with SAW, results in the SAW being transferred into the liquid. SAWs manipulate fluid by means of "contact free manipulation", which is meant the liquids are propagated to the detection component by the acoustic waves leaking or penetrating into the fluid. As a result, there is a minimization of outside contamination of the biological sample or analyte.

In some examples, exemplary driving fluid actions includes pumping, mixing, jetting, etc. As a result, the liquid is propagated along the surface of the sample preparation component.

In some examples, the liquid can be dispensed as a droplet to be actuated onto the surface of the sample preparation component prior to the activation of the SAW electrodes. Droplet actuation can be used for positioning droplets and dispensing droplets onto the sample preparation component.

In other examples, instead of liquid droplet-based microfluidics, a SAW driven pump may be used to pump liquid onto the open surface. In some examples, fluid may be pumped through enclosed channels.

The liquid may be any test sample containing or suspected of containing any analyte of interest. As used herein, "analyte", "target analyte", "analyte of interest" refer to the analyte being measured in the methods and devices disclosed herein. The liquid droplets may also refer to particles or beads in an aqueous solution. Samples may include biological fluid samples such as, for example, blood, plasma, serum, saliva, sweat, etc.

In some examples, the liquid can be disposed as a single particle. In other examples, the liquid can be disposed as a group of particles (e.g., thousands of particles). The liquid droplets may vary according to a wide range of length scales, size (nm to mm), as well as shape.

The propagation of surface acoustic waves may also be affected by the presence of phononic structures patterned onto the surface of the sample preparation platform. These phononic structures may control the propagation of the sound acoustic waves. For example, the phononic structures may control the direction, movement, velocity of the SAW; thus, providing enhanced functionality. The phononic structures may be fabricated onto the substrate using standard lithography, lift off/wet etching processes, embossing/nano-imprint lithography, and micromachining, pressure, heat, and laser modification of the substrate to form these phononic structures. These phononic structures may assume a variety of shapes and sizes as well. In some examples, the phononic structures may be pillars, cones, or holes that form a lattice within the substrate.

Surface Acoustic Waves Sample Preparation Component

"Sample preparation component" and grammatical equivalents thereof as used herein refer to a generally planar surface on which the liquid droplets are initially dispersed upon and where steps of immunoassay as described herein may be carried out. In some examples, the substrate may be made of materials with high acoustic reflection.

In some examples, the sample preparation component includes a superstrate coupled to a substrate. In some examples, the superstrate is removably coupled to the substrate. In other examples, the superstrate is permanently coupled to the substrate. Some examples include making the substrate from a polymer-based or paper-material. The polymer-based substrate may be treated with a hydrophobic coating or fabrication may add a hydrophobic layer over the polymer-based substrate or with another substrate such that the substrate is impermeable to aqueous fluid.

In some examples, the sample preparation component may also include an assay reagent included on the superstrate. The sample preparation component further includes a superstrate coupled to a substrate.

In yet another example, the sample preparation component may include a series of scattering structures included on the superstrate. Examples of the scattering structures may include phononic structures, which are described in greater detail below.

In some examples, the substrate may be a piezoelectric material. The piezoelectric layer may be made from a composite layer, such as single crystal lithium niobate (LiNbO3). The superstrate may further include a series or plurality of electrodes or transducer. In some examples, surface acoustic waves generated by the electrodes or IDT may also be coupled into the superstrate.

In some examples, the superstrate may be made from a variety of materials, such as plastics (e.g., PET, PC, etc.).

In some examples, the superstrate may be fabricated of a material with a relatively high electromechanical coupling coefficient. In some examples, electrodes may be fabricated onto piezoelectric materials. In one example, LiNbO3 may be used as a substrate to pattern electrodes in SAW microfluidic applications. In another example, silicon may be used as a substrate material to pattern electrodes. Other examples of material applicable for fabricating a SAW-generating substrate include polycrystalline material, microcrystalline material, nanocrystalline material, amorphous material or a composite material. Other examples of material applicable for fabricating a SAW-generating substrate include ferro-electrical material, pyroelectric material, piezoelectric material or magnetostrictive material.

As described herein, the substrate is a material capable of generating surface acoustic waves and propagating acoustic waves.

In addition to the analyte or biological sample to be analyzed, the sample preparation component may also include buffer or wash fluids. In some examples, these buffer or wash fluids may facilitate the propagation of liquids across the sample preparation component and onto the detection component. In other instances, these fluids may be used to wash away any remaining liquid or biological samples once they have being positioned into the well array. Examples of such fluids include air, inert gases, hydrophobic liquids, hydrophilic liquids, oils, organic-based solvents, and high-density aqueous solutions. In certain cases, the device may be filled with a filler fluid which may be air, inert gases, hydrophobic liquids, hydrophilic liquids, oils, organic-based solvents, and high-density aqueous solutions.

In some examples, SAW induced fluidic movement can be visualized by introducing small dyes or particles into the liquid droplet.

The sample preparation surface has a surface on which the liquid may be propagated along the surface. The surface of the sample preparation surface may be any convenient surface in planar or non-planar conformation. The surface may be coated with a hydrophobic material to facilitate movement of the liquid along the surface. In some examples, the hydrophobic material may include octadecyltrichlorosilane (OTS). In other examples, the surface may be patterned to facilitate liquid movement.

In some examples, the substrate of the sample preparation surface may be elastic or flexible. The substrate on which the surface is formed upon may be elastic so that the surface is able to deform so as to facilitate the propagation of surface acoustic waves across the surface.

In certain embodiments, the surface of the substrate may include microfluidic channels to facilitate propagating fluid. In other embodiments, a microfluidic channel is included internal of the substrate to transmit fluid into the substrate.

In some examples, a cover seal may be provided over the upper surface of the substrate of the sample preparation component. In certain instances, the cover seal may prevent contamination of the liquid contents of the surface. In other instances, the cover seal may be a liquid impermeable layer. In other instances, the cover seal may be made from a flexible material such as plastics, silicon, or other type of rubber. In other instances, the cover seal may be made from a non-flexible material such as a glass or other non-flexible material. In some examples, the cover seal may be impenetrable to heat, ultraviolet light, or other electromagnetic radiation to prevent deformation of either the surface or liquid contents present on the surface.

In some examples, a suitable spacer may be positioned between the substrate and the cover seal. By "suitable spacer" as used herein, refers to an element positioned between the substrate of the sample preparation component and the cover seal. In some examples, the suitable spacer may facilitate liquid droplets to move between the surface and the cover seal. In other examples, the suitable spacer may reduce coupling between the traveling surface acoustic waves and the surface.

In the first example sample preparation component, the first substrate incorporates a material with a relatively high electromechanical coupling coefficient and having a flexible and deformable surface. For example, the first substrate may be a piezoelectric material or silicon.

In some examples, electrodes are arranged on the surface or embedded within the piezoelectric layer. The term "electrodes", as used in this context, refers to electric circuit including a electrode, a series or plurality of electrodes (e.g., more than one), a transducer. The electrode may also be patterned into the piezoelectric layer. In some examples, the electrodes may be fabricated onto the substrate using standard lithography and lift off/wet etching processes. The structure of the electrodes, spacing between electrodes, the number of electrodes (i.e., resolution) on the substrate may vary. In some examples, interdigitated (IDT) transducers or electrodes are used. IDT is defined as a combination of a series or plurality of electrodes and a piezoelectric layer on which the series or plurality of electrodes are included on. In some examples the transducer electrode structures are formed onto the piezoelectric layer. In other examples, the transducer electrode structures are embedded within the piezoelectric layer.

In some examples, surface acoustic waves are propagated when a single transducer or electrode is activated. In other examples, a plurality (e.g., pair) of electrodes fabricated on the substrate surface may generate two traveling surface acoustic waves propagating towards each other. In some examples, surface acoustic waves displacement is activated when a radio frequency (RF) range is applied to the electrodes. Upon being activated, the electrodes or transducers emit an electric potential across the surface of the substrate, where the material is subjected to mechanical stress. Examples of mechanical stress are continuous contraction and expansion of the surface of the substrate. As a result of this continuous deformation of the substrate, surface acoustic waves are propagated across the surface.

In some examples, wavelength of surface acoustic waves is dependent upon the pitch of the transducer (IDT) or series or plurality of electrodes.

In one example, the sample preparation component may include a series of phononic structure that are included on the surface of the superstrate. The phononic structures may control the propagation of the acoustic waves. For example, the phononic structures may control the direction, movement, velocity of the surface acoustic waves. The phononic structures may assume a variety of shapes and sizes as well. In some examples, the phononic structures may be pillars, cones, or holes that form a lattice within the substrate. The pattern of phononic structures on the surface of the superstrate may be predefined based on characteristics such as resolution (e.g., number of electrodes per area on the surface), electrode size, inter-digitation of the electrodes, and/or gaps or spacing between the electrodes. In some examples, characteristics of the pattern are selected based on one or more operational uses of the droplet actuator with which the SAW sample prep component is to be associated (e.g., for use with biological and/or chemical assays). In other configurations, the pattern of electrodes may be reconfigurable to enable different patterns to suit different applications. In some examples, an increase in the size or dimensions of the series or plurality of electrodes or each individual electrode may also reduce the amount of hydrophobic material applied between adjacent electrodes. Thus, the features of the electrode pattern may maximize the surface area of the SAW platform. Furthermore, increased inter-digitation of the series or plurality of electrodes/transducers facilitates the ease with which liquid is propagated across the surface via manipulation of their electrical potentials.

In the first example sample preparation component, hydrophobic material may be applied to the series or plurality of electrodes and surface of the substrate to make the superstrate impermeable to aqueous solutions. As a result of the hydrophobic material, a liquid actuated through a droplet or fluid pump is in a beaded configuration forming a contact angle with the hydrophobic layer of the surface of the substrate. In operation, SAW acoustic waves propagate across the surface coupling to the liquid, for example by penetrating or leaking into the liquid. The amplitude or frequency of the SAW acoustic wave may control the resulting frequency and motion of the moving liquid.

In certain embodiments, the surface acoustic waves propagate along the surface of the substrate and are then coupled into the superstrate. Thereafter, the surface acoustic waves continue to propagate and are guided by phononic structures that may be formed in the superstrate.

In some examples, where SAW acoustic wave are generated by two or more electrodes, it may result in controlling the direction of the liquid that is coupled to the resulting surface acoustic waves. The direction of the propagating liquid may be in a linear direction or non-linear direction. In some examples, the propagation of the liquid droplet may be in a rolling motion. In other examples, propagation of the liquid droplet may be in a sliding motion across the surface. In some examples, where there is a lack of phononic structures on the surface, propagation of the SAW and propagation of the resulting liquid droplet are in the same direction. In other examples, where there is a presence of phononic structures on the surface, propagation of SAW and propagation of resulting liquid droplets are in opposing directions or different directions.

In some examples, the hydrophobic material is a polytetrafluoroethylene material (e.g., Teflon®) or a fluorosurfactant (e.g., FluoroPel™) applied to the surface of the superstrate.

Analyte Detection Component

In some embodiments, the analyte detection component may include an array of wells in which molecules, particles, beads, or cells may be isolated for analyte or biological sample detection purpose. TSAWs (traveling surface acoustic waves) generate acoustic streaming over the surface are across the fluid channels to push fluid (either droplets or cells) towards the well array.

The shape and geometry of the wells may vary according to the type of procedure or application required. In some examples, the wells may vary between being deep chambers to shallow chambers. The wells may be any of a variety of shapes, such as, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a microbead or microparticle present in liquid droplets that have been moved over the well array. In some examples, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall. The array of wells may have sub-femtoliter volume, femtoliter volume, sub-nanolitre volume, nanolitre volume, sub-microliter volume, or microliter volume. For example the array of wells may be array of femtoliter wells, array of nanoliter wells, or array of microliter wells. In certain embodiments, the wells in an array may all have substantially the same volume. The array of wells may have a volume up to 100 µl, e.g., about 0.1 femtoliter, 1 femtoliter, 10 femtoliter, 25 femtoliter, 50 femtoliter, 100 femtoliter, 0.5 pL, 1 pL, 10 pL, 25 pL, 50 pL, 100 pL, 0.1 nL, 1 nL, 10 nL, 25 nL, 50 nL, 500 nL, 0.1 microliter, 1 microliter, 10 microliter, 25 microliter, 50 microliter, or 100 microliter.

In certain cases, the sample preparation component and the analyte detection component may be fabricated from a single planar surface using, for example, a continuous web-fed manufacturing process. In such an example, the sample preparation component and the digital analyte detection component may be positioned adjacent to each other.

In some examples, the sample preparation component may include a sample inlet. By "sample inlet" as used herein, refers to a tubular member, channel, or pipe for introducing liquid to the sample preparation component. For example, the sample inlet may introduce a biological sample onto the surface of the substrate. In other example, the sample inlet may introduce a biological sample internally within the substrate.

In other examples, the sample preparation component and the digital analyte detection component may be positioned over one another in a stacked configuration, separated by a space for droplet manipulation. In the example of the sample preparation component being positioned over the analyte detection component in a stacked configuration or vice versa (the analyte detection component being positioned over the sample preparation component), an inlet or channel may be positioned between the two components. The inlet or channel may direct a sample or analyte between the two components.

Phononic structures may be fabricated or included on the superstrate of the sample preparation component. In certain cases, the phononic structures are imprinted or embossed onto the superstrate. In such examples, the embossing or imprinting of the phononic structures is in a single step. In other examples, it may be multiple steps. Imprinting or embossing of phononic structures may be through the combination of an application of pressure, heat, or ultraviolet light in the presence of a mold, mask, or pattern. In one example, pressure elicited from a mold onto the superstrate may induce deformation of the a surface of the superstrate.

After the phononic structures are included on the superstrate, it may be cured for a sufficient period of time to allow for hardening or deformation of the phononic structures. In addition, the phononic structures may be subject to reagents that modify the physical properties of the phononic structures.

In some examples, the reagents for analyte detection may be printed during fabrication of the integrated sample preparation and analyte detection device in a dehydrated form. Rehydration of the reagents occurs through use of a sample or buffer.

In some examples, the array of wells includes individual well chambers, with each well chamber having a first end and a second end. In one example, the first end of the well may be open, while the second end of the well is closed. In other examples, both the first end of the wells and the second end of the well chambers are closed. Closure of the first end of the well chambers may be through both a permanent closure mechanism and a temporary closure mechanism. By "permanent" as used herein is meant that the closure mechanism is intended to remain a fixture of the chamber of the well. By "temporary" as used herein is meant that the closure mechanism can be removed without affecting the structure, integrity, or rigidity of the closure mechanism. In some aspects, the closure of the well chamber first end may be through a combination of a permanent and a temporary closure mechanism. In one example, the temporary closure mechanism may be a liquid, such as an oil fluid, that can fill the first end of the well chamber. In certain examples, the oil drop may fill the first well end after an analyte, biological sample, or analyte related detectable label has been previously deposited into the well. In other examples, the oil drops may be closure of the first end of the well regardless of the presence of an analyte or biological sample within the well.

The array of wells has a pattern of well chambers (e.g., the formation of wells in the array) suitable for receiving a plurality of labels, beads, labeled beads, tags, and the like. The pattern of the array of the wells may vary according to resolution and spacing between well chambers.

In some examples, the pattern of the well array can be fabricated using nanoimprint lithography. In other examples, the pattern of the well array can be fabricated through a combination of any one of molding, pressure, heat, or laser.

The size of the well array may vary. In some examples, the well array may be fabricated to have individual well chambers with a diameter of 100 nm and with a periodicity of 500 nm.

In some examples the well array may be substantially as described in the section related to digital microfluidics and detection module.

In some examples, detection of the analyte or biological sample of interest may occur through optical signal detection. For example, shining an excitation light (e.g., laser) in order to measure the signal intensity result. In other examples, the analyte desired may be detected by measuring an optical signal emanating from each well chamber and quantified by quantifying the result. For example, the number of positive counts (e.g., wells) is compared to the number of negative counts (e.g., wells) to obtain a digital count. Alternately or in addition, a signal correlated to analyte concentration may be measured (analog quantitation). A variety of signals from the wells of the device may be detected. Exemplary signals include fluorescence, chemiluminescence, colorimetric, turbidimetric, etc.

Adjacent Configuration of Sample Preparation and Analyte Detection Device

In some embodiments, the array of wells is positioned on the same superstrate as the sample preparation component. In some examples, the superstrate and the array of wells may be positioned on a first substrate. The first substrate may be divided into a first portion at which droplets to be analyzed are initially disposed and a second portion towards which the droplets are moved for analyte detection. The superstrate may be present on the first portion of the first substrate and the array of wells may be positioned on a second portion of the first substrate. As such the superstrate which forms the sample preparation component and the array of wells which form the analyte detection component may be directly adjacent. As used herein, the term "directly adjacent" refers to there being a lack of object separating or dividing the sample prep component and the array of wells. In examples, where the sample prep component and array of wells are directly adjacent to each other, the propagation of the liquid droplets across the surface of the sample prep component is seamlessly transitioned onto the surface of the array of wells. In other examples, the array of wells is positioned indirectly adjacent to the sample prep component. As used herein, the term "indirectly adjacent" refers to there being an object or element separating or dividing the sample prep component.

In some examples, to facilitate liquid movement and improve position accuracy of the droplets into the individual well chambers, the substrate surface of the sample preparation component may be patterned or coated with a hydrophilic material. In other examples, reagents such as oils and emulsions may be used to seal the well arrays.

FIG. 13A illustrates a side view of a sample preparation component positioned adjacent to an analyte detection component. As shown in FIG. 13A, the sample preparation component includes a superstrate 810. The superstrate 810 includes a series of phononic structures 830. The size, shape, and dimensions of the phononic structures may vary. As shown in FIG. 13A, the sample preparation component is positioned to be directly adjacent to the analyte detection component comprising an array of wells 860. Where these components are positioned adjacent to each other, liquid propagated across the surface of the superstrate 810 can be collected into individual well chambers on the well array 860. In this particular example, a sample inlet channel 840 is positioned between the superstrate 810 and the cover 870. The superstrate 810 and the cover 870 are separated by space/gap 850 defining a space where liquid droplets are manipulated (e.g., merged, split, agitated, etc.). However, in other examples, a sample inlet channel is not included. The size, dimensions, and variations of the sample inlet channel may vary. For example, the sample inlet channel may introduce a fluid onto the surface of the superstrate 810. In other examples, the sample inlet channel may introduce a fluid internally within the superstrate 810.

In some examples, a cover seal may be provided over the surface of the sample preparation component. In certain instances, the cover seal may prevent contamination of the liquid contents of the surface. In other instances, the cover seal is a liquid impermeable layer. In other instances, the cover seal is made from a flexible material such as plastics, silicon, or other type of rubber. In other instances, the cover seal is made from a non-flexible material such as a glass or other non-flexible material. In some examples, the cover seal may be impenetrable to heat, ultraviolet light, or other electromagnetic radiation to prevent deformation of either the surface or liquid contents present on the surface of the sample preparation component.

In some examples, a heat sink may be provided in order to dissipate the heat generated by generation of surface acoustic waves across the surface of the substrate.

Stacked Configuration of Sample Preparation and Analyte Detection Device

In some embodiments, the array of wells (detection component) is positioned over the sample preparation component separated by a space where the droplets are manipulated. In some examples, an inlet or channel may be positioned between the two components. The inlet or channel may direct a sample or analyte between the two components.

In some examples, the well array may be imprinted or embossed onto a first substrate and the phononic structure may be present on a superstrate positioned in a spaced apart manner from the first substrate. The superstrate may be supported by a second substrate.

In some examples, the step of coupling the first substrate that includes the array of wells with the superstrate may be facilitated with the use of a bonding agent, adhesive agent, tapes, glues, soldering, or other affixing agent capable of coupling the array of wells to the superstrate. In other examples, the step of coupling the array of wells onto the phononic structures of the sample prep component may be achieved through use of mechanical fasteners, fixers, bolts, and other mechanical components such as latches. In other examples, the step of coupling the array of wells onto the phononic structures of the sample prep component may occur through setting and positioning the array of wells over the phononic structures of the sample prep component. In some examples, the phononic structures of the substrate may be in parallel orientation to the well array component.

The spacing between the phononic structures of the superstrate and the well array may vary according to the type of application to be performed, the size of the liquid droplet being actuated onto the surface of the substrate, the size, shape and arrangement of phononic structures, the size of the sample channel/inlet, and the amplitude of the surface acoustic waves propagating across the surface.

FIG. 13B illustrates a side view of a stacked configuration of a superstrate and well array component. As shown in FIG. 13B, the superstrate 810 includes a series of phononic structures 830. The phononic structures 830 are arranged in an array of repeating structural elements. The size, shape, and dimensions of the phononic structures may vary. In this example, an array of wells 860 is also present. In this example, the array of wells 860 is positioned directly over the superstrate. As illustrated in FIG. 13B, the opening of the wells may be directly opposite the phononic structures. In this particular example, a sample inlet channel 840 is positioned between the well array and the superstrate. However, in other examples, a sample inlet channel is not included. The size, dimensions, and variations of the sample inlet channel may vary. For example, the sample inlet channel may introduce a fluid onto the surface of the superstrate 810. In other examples, the sample inlet channel may introduce a fluid internally within the superstrate 810. The substrate 820 that includes the array of wells 860 is positioned in a spaced apart manner from the superstrate 810 and is separated from the superstrate 810 by a gap/space 850.

The array of wells as shown in FIGS. 13A-B can vary in size and/or shape. For example, the well array can be substantially shallow or deep. The resolution of the well array is affected by the spacing between each well chamber. For example, minimal spacing between the well chambers allows for a greater number of wells to collect a greater number of analytes or biological samples. In some examples, well array may be formed via ablating the substrate. The pattern of the well array may be formed by using a special pattern or special mask, and subjecting the mask to Laser Ablation.

Fabricating Surface Acoustic Wave Sample Preparation and Detection Device

FIGS. 14A-14B illustrate exemplary methods for separately fabricating the SAW devices disclosed in the foregoing sections. FIG. 14A illustrates that the sample preparation component and well array component are positioned adjacent to each other by fabricating the phononic structures and the array of wells on a single base substrate. A superstrate (e.g., see FIG. 13A, superstrate 810) is placed on an assembly line 900. Propagation of the superstrate along the assembly line 900 is facilitated by a conveyer belt-like mechanism utilizing a series of rollers. A roll 914 of the superstrate is unspooled and is subjected to an embossing unit 910, which subjects the material to intense heat, pressure, or ultraviolet light in order to form phononic structures on the superstrate or embedded within the superstrate using a mold. The array of wells is created using laser ablation 924. Thereafter, the superstrate passes through a plurality of rollers to a surface treatment component 920, which modifies properties of the superstrate. Thereafter, the superstrate passes through an inkjet printer 930 that deposits assay reagents on the superstrate. In some examples, the resulting structures may be subject to a curing step. In other examples, the resulting structures may be subjected to surface treatment to modify their physical properties, for example, incorporating functionalized reagents required for assay protocols. A cover (e.g., FIG. 13A, cover 870) is then laminated 940 onto the superstrate. The cover may be provided as a roll 905 which is unspooled and moved using rollers. Prior to placing the cover on the superstrate, a suitable spacer is placed between the superstrate and the cover to enable liquid droplets to move between the two surfaces. The assembled structure may be diced 950 to generate individual devices.

FIG. 14B illustrates an exemplary method for fabricating the device depicted in FIG. 13B. A roll 914 of superstrate (e.g., see FIG. 13B, superstrate 810) is subjected to a fabrication process using an embossing unit 910, which subjects the superstrate to intense heat, pressure, or ultraviolet light in order to form repeating structural elements of phononic structures in the presence of a mold. Thereafter, the superstrate passes through a surface treatment component 920 to modify properties of the superstrate surface. Thereafter, the superstrate passes through an inkjet printer 930, to deposit assay reagents in situ. To form the detection module comprising an array of wells, a roll 906 of a first substrate (e.g., see FIG. 13B, substrate 820) is subjected to laser ablation 924. At the lamination unit 940, both the superstrate and the first substrate containing well array are combined together and subsequently bonded in a spaced apart configuration. As a result, the superstrate and the substrate are aligned vertically within a stack configuration. Thereafter, the stacked substrates are subject to a dicing component 950, for example, to generate individual devices.

The devices and systems and method described herein that propagate droplet actuation may also include a variety of other forces that affect droplet actuation. For example, movement of the droplets across the surfaces may include electric field-mediated forces, electrostatic actuation (such as electrical actuation), electrowetting, dielectrophoresis, electric field gradients or electrode-mediated forces. In embodiments where a combination of surface acoustic waves and digital microarray electrodes are used for droplet manipulation the SAW devices described herein may include a series or plurality of electrodes.

The integrated devices disclosed herein may be used to prepare a variety of samples, such as biological sample, for detection of an analyte of interest. In certain cases, the device may be used for carrying out digital immunoassay and detect presence or absence of particles/beads that are correlated to the presence or absence of an analyte.

Kits and Cartridges

Also provided herein is a kit for use in performing the above-described methods with or without the disclosed device. The kit may include instructions for analyzing the analyte with the disclosed device. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, "instructions" may include the address of an internet site that provides the instructions.

The kit may include a cartridge that includes a microfluidics module with a built-in analyte detection, as described above. In some embodiments, the microfluidics and analyte detection may be separate components for reversible integration together or may be fully or irreversibly integrated in a cartridge. The cartridge may be disposable. The cartridge may include one or more reagents useful for practicing the methods disclosed above. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent(s), a standard(s) (e.g., calibrators and controls), and/or any other material useful in sample processing, washing, or conducting any other step of the assay. The cartridge may include one or more of the specific binding members described above.

Alternatively or additionally, the kit may comprise a calibrator or control, e.g., purified, and optionally lyophilized analyte of interest or in liquid, gel or other forms on the cartridge or separately, and/or at least one container (e.g., tube, microtiter plates or strips) for use with the device and methods described above, and/or a buffer, such as an assay buffer or a wash buffer, either one of which can be provided as a concentrated solution. In some embodiments, the kit comprises all components, i.e., reagents, standards, buffers, diluents, etc., which are necessary to perform the assay. The instructions also can include instructions for generating a standard curve.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay. Exemplary concentration ranges for the reference standards include but are not limited to, for example: about 10 fg/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 pg/mL, about 20 pg/mL, about 50 pg/mL, about 75 pg/mL, about 100 pg/mL, about 150 pg/mL, about 200 pg/mL, about 250 pg/mL, about 500 pg/mL, about 750 pg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1000 µg/mL, about 2000 µg/mL, about 3000 µg/mL, about 4000 µg/mL, about 5000 µg/mL, about 6000 µg/mL, about 7000 µg/mL, about 8000 µg/mL, about 9000 µg/mL, or about 10000 µg/mL.

Any specific binding members, which are provided in the kit may incorporate a label, such as a fluorophore, enzyme, dendrimer, bead, nanoparticle, nanobead, microparticle, microbead, polymer, protein, biotin/avidin label, or the like, or the kit can include reagents for labeling the specific binding members or reagents for detecting the specific binding members and/or for labeling the analytes or reagents for detecting the analyte. If desired, the kit can contain one or more different tags or labels. The kit may also include components to elicit cleavage, such as a cleavage mediated reagent. For example, a cleavage mediate reagent may include a reducing agent, such as dithiothreitol (DTT) or tris(2-carboxyethyl)phosphine) TCEP. The specific binding members, calibrators, and/or controls can be provided in separate containers or pre-dispensed into an appropriate assay format or cartridge.

The kit may include one or more specific binding members, for example, to detect one or more target analytes in the sample in a multiplexing assay. The number of different types of specific binding members in the kit may range widely depending on the intended use of the kit. The number of specific binding members in the kit may range from 1 to about 10, or higher. For example, the kit may include 1 to 10 specific binding members, 1 to 9 specific binding members, 1 to 8 specific binding members, 1 to 7 specific binding members, 1 to 6 specific binding members, 1 to 5 specific binding members, 1 to 4 specific binding members, 1 to 3 specific binding members, 1 to 2 specific binding members, 2 to 10 specific binding members, 2 to 9 specific binding members, 2 to 8 specific binding members, 2 to 7 specific binding members, 2 to 6 specific binding members, 2 to 5 specific binding members, 2 to 4 specific binding members, 3 to 10 specific binding members, 3 to 9 specific binding members, 3 to 8 specific binding members, 3 to 7 specific binding members, 3 to 6 specific binding members, 3 to 5 specific binding members, 3 to 4 specific binding members, 4 to 10 specific binding members, 4 to 9 specific binding members, 4 to 8 specific binding members, 4 to 7 specific binding members, 4 to 6 specific binding members, 5 to 10 specific binding members, 5 to 9 specific binding members, 5 to 8 specific binding members, 5 to 7 specific binding members, 5 to 6 specific binding members, 6 to 10 specific binding members, 6 to 9 specific binding members, 6 to 8 specific binding members, 6 to 7 specific binding members, 7 to 10 specific binding members, 7 to 9 specific binding members, 7 to 8 specific binding members, 8 to 10 specific binding members, 8 to 9 specific binding members, or 9 to 10 specific binding members. Each of the one or more specific binding members may bind to a different target analyte and each specific binding member may be labeled with a different detectable label. For example, the kit may include a first specific binding member binds to a first target analyte, a second specific binding member binds to a second target analyte, a third specific binding member binds to a third target analyte, etc. and the first specific binding member is labeled with a first detectable label, the second specific binding member is labeled with a second detectable label, the third specific binding member is labeled with a third detectable label, etc. In addition to the one or more specific binding member, the kits may further comprise one or more additional assay components, such as suitable buffer media, and the like. Finally, the kits may comprise instructions for using the specific binding members in methods of analyte detection according to the subject invention, where these instructions for use may be present on the kit packaging and/or on a package insert.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container or cartridge for a urine, saliva, plasma, cerebrospinal fluid, or serum sample, or appropriate container for storing, transporting or processing tissue so as to create a tissue aspirate). Where appropriate, the kit optionally also can contain reaction vessels, mixing vessels, and other components that facilitate the preparation of reagents or the test sample. The kit can also include one or more sample collection/acquisition instruments for assisting with obtaining a test sample, such as various blood collection/transfer devices such as microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or canula, for obtaining, storing or aspirating tissue samples; or the like. The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laproscopic biopsies.

If the tag or detectable label is or includes at least one acridinium compound, the kit can comprise at least one acridinium-9-carboxamide, at least one acridinium-9-carboxylate aryl ester, or any combination thereof. If the tag or detectable label is or includes at least one acridinium compound, the kit also can comprise a source of hydrogen peroxide, such as a buffer, solution, and/or at least one basic solution. If desired, the kit can contain a solid phase, such as a magnetic particle, bead, membrane, scaffolding molecule, film, filter paper, disc, or chip.

If desired, the kit can further comprise one or more components, alone or in further combination with instructions, for assaying the test sample for another analyte, which can be a biomarker, such as a biomarker of a disease state or disorder, such as infectious disease, cardiac disease, metabolic disease, thyroid disease, etc.

The present invention has multiple aspects, illustrated by the following non-limiting examples.

EXAMPLES

Example 1

Fabrication of Low-Cost DMF Chip

Figure 18:
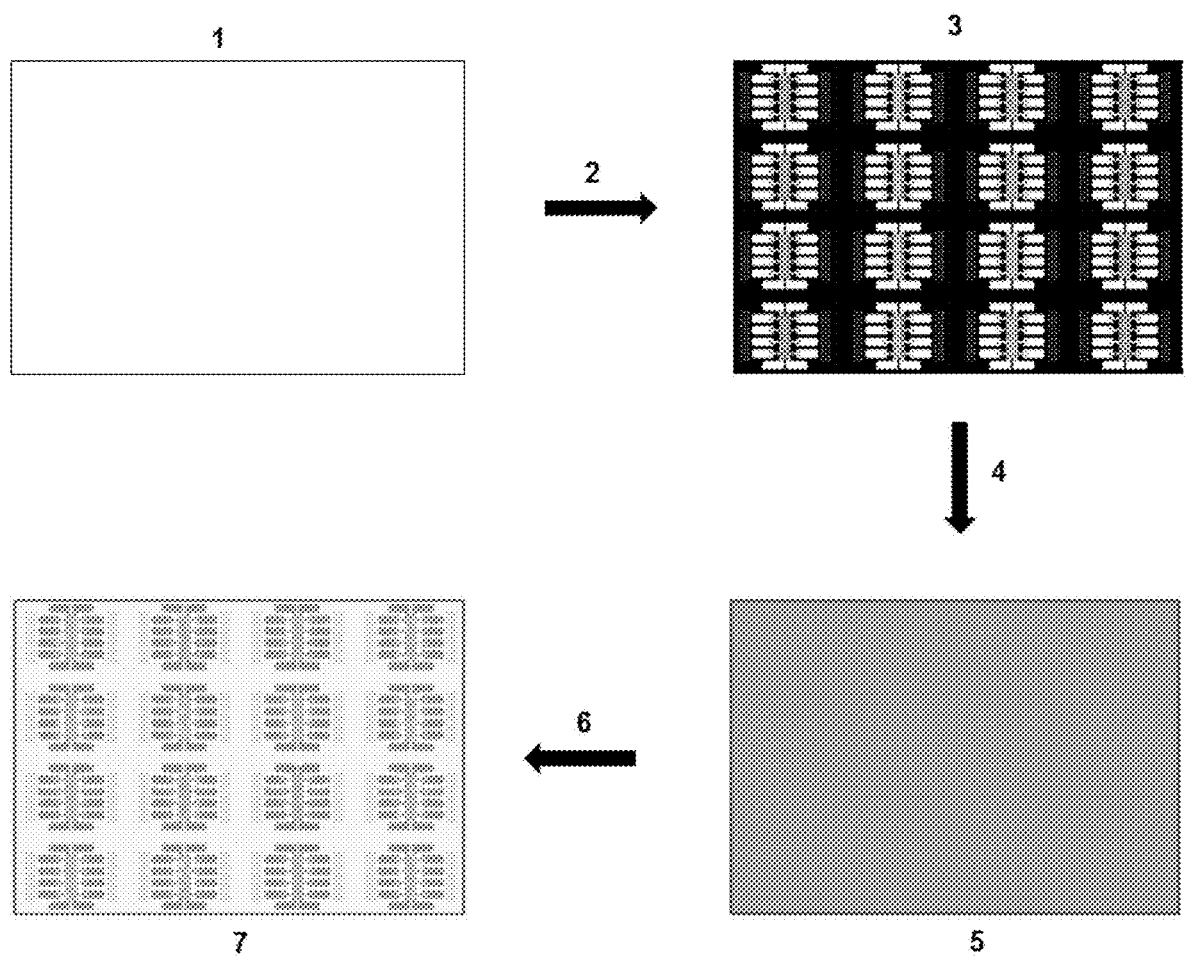
FIG. 18 depicts a schematic of a fabrication process of a low-cost DMF chip.

Low-cost flexible DMF chips were fabricated using roll-to-roll (R2R) flexographic printing combined with a wet lift-off process for electrode patterning. A schematic of the fabrication process is depicted in FIG. 18. A roll of Melinex ST506 polyethylene terephthalate (PET) 5.0 mil substrate (1) was used as the starting material for DMF electrode printing. A layer of yellow ink (Sun Chemical) was flexo-printed (2) on the PET substrate using a 1.14 mm thick printing plate (Flint MCO3) at a rate of 10 m/minute using an ink transfer volume of 3.8 ml/m2 on an Anilox roller assembly. A negative image of the DMF electrode pattern results from the flexo printing step (3). Prior to metal deposition, the ink was dried two times in a hot air oven (2×100° C.). An EVA R2R Metal Evaporator was used to deposit a layer of silver metal onto the printed PET substrate to form a uniform coating of silver at a thickness of 80 nm (4). The metalized ink-film substrate (5) was subjected to a wet lift-off process using a combination of acetone plus ultrasound in a sonication bath at a speed of 1 m/minute (6). This chemical/physical treatment allows the silver-ink layer to dissolve, while keeping the silver-only layer intact. Removal of the ink-silver layer resulted in a DMF printed electrode pattern consisting of 80 actuation electrodes (2.25×2.25 mm) with either 50 or 140 □m electrode gap spacing (7). As a QC check, a total of 80-90 random chips from a single roll were visually inspected for electrode gap spacing and connector lead width variation. Typical yields of chips, determined to have acceptable gap specifications, were close to 100%. A single fabricated flexible chip is depicted in FIG. 19. The fabricated flexible chip measures 3"×2" and includes electrodes, reservoirs, contact pads and leads.

A dielectric coating was applied to the electrodes and reservoirs by using either rotary screen printing or Gravure printing. For rotary screen printing, Henkel EDAC PF-455B was used as a dielectric coating by printing with a Gallus NF (400 L) screen at a printing speed of 2 m/minute and a UV curing rate of 50%. Typical dielectric thickness was 10-15 □m. For Gravure printing, cylinders were designed to print a high-viscosity dielectric ink, such as IPD-350 (Inkron), at a speed of 2 m/minute using an ink volume of 50 ml/m2. Typical dielectric thickness for Gravure printing was 7-8 □m. A final hydrophobic layer was printed using either Millidyne Avalon 87 or Cytonix Fluoropel PFC 804 UC coating with Gravure cylinders (140-180 L) and a printing speed of 8 m/minute, followed by four successive oven drying steps (4×140° C.). Typical hydrophobic thickness was 40-100 nm.

Alternatively, for small batches of individual chips, the dielectric and hydrophobic coatings may be applied using chemical vapor deposition (CVD) and spin coating, respectively.

Example 2

Functional Testing of Low-Cost DMF Chip

A 3"×2" PET-based DMF bottom chip manufactured as outlined in Example 1 above was tested for actuation capability. FIG. 20 depicts a 3"×2" PET-based DMF chip (1) over which a 0.7 mm thick glass substrate (3) is positioned. The glass substrate (3) includes a transparent indium tin oxide (ITO) electrode on a lower surface of the glass substrate and a Teflon coating over the ITO electrode. The DMF chip includes 80 silver actuation electrodes with a straight edge electrode design and a 50 µm gap between electrodes, along with 8 buffer reservoirs (see Example 1 above).

The bottom electrodes were coated with a layer of dielectric Parylene-C (6-7 µm thick) and a final coating of Teflon (50 nm thick) by CVD and spin-coating, respectively. Approximately 50 µl of PBS buffer with 0.1% surfactant (2) was pipetted into four adjacent reservoirs on the bottom DMF chip. Droplet sizes ranged from 700-1,500 nl (one or two droplets) and were checked for both vertical and horizontal lateral movement (4), in addition to circular sweep patterns necessary for mixing. Droplet actuation was achieved using a voltage of 90 Vrms. Approximately 90% of the actuation electrodes on the chip were tested and found to be fully functional.

Example 3

TSH Immunoassay on Low-Cost DMF Chip

Figure 21A:
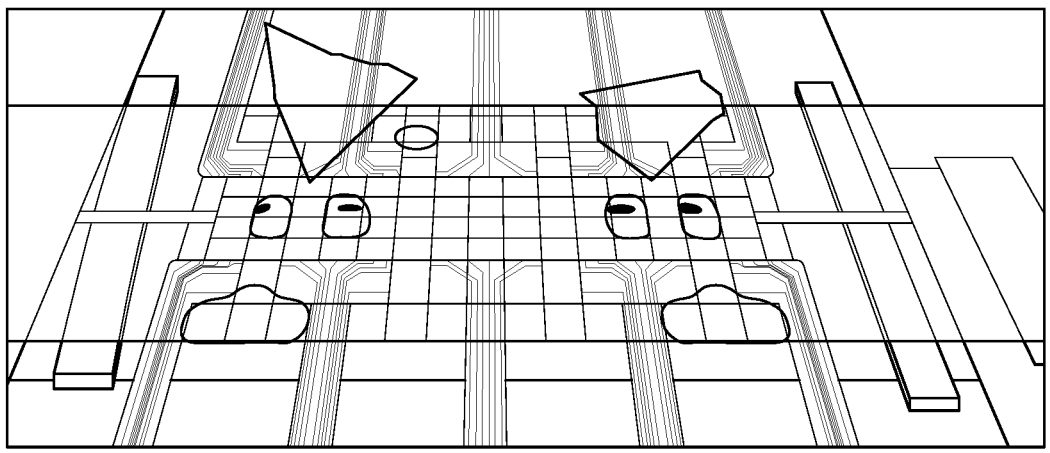
FIGS. 21A-21E depicts performance of an immunoassay in a DMF chip, according to embodiments of the present disclosure.
Figure 21B:
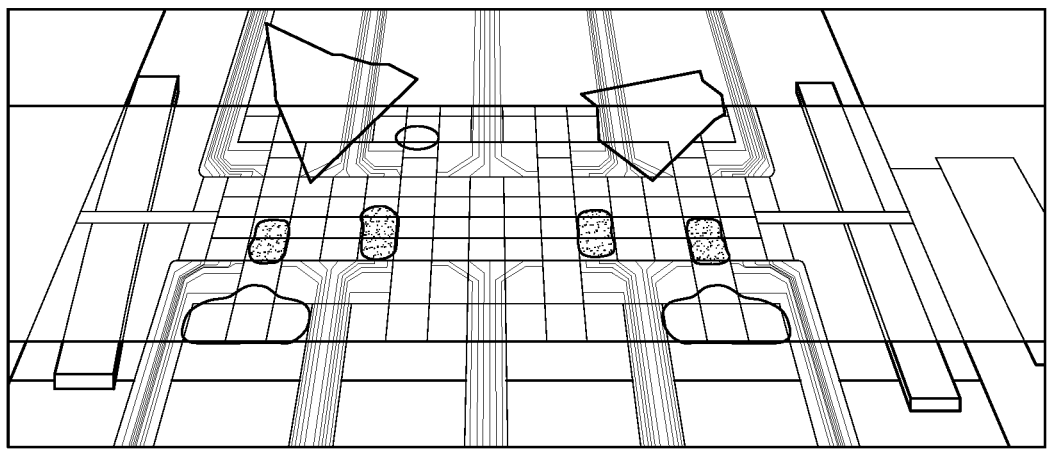
Figure 21C:
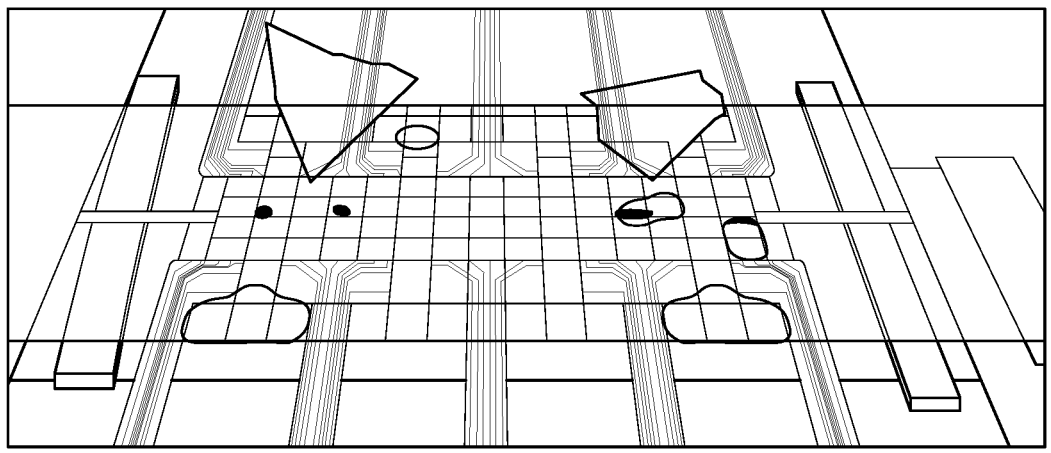
Figure 21D:
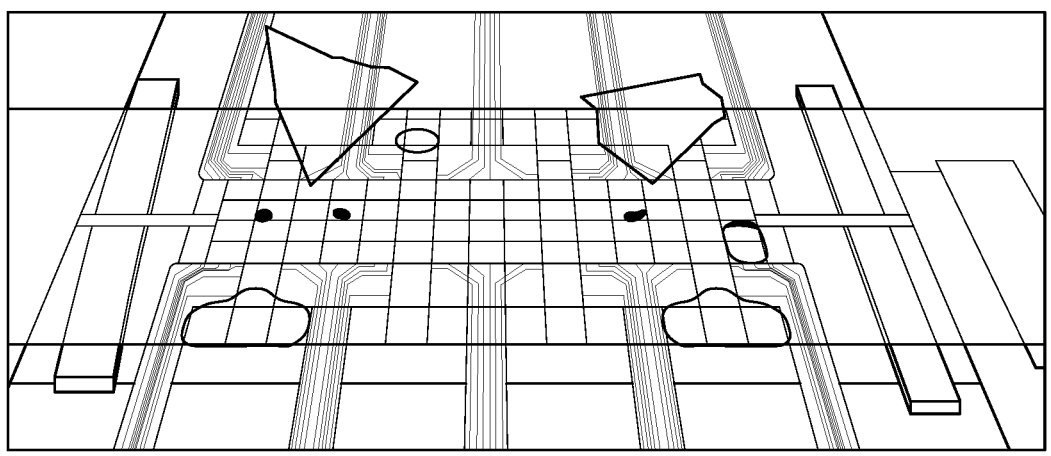
Figure 21E:
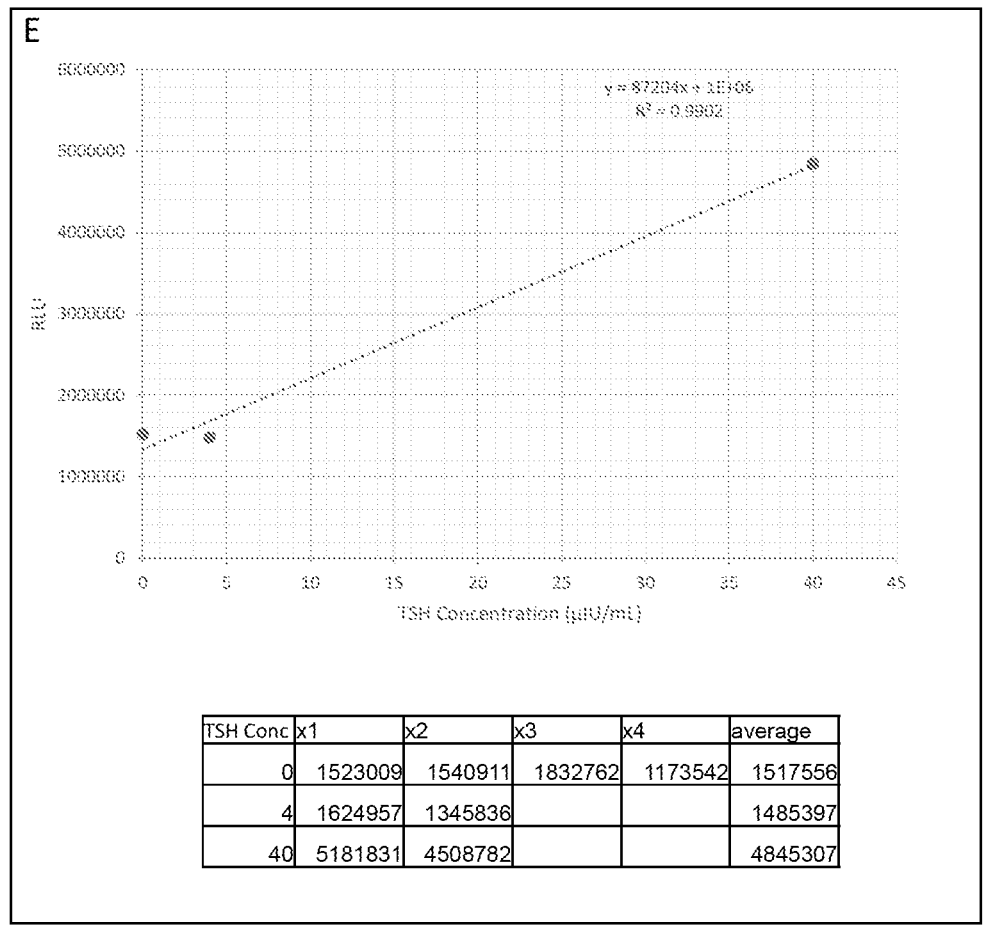

The 3'×2" PET-based DMF chip overlayed with the glass substrate as described in Example 2 above, was tested for its ability to carry out a thyroid stimulating hormone (TSH) immunoassay, using chemiluminescence detection. Mock samples included TSH calibrator material spiked into TBS buffer containing a blocking agent and a surfactant. Three samples were tested—0, 4, 40 µIU/ml. 2 µl of anti-beta TSH capture antibody, coated on 5 µm magnetic microparticles (3×108 particles/ml), was dispensed from the microparticle reservoir into the middle of the DMF electrode array. The magnetic microparticles were separated from the buffer by engaging a neodymium magnet bar under the DMF chip (FIG. 21A) (3 in.×½ in.×¼ in. thick, relative permeability µr=1.05, remnant field strength Br=1.32 T). 5 µl of sample was moved to the microparticle slug, followed by mixing the microparticle suspension (FIG. 21B) over a four-electrode square configuration for 5 minutes. The microparticles were separated from the sample by the magnet, and the supernatant was moved to a waste reservoir (FIGS. 21C and 21D). 2 µl of 1 µg/ml anti-TSH detection antibody conjugated to horseradish peroxidase (HRP) was moved to the microparticle slug and mixed for 2 minutes. The microparticles were separated by the magnet, and the supernatant was moved to the waste reservoir. The microparticles containing the immunoassay sandwich complex were washed a total of four times with 4×2 µl of PBS wash buffer containing 0.1% surfactant. Wash buffer from each wash step was moved to waste after the step was completed. Chemiluminescent substrate consisted of 1 µl of SuperSignal H2O2 and 1 µl luminol (ThermoFisher Scientific), which was moved to the microparticle slug, followed by mixing for 6 minutes. Chemiluminescent signal was measured at 427 nm emission (347 nm excitation) using an integrated Hamamatsu H10682-110 PMT with a 5 V DC source. A dose-response curve was plotted against relative luminescence (see FIG. 21E).

Example 4

Fabrication and Design of DMF Too Electrode Chips and Well Array

Figure 22A:
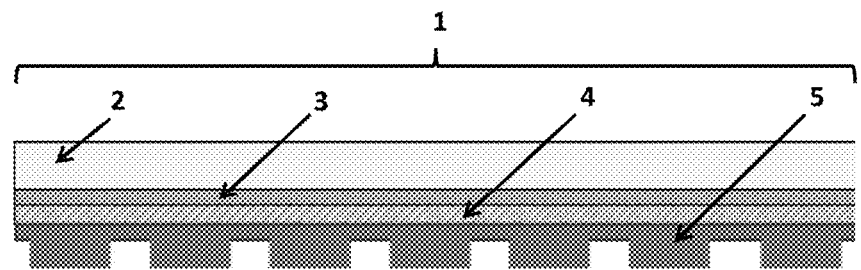
FIGS. 22A and 22B are schematic diagrams showing a design and fabrication method of DMF top electrode chips and well array, according to embodiments of the present disclosure.

Top Electrode Design:

The low-cost flexible DMF top electrode chips containing the well array were fabricated using roll-to-roll (R2R) gravure printing and UV imprinting. With reference to FIG. 22, the basic design (1) incorporated two sets of well arrays printed on a flexible substrate of polyethylene terephthalate (PET) that was used as the top electrode for the DMF chip. The design consisted of 100 nm thick layer of indium-tin oxide (ITO)(3) printed on Melinex ST504 PET substrate (2) (Solutia, OC50 ST504). A coating of PEDOT:PSS primer (4) was used to improve adhesion of the UV embossing resist (5), which contained the final well arrays.

Figure 22B:
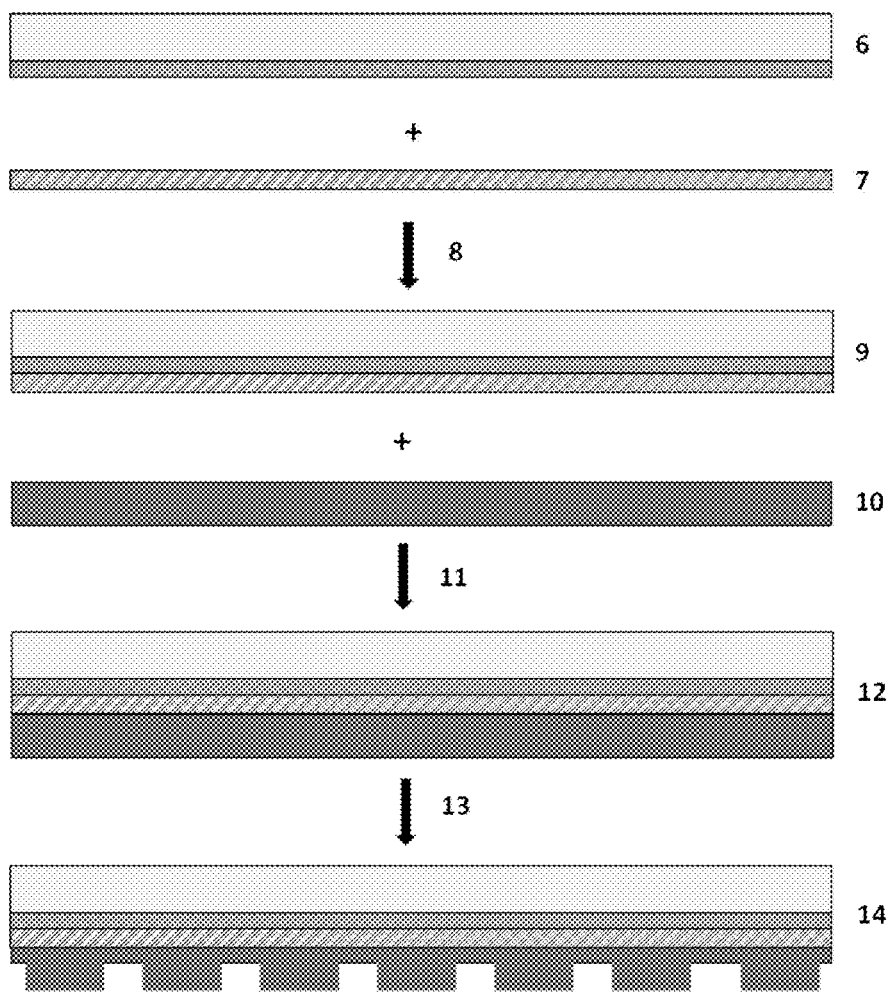

Roll-to-Roll Fabrication of Top Electrode:

FIG. 22B shows a schematic of a fabrication process for the DMF top electrode.

Gravure printing (8) was used to coat a 20 nm thick primer layer of PEDOT:PSS (7) (Clevios VP AI4083), diluted with isopropanol to reduce the viscosity, on 5-mil Melinex ST504 PET substrate (6). The roll size was 250 m×200 mm×125 µm; printing speed was 10 m/minute. The resulting primer-coated ITO electrode (9) was transferred to a second R2R printing line where a layer of UV resist (10) was applied with gravure coating (11) to form the precursor material for UV embossing (13). Contact with the nanoarray mold, followed by UV curing, produced the final R2R top electrode film (14), ready to be cut.

Figure 23:
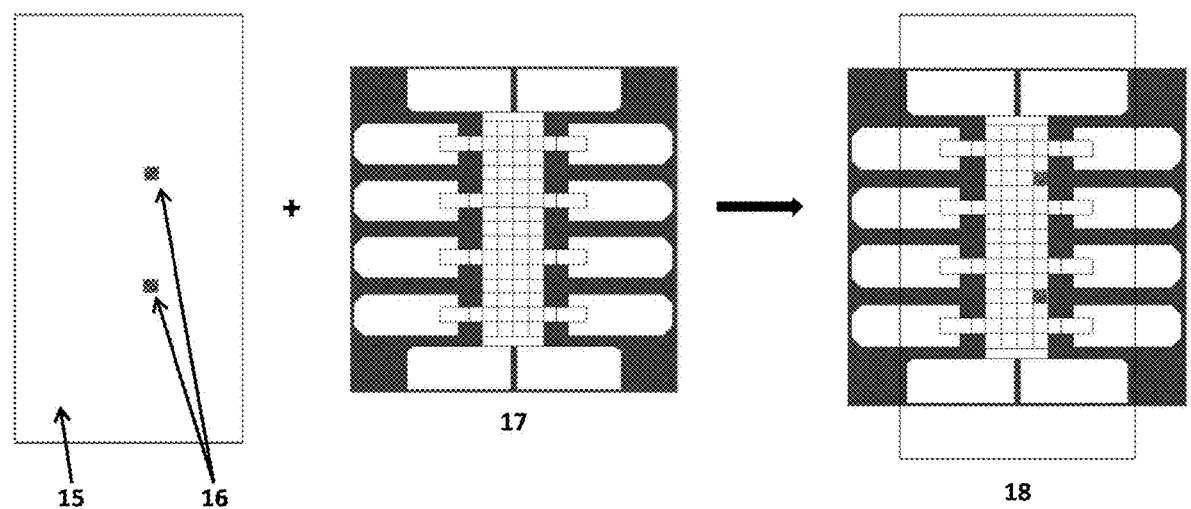
FIG. 23 shows a schematic diagram of a well design, according to embodiments of the present disclosure.

Well Design:

A well design is shown in FIG. 23. The top chip containing the ITO common electrode was designed to be cut into 3"×1.4" strips (15), each containing two nano-dimensioned well arrays (16) positioned to align with two exterior actuation electrodes on the bottom chip (17). Placement of the top electrode over the bottom chip gave the final DMF chip assembly (18). Each array contained approximately 60,000 wells (245×245).

Figure 24A:
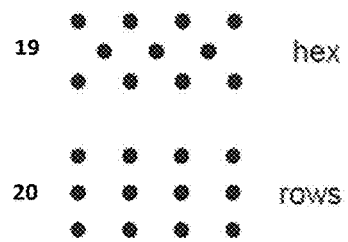
FIGS. 24A and 24B are schematic diagram showing well spacing formats, according to embodiments of the present disclosure.
Figure 24B:
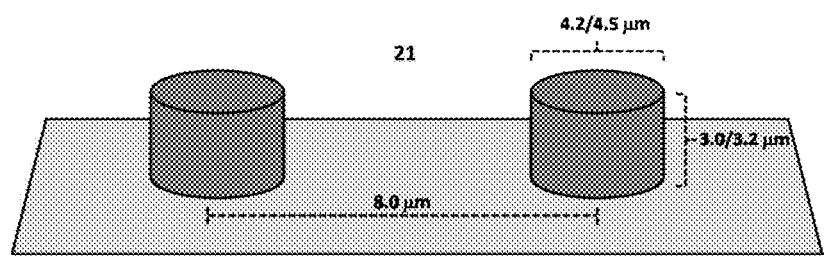
Figure 25:
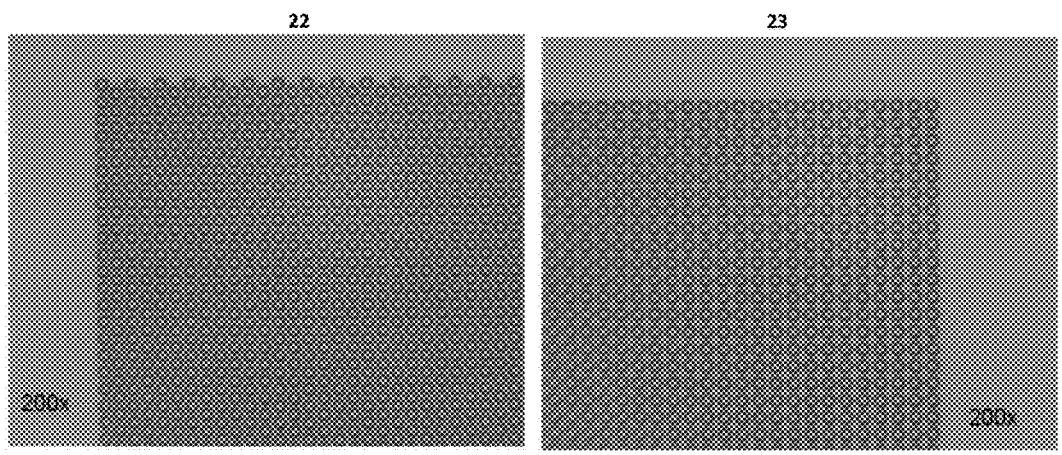
FIG. 25 are a collection of magnified optical images of the array of wells, according to embodiments of the present disclosure.

With reference to FIGS. 24A and 24B, two different well spacing formats were used in the initial design—hexagonal (19) and straight rows (20). In addition, two shim designs were used to print two different well sizes (21) 4.2 µm wide×3.0 µm deep with a pitch of 8.0 µm; 4.5 µm×3.2 µm with a pitch of 8.0 µm. Varying the well size and geometric spacing was done in order to optimize for subsequent microparticle loading of 2.7 µm diameter beads. Post-fab QC was conducted on various R2R runs to check for proper well spacing, size and integrity. If deformed wells were observed or the well spacing and/or size was incorrect, a new shim was manufactured and the array was re-printed. FIG. 25 shows optical images at 200× magnification for hexagonal (22) and straight row (23) arrays.

Example 5

Assembly of DMF Too Electrode Chips Containing a Well Array

Figure 26:
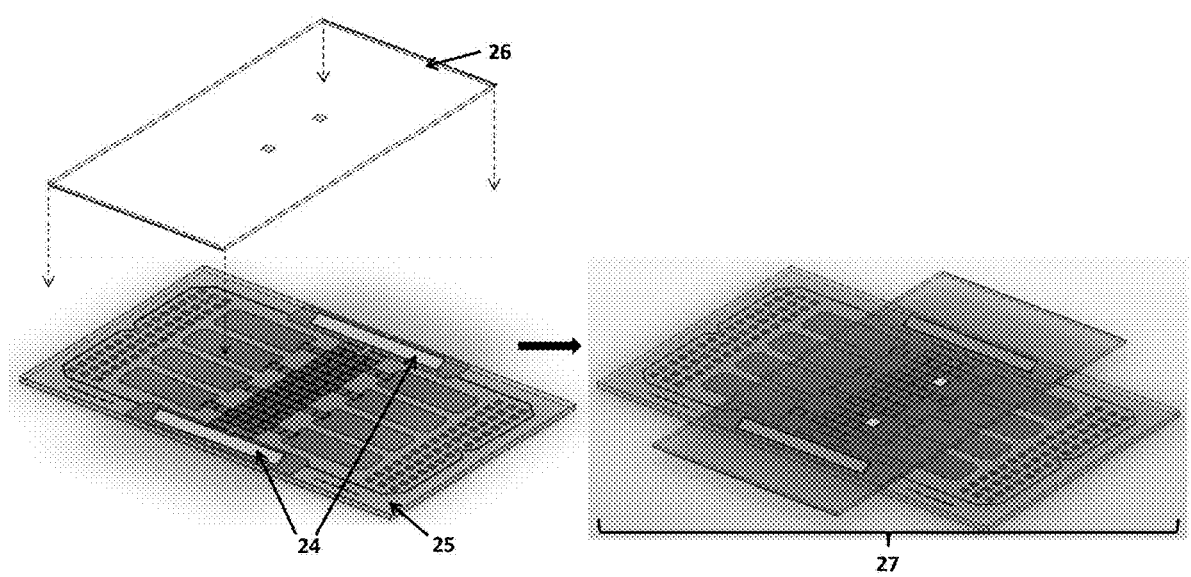
FIG. 26 is a schematic diagram showing assembly of an integrated DMF-well device from a DMF top electrode chip and a well array, according to embodiments of the present disclosure.

DMF Plastic Chip Assembly:

FIG. 26 schematically describes assembly of the integrated DMF-well device from DMF top electrode chip and a nano-dimensioned well array, as described in Example 4 above. The DMF chip is assembled by placing 2×2 pieces of 90 µm double-sided tape (24) (3M) on opposite sides of the bottom DMF chip (25). The top electrode, containing the embedded arrays (26), is centered on top of the bottom chip so that the position of the two arrays aligns with the two underlying actuation electrodes. The final assembled chip (27) has a gap height of 180 µm (2×90 µm tape).

Example 6

TSH Immunoassay on Low-Cost DMF-Well Integrated Chip

Figure 27A:
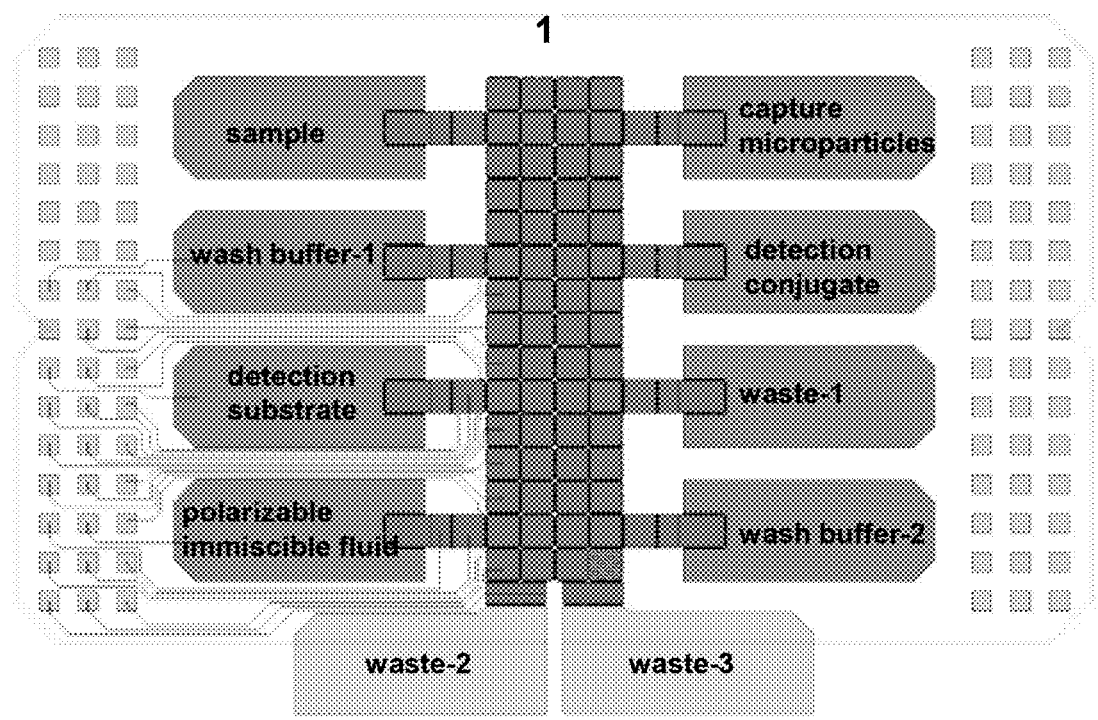
FIGS. 27A-27G are a collection of schematic diagrams showing an immunoassay performed on a integrated DMF-well device, according to embodiments of the present disclosure.
Figure 27B:
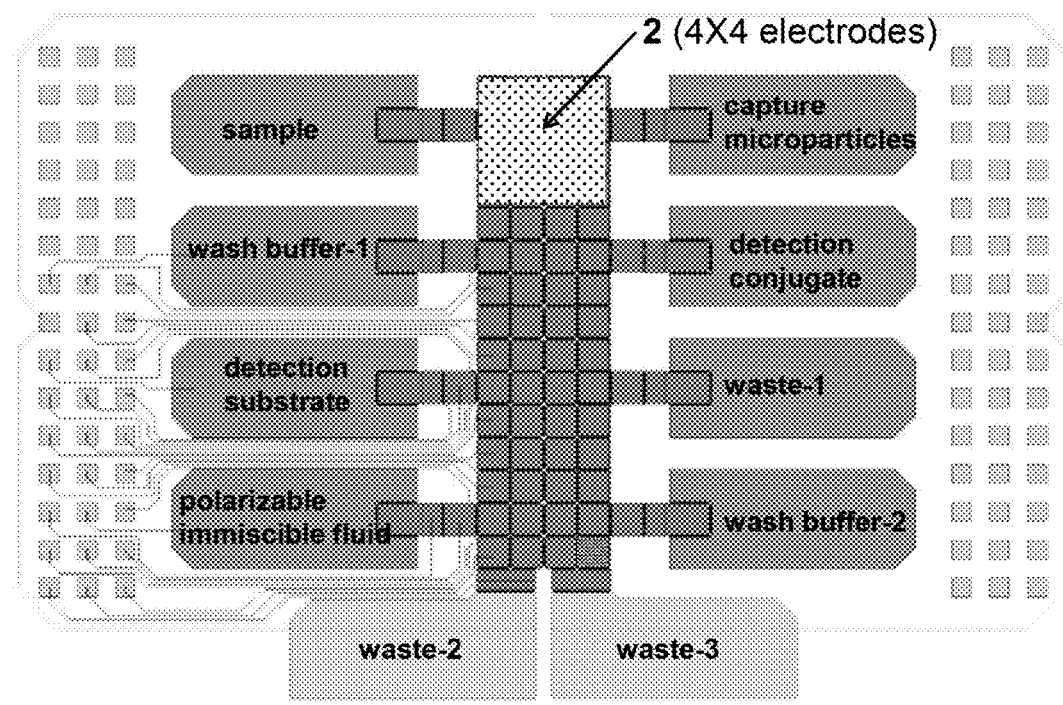

An immunoassay for TSH is described using a combination of DMF, micro-dimensioned well array and digital detection of a fluorescent substrate (FIGS. 27A-27G). A DMF chip (top and bottom electrodes) is pre-loaded with immunoassay (IA) reagents, as shown in (1) (FIG. 27A). The assay is carried out on the DMF chip using air as the filler fluid. The sample may be a biological sample such as whole blood, serum, plasma, urine, sputum, interstitial fluid, or similar matrix. The capture microparticles consists of a suspension of solid-phase magnetic microparticles coated with anti-beta TSH antibodies at a density of $2\times10^7$–$2\times10^8$ particles/ml. Approximately 1-2 µl of sample is moved onto the DMF chip and combined with 1-2 µl of microparticles, followed by mixing within Zone 1 (2) of the DMF chip (FIG. 27B). Zone 1 consists of 16 DMF electrodes reserved for combining, mixing and washing of the sample to form a capture complex of TSH on the magnetic microparticles. Incubation time can range from 1-10 minutes, followed by 1-3 washes of 1-2 µl wash buffer (PBS, 0.1% surfactant) from wash buffer 1 reservoir. Supernatant is removed from the IA complex by engaging a magnet below the DMF chip and moving the supernatant to waste reservoir 1.

Figure 27C:
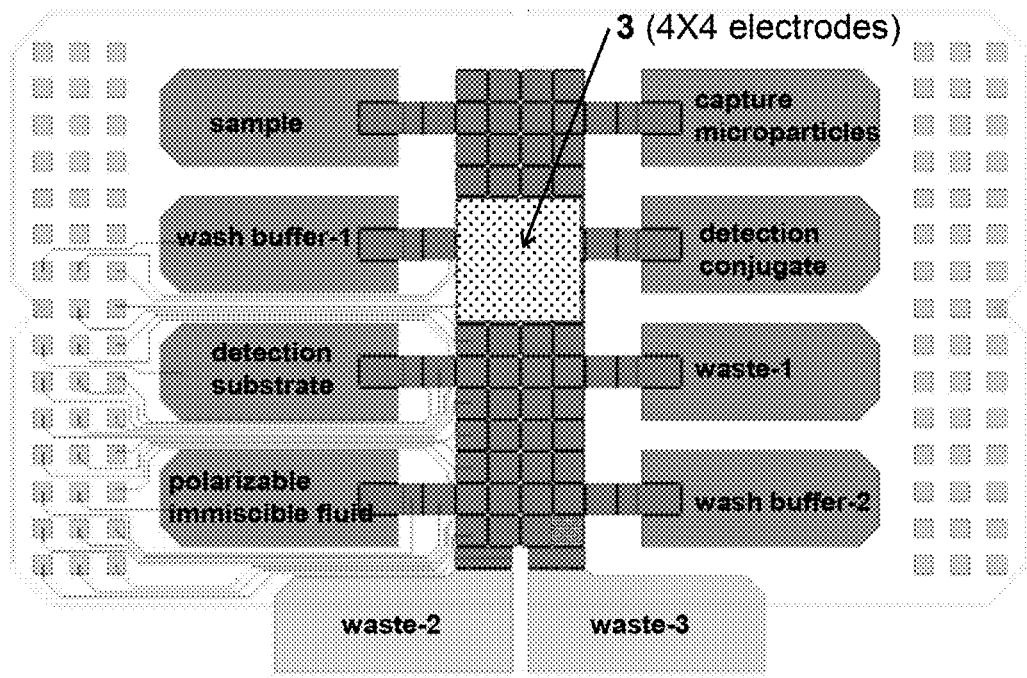
Figure 27D:
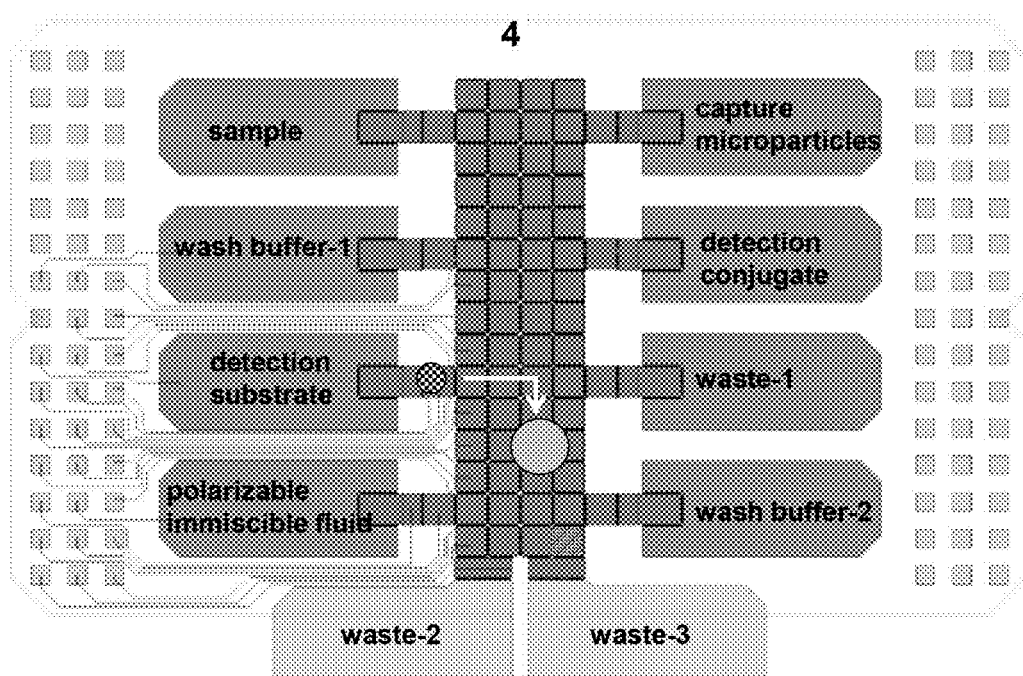

The microparticle slug containing the captured TSH antigen on solid phase is resuspended in 1-2 µl of anti-beta TSH detection conjugate antibody labeled with biotin (streptavidin-β-galactosidase complex, at a concentration of 40 pM in PBS). The mixture is allowed to incubate, with mixing over 4×4 electrodes, in Zone 2 on the DMF electrode array (3) for 1-10 minutes (FIG. 27C). The magnet is engaged to capture the magnetic microparticles, and the supernatant is removed to reservoir waste 1. The slug is washed 1-3 times with 1-2 µl wash buffer (PBS, 0.1% surfactant) from wash buffer 2 reservoir. Supernatant is removed from the IA complex by engaging a magnet below the DMF chip and moving the supernatant to waste reservoir 2. The microparticle slug, containing the immunoassay sandwich complex, is resuspended by moving 1-2 µl of 100 µM detection substrate (4) (resorufin-β-D-galactopyranoside, RGP) (FIG. 27D). The mixture is incubated for 1-3 minutes to allow for the enzymatic turnover of RGP—a fluorescent product produced from the enzymatic turnover of RGP by β-galactosidase.

Figure 27E:
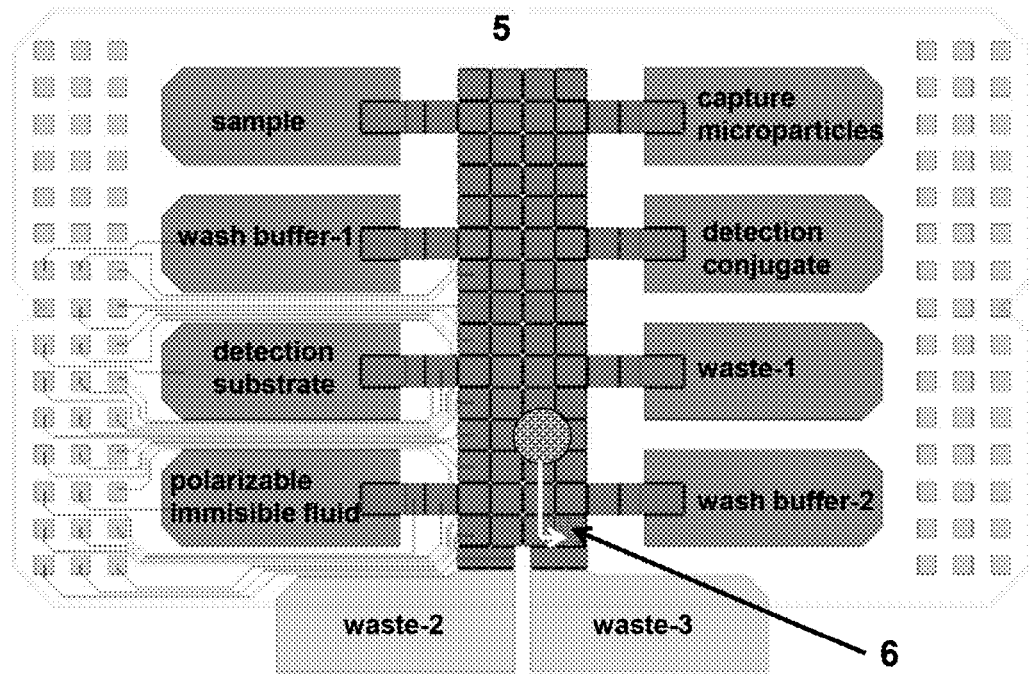

The mixture is moved (5), as shown in FIG. 27E, to a spot on the DMF chip that contains an array of femtoliter wells (6), either on the bottom or top substrate. The size of the femtoliter well size is slightly larger than the size of the microparticle being used in the assay. The number of wells may range from 1,000-2,000,000. The microparticles are deposited in the wells by using either gravity (passive loading) or a magnet (active loading). Excess supernatant is moved to waste-3 reservoir.

Figure 27F:
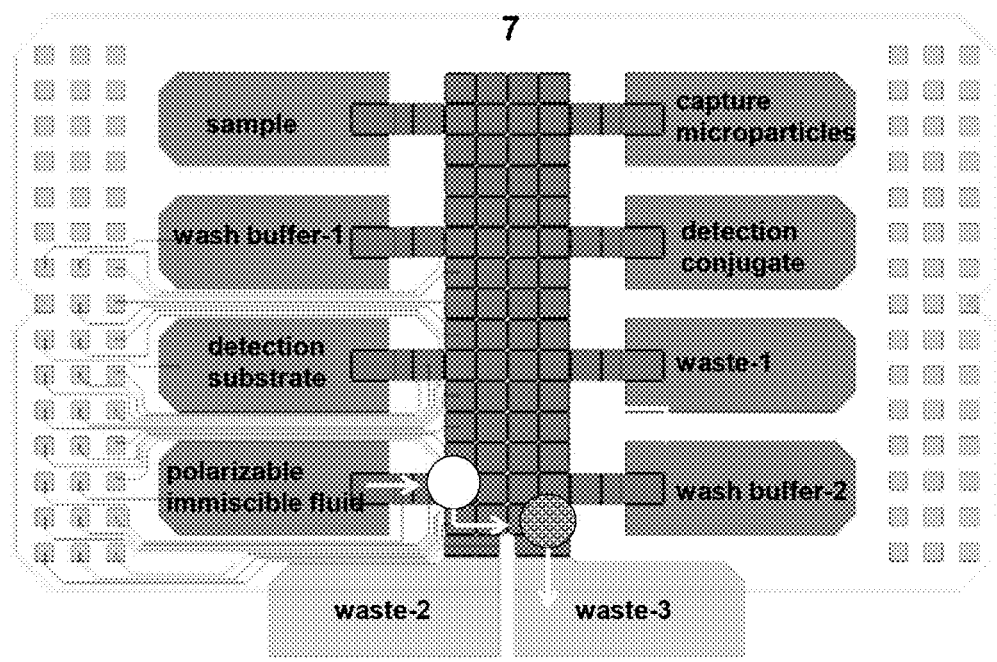
Figure 27G:
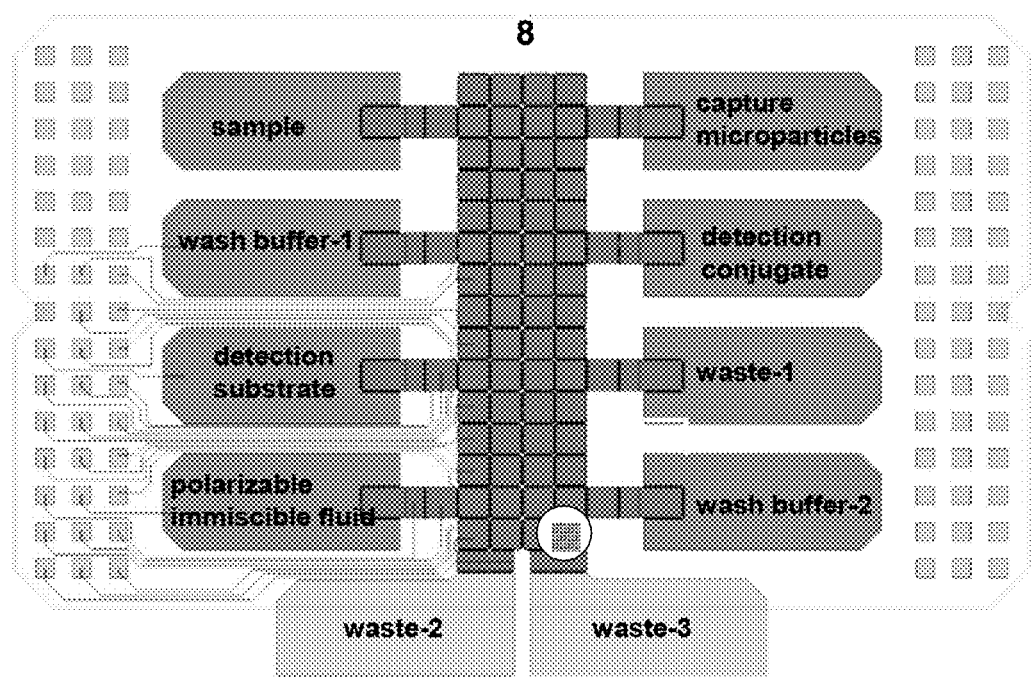

The femtoliter wells are sealed by moving 1-5 µl of a polarizable immiscible fluid (i.e. organic solvent, oil, etc.) to the array position (7, 8), as shown in FIGS. 27F and 27G, using electrowetting on dielectric (EWOD), dielectrophoresis (DEP) force(s), or surface acoustic waves (SAW) thereby sealing the wells. Some examples of suitable polarizable immiscible fluids include silicone oil, fluorosilicone oil, mineral oil, 1-hexanol, THF, m-dichlorobenzene, chloroform, and the like (S. Fan, et al., Lab On Chip, 9, 1236, 2009; D. Chattejee, et al., Lab On Chip, 6, 199, 2006). The filler fluid for the entire assay is air.

The number of total particles in the wells is determined by white light illumination with a wide field microscope/CCD camera, followed by imaging at 574 nm/615 nm excitation/emission (exposure time=3-10 seconds) for determining the number of beads containing a detection label. The final TSH concentration is determined from a standard curve run with TSH calibrators. Digital quantitation is determined by using the Poisson equation and the ratio of positive to negative beads.

Example 7

Nanodimensiond Well Top Loading with Polarizable Fluid

Figure 28:
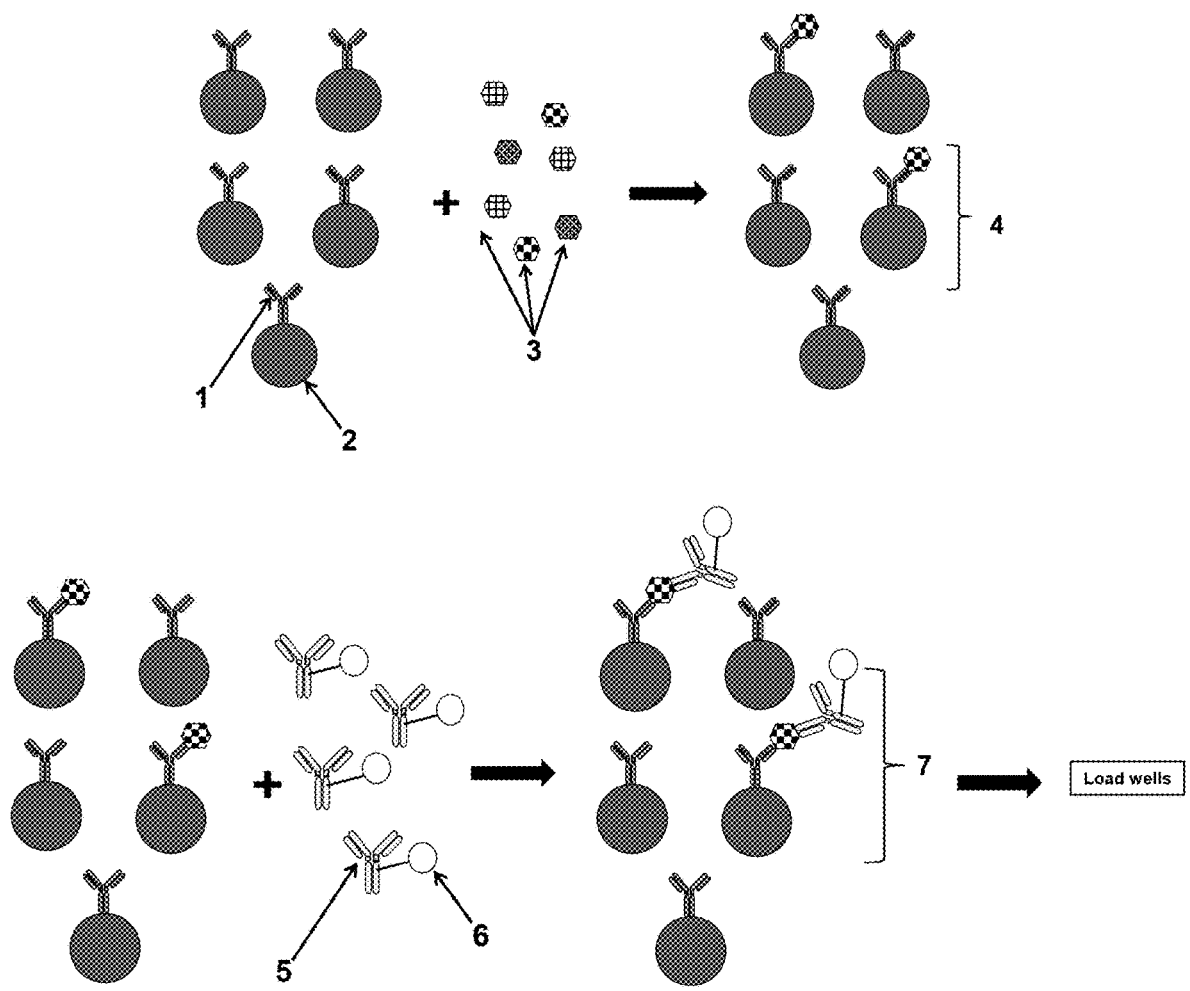
FIG. 28 is a schematic diagram of an enzyme-linked immunosorbent assay (ELISA)-based sandwich immunoassay, coupled with digital fluorescence detection in a well array, according to embodiments of the present disclosure.

General Immunoassay Format:

The 3'×2" PET-based DMF chip can be used to run an ELISA-based sandwich immunoassay, coupled with digital fluorescence detection in the well array. With reference to FIG. 28, a sample (3), containing a specific antigen to be analyzed, is mixed with magnetic microparticles (2) coated with a capture antibody (1) and mixed to allow for immunocapture of the desired antigen. After washing, the captured antigen (4) is mixed with a second detection antibody (5) labeled with a detection moiety (6). The bead mixture, containing the sandwich immunoassay complex (7), is washed again to remove unbound detection antibody. The microparticles are loaded in the top substrate of the well array by moving the aqueous droplet to the array and applying a magnet to pull the beads into the wells. The wells are sealed by moving a droplet of polarizable immiscible fluid over the wells using DMF forces. A CCD camera images the array to determine the number of positive and negative microparticles. The sample is quantitated using Poisson statistics. All immunoassay processing steps are carried out on a DMF chip using air as the filler fluid.

TSH Immunoassay—DMF:

One-two µl of anti-TSH capture antibody, coated on 2.7 µm magnetic microparticles (3×108 particles/ml), is dispensed from the microparticle reservoir on the DMF chip into the middle of the DMF electrode array. The magnetic microparticles are separated from the buffer by engaging a magnet, located under the DMF chip, and moving the supernatant to the waste reservoir. One µl of an aqueous sample is pulled from a DMF sample reservoir and moved to the microparticle slug, followed by a mixing step where the droplet is moved over several electrodes for 1-5 minutes. The microparticles are separated from the sample by applying the bottom magnet, followed by removal of the supernatant to a waste reservoir. One-two µl of anti-TSH detection antibody (0.5 µg/ml) conjugated to β-galactosidase (β-gal) is moved to the microparticle slug and mixed for 2-5 minutes. The microparticles are separated using the bottom magnet and the supernatant is moved to the waste reservoir. The microparticles containing the immunoassay sandwich complex are washed a total of four times with 4×2 µl of PBS wash buffer containing 0.1% surfactant. Wash buffer from each wash step is moved to waste after the step is completed.

One µl of 100 µM resorufin-β-D-galactopyranoside (RGP) is taken from the RGP reservoir and moved to the microparticle slug, followed by mixing for 15-30 seconds. The beads are now ready for deposition into the well array.

TSH Immunoassay—Digital Array Detection:

As shown in FIG. 29, the basic components for DMF-directed top loading of the microparticles into the array includes the bottom PET-based electrode chip with 80-nm thick silver electrodes (8) (electrod gap<100 µm, 2.25 mm×2.25 mm), 5-10 µm thick dielectric/hydrophobic layer (9), the top PET-based ITO electrode (10) chip containing the array of wells (14) (configured to hold no more than one microparticle) and an aqueous droplet (11) containing 2.7 µm magnetic microparticles (12). The filler fluid is air (13). The gap height between the top and bottom electrodes is approximately 180 µm (from 2 pieces of 90 µm double-sided tape).

Transport and sealing is accomplished by using a combination of DMF forces (EWOD, DEP, and/or electromediated force) to move aqueous and immiscible fluids, such as silicone oil. It has been previously shown that different driving voltages are required to move both aqueous and oil droplets on the same DMF chip (S-K Fan, et al., Lab on Chip, 9, 1236, 2009).

After addition of the fluorescent substrate RGP to the aqueous droplet containing the immunoassay complex (FIG. 30A), the droplet is moved to an electrode positioned below a well array containing approx. 60,000 wells (245×245 array; 4.2 µm diameter; 3.0 µm depth; 8.0 µm pitch) using a voltage of 20-50 Vrms (1 KHz). A top magnet (15) is engaged to promote efficient loading of the microparticles into the wells (FIG. 30B); total deposition time is 30-60 seconds. The aqueous droplet is moved away as the top magnet is dis-engaged, leaving behind a thin layer of deposited and surface-bound beads (FIG. 30C). A droplet of silicone oil is moved from a reservoir using a voltage of 200-300 V (DC) and moved to the electrode positioned under the array (FIG. 30D), thereby washing away any surface-bound microparticles, while sealing microparticles contained in the wells. The fluorescence generated from enzymatic turnover of RGP to resorufin is monitored by a CCD camera at 574/615 nm (excitation/emission). The ratio of "on" microparticles to "off" microparticles is determined. The TSH concentration in the sample is determined by interpolation from a TSH calibration curve.

Finally, although the various aspects and features of the invention have been described with respect to various embodiments and specific examples herein, all of which may be made or carried out conventionally, it will be understood that the invention is entitled to protection within the full scope of the appended claims.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

1. A digital microfluidic and analyte detection device, comprising:
a first substrate and a second substrate, wherein the second substrate is separated from the first substrate by a gap, the first substrate comprising a plurality of electrodes to generate electrical actuation forces on a liquid droplet; and
an array of wells dimensioned to hold a portion of the liquid droplet, wherein at least a portion of the array of wells is positioned between one or more of the plurality of electrodes and the gap.

2. The device according to clause 1, wherein the plurality of electrodes is positioned on a surface of the first substrate.

3. The device according to clause 1 or clause 2, further comprising a first layer disposed on the surface of the first substrate and covering the plurality of electrodes.

4. The device of any one of the previous clauses, wherein the first substrate comprises a first portion at which the liquid droplet is introduced and a second portion toward which a liquid droplet is moved.

5. The device of clause 4, wherein the plurality of electrodes and the first layer extend from the first portion to the second portion of the first substrate.

6. The device of clause 5, wherein the array of wells is positioned in the second portion of the first substrate.

7. The device according to clause 4, wherein the second substrate comprises a first portion and a second portion, wherein the first portion is in facing arrangement with the first portion of the first substrate and the second portion is in facing arrangement with the array of wells.

8. The device of clause 7, wherein the second portion of the second substrate is substantially transparent to facilitate optical interrogation of the array of wells.

9. The device according to clause 3, further comprising a second layer disposed on a surface of the first layer.

10. The device according to clause 9, wherein a second layer extends over the first and second portions of the first substrate.

11. The device according to any one of clauses 9-10, wherein the first layer is a dielectric layer and the second layer is a hydrophobic layer.

12. The device according to any one of clauses 9-11, wherein the array of wells is positioned in the second layer.

13. The device according to any one of clauses 3, wherein the array of wells is positioned in the first layer.

14. The device according to any one of the previous clauses, wherein the array of wells has a hydrophilic surface.

15. The device according to any one of the previous clauses, wherein the array of wells comprise a sidewall that is oriented to facilitate receiving and retaining of beads or particles present in droplets moved over the well array.

16. The device according to clause 16, wherein the array of wells comprise a first sidewall opposite to a second side wall, wherein the first sidewall is oriented at an obtuse angle with reference to a bottom of the wells, and wherein the second sidewall is oriented at an acute angle with reference to the bottom of the wells, wherein movement of droplets is in a direction parallel to the bottom of the wells and from the first sidewall to the second sidewall.

17. The device according to clause 15, wherein the array of wells have a frustoconical shape with a narrower part of the frustoconical shape providing an opening of the array of wells.

18. The device according to clause 15, wherein the array of wells comprise a first sidewall opposite to a second side wall, wherein a top portion of the first sidewall is oriented at an obtuse angle with reference to a bottom of the wells and a bottom portion of the sidewall is oriented perpendicular to the bottom of the wells, and wherein the second sidewall is oriented perpendicular with reference to the bottom of the wells, wherein the movement of droplets is in a direction parallel to the bottom of the wells and from the first sidewall to the second sidewall, wherein the top portion of the first side wall is at an opening of the wells.

19. A digital microfluidic and analyte detection device, comprising:
a first substrate and a second substrate defining the device, wherein the second substrate is separated from the first substrate by a gap, wherein the device comprises a first portion and a second portion; and
the first portion comprising a plurality of electrodes to actuate combining of a first liquid droplet containing an analyte of interest from a biological sample and a second liquid droplet containing at least one bead; and
the second portion comprising an array of wells dimensioned to hold a portion of the liquid droplet.

20. The device according to clause 19, wherein the plurality of electrodes are only positioned in the first portion of the device.

21. The device according to clause 19 or clause 20, wherein the plurality of electrodes is positioned on a surface of the first substrate.

22. The device according to any one of clauses 19-21, further comprising a first layer disposed on the surface of the first substrate and covering the plurality of electrodes.

23. The device of any new of clauses 19-22, wherein the first substrate comprises a first portion at which the liquid droplet is introduced and a second portion toward which a liquid droplet is moved.

24. The device of clause 23, wherein the plurality of electrodes and the first layer extend from the first portion to the second portion of the first substrate.

25. The device of clause 24, wherein the array of wells is positioned in the second portion of the first substrate.

26. The device according to clause 23, wherein the second substrate comprises a first portion and a second portion, wherein the first portion is in facing arrangement with the first portion of the first substrate and the second portion is in facing arrangement with the array of wells, 27. The device of clause 26, wherein the second portion of the second substrate is substantially transparent to facilitate optical interrogation of the array of wells.

28. The device according to any one of clauses 19-27, wherein the plurality of electrodes are configured to move a droplet placed in the gap towards the second portion of the device, the device comprising a capillary portion fluidically connecting the first portion to the second portion, wherein the capillary comprises a hydrophilic material to facilitate movement of the droplet from the first portion to the second portion via the capillary portion in absence of an electric force.

29. The device according to any one of clauses 22, wherein a second layer is disposed on an upper surface of the first layer.

30. The device according to clause 29, wherein a second layer extends over the first substrate.

31. The device according to any one of clauses 29-30, wherein the first layer is a dielectric layer and the second layer is a hydrophobic layer.

32. The device according to any one of clauses 29-31, wherein the plurality of wells is positioned in the second layer.

33. The device according to clauses 22, wherein the array of wells is positioned in the first layer.

34. The device according to any one of clauses 19-33, wherein the array of wells has a hydrophilic surface.

35. The device according to any one of clauses 19-34, wherein the wells comprise a sidewall that is oriented to facilitate receiving and retaining of nanobeads or nanoparticles present in droplets moved over the well array.

36. The device according to clause 35, wherein the wells comprise a first sidewall opposite to a second side wall, wherein the first sidewall is oriented at an obtuse angle with reference to a bottom of the wells, and wherein the second sidewall is oriented at an acute angle with reference to the bottom of the wells, wherein the movement of droplets is in a direction parallel to the bottom of the wells and from the first sidewall to the second sidewall.

37. The device according to clause 36, wherein the wells have a frustoconical shape with the narrower part of the frustoconical shape providing the opening of the wells.

38. The device according to clause 35, wherein the wells comprise a first sidewall opposite to a second side wall, wherein a top portion of the first sidewall is oriented at an obtuse angle with reference to a bottom of the wells and a bottom portion of the sidewall is oriented perpendicular to the bottom of the wells, and wherein the second sidewall is oriented perpendicular to the bottom of the wells, wherein the movement of droplets is in a direction parallel to the bottom of the wells and from the first sidewall to the second sidewall, wherein the top portion of the first side wall is at an opening of the wells.

39. A surface acoustic wave microfluidic and analyte detection device, comprising:
   a first substrate and a second substrate, wherein the second substrate is separated from the first substrate by a gap, wherein the device comprisers a first portion and a second portion,
   the first portion comprising a superstrate coupled to a surface acoustic wave generating component; and
   the second portion comprising a plurality of wells positioned on the first substrate or the second substrate.

40. The device according to clause 39, wherein the superstrate includes phononic structures on an upper surface of the superstrate.

41. The device according to clause 39 or clause 40, wherein the superstrate overlays a piezoelectric crystal layer.

42. The device according to any one of clauses 39-40, wherein the second substrate is substantially transparent.

43. A surface acoustic wave microfluidic and analyte detection device, comprising:
   a first substrate and a second substrate, wherein the second substrate is separated from the first substrate by a gap,
   the first substrate comprising a plurality of wells, and
   the second substrate comprising phononic structure, wherein the plurality of wells and the phononic structures are located across to each other.

44. The device according to clause 43, wherein the second substrate is a superstrate.

45. The device according to clause 43, wherein a superstrate is disposed on the second substrate and the phononic structure are located on the superstrate.

46. The device according to any one of clauses 43-45, wherein the first substrate, second substrate and superstrate are substantially transparent.

47. A method of detecting an analyte of interest in a liquid droplet, the method comprising:
   (a) providing a first liquid droplet containing an analyte of interest;
   (b) providing a second liquid droplet containing at least one solid support which contains a specific binding member that binds to the analyte of interest;
   (c) using energy to exert a force to manipulate the first liquid droplet with the second liquid droplet to create a mixture;
   (d) moving all or at least a portion of the mixture to an array of wells, wherein one or more wells of the array is of sufficient size to accommodate the at least one solid support;
   (e) adding a detectable label to the mixture either before or after moving a portion of the mixture to array of wells; and
   (f) detecting the analyte of interest in the wells.

48. The method of clause 47, wherein the at least one solid support comprises at least one binding member that specifically binds to the analyte of interest.

49. The method of any one of clauses 47 or 48, further comprising adding a detectable label to the mixture before the moving at least a portion of the mixture to the array of wells.

50. The method of any one of clauses 47 or 48, further comprising adding a detectable label to the mixture after the moving at least a portion of the mixture to the array of wells.

51. The method of any one of clauses 47 to 50, wherein the detectable label comprises at least one binding member that specifically binds to the analyte of interest.

52. The method of any one of clauses 47 to 51, wherein the detectable label comprises a chromagen, a fluorescent compound, an enzyme, a chemiluminescent compound or a radioactive compound.

53. The method of any one of clauses 47 to 52, wherein the binding member is a receptor or an antibody.

54. The method of any one of clauses 47 to 53, wherein the energy is an electric actuation force or acoustic force.

55. The method of clause 54, wherein the electric actuation force is droplet actuation, electrophoresis, electrowetting, dielectrophoresis, electrostatic actuation, electric field mediated, electrode mediated, capillary force, chromatography, centrifugation, or aspiration.

56. The method clause 54, wherein the acoustic force is surface acoustic wave.

57. The method of any one of clauses 47 to 56, wherein the first liquid droplet is a polarizable liquid, the second liquid droplet is a polarizable liquid, the mixture is a polarizable liquid or both the first liquid droplet and second liquid droplet are each polarizable polarizable liquids.

58. The method of any one of clauses 47 to 55, further comprising manipulating the at least a portion of the mixture over the array of wells using an electric actuation force.

59. The method of any one of clauses 47 to 58, further comprising manipulating the at least a portion of the mixture over the array of wells using a capillary element configured to facilitate movement of the mixture to the array of wells.

60. The method of any one of clauses 47 to 59, wherein the solid supports are magnetic solid supports.

61. The method of clause 60, wherein an electric actuation force and the magnetic field are applied from opposite directions relative to the at least a portion of the mixture.

62. The method of any one of clauses 47 to 61, further comprising mixing the mixture by moving the mixture back and forth, moving the mixture in a circular pattern, splitting the mixture into two or more submixtures and merging the submixtures.

63. The method of any one of clauses 47 to 62, wherein the mixture is an aqueous liquid.

64. The method of any one of clauses 47 to 62, wherein the mixture is an immiscible liquid.

65. The method of any one of clauses 47 to 64, wherein the liquid droplet is a hydrophobic liquid droplet.

66. The method of any one of clauses 47 to 65, wherein the array of wells has a hydrophilic surface.

67. The method of any one of clauses 47 to 65, wherein the array of wells has a hydrophobic surface.

68. The method of any one of clauses 47 to 67, wherein the method is performed in an device comprising a first and second substrate and at least one substrate comprises a hydrophilic surface.

69. The method of any one of clauses 47 to 67, wherein the method is performed in an device comprising a first and second substrate and at least one substrate comprises a hydrophobic surface.

70. The method of any one of clauses 47 to 69, further comprising generating an electric actuation force with a plurality of electrodes to move the mixture to the array of wells to load the wells.

71. The method of any one of clauses 47 to 70, wherein one or more wells of the array are loaded with at least one solid support.

72. The method of clause 71, wherein the loading comprises applying a magnetic field to facilitate movement of at least one solid support into the one or more wells of the array.

73. The method of clause 72, further comprising removing any solid supports that are not loaded into a well of the array after the loading.

74. The method of clause 73, wherein the removing comprises generating an electric actuation force with the plurality of electrodes to move a polarizable fluid droplet to the array of wells to move the at least a portion of the mixture to a distance from the array of wells.

75. The method of clause 74, wherein the removing comprises generating an electric actuation force with the plurality of electrodes to move an aqueous washing droplet across the array of wells.

76. The method of clause 75, wherein generating an electric actuation force comprises generating an alternating current.

77. The method of clause 75, wherein the alternating current has a root mean squared (rms) voltage of 10 V or more.

78. The method of any one of clauses 75 or 76, wherein the alternating current has a frequency in a radio frequency range.

79. The method of any one of the clauses 47 to 78, wherein the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

80. A method of detecting an analyte of interest in a liquid droplet, the method comprising:

(a) providing a first liquid droplet containing an analyte of interest;

(b) providing a second liquid droplet containing a detectable label which contains a specific binding member that binds to the analyte of interest;

(c) using energy to exert a force to manipulate the first liquid droplet and the second liquid droplet to create a mixture;

(d) moving all or at least a portion of the mixture to an array of wells; and (e) detecting the analyte of interest in the wells.

81. The method of clause 80, wherein the detectable label comprises a chromagen, a fluorescent compound, an enzyme, a chemiluminescent compound or a radioactive compound.

82. The method of any of clauses 80 to 81, wherein the energy is an electric actuation force or acoustic force.

83. The method of clause 82, wherein the electric actuation force is droplet actuation, electrophoresis, electrowetting, dielectrophoresis, electrostatic actuation, electric field mediated, electrode mediated, capillary force, chromatography, centrifugation, or aspiration.

84. The method clause 83, wherein the acoustic force is surface acoustic wave.

85. The method of clauses 80 to 83, wherein the first liquid droplet is a polarizable immiscible liquid, the second liquid droplet is a polarizable liquid, the mixture is a polarizable liquid or both the first liquid droplet and second liquid droplet are each polarizable liquids.

86. The method of any one of clauses 80 to 83 and 85, further comprising manipulating the mixture over the array of wells using an electric actuation force.

87. The method of any one of clauses 80 to 86, further comprising manipulating the mixture over the array of wells using a capillary element configured to facilitate movement of the mixture to the array of wells.

88. The method of any one of clauses 80 to 87, further comprising mixing the mixture by moving the mixture back and forth, moving the mixture in a circular pattern, splitting the mixture into two or more submixtures and merging the submixtures.

89. The method of any one of clauses 80 to 88, wherein the mixture is an aqueous liquid.

90. The method of any one of clauses 80 to 88, wherein the mixture is an immiscible liquid.

91. The method of any one of clauses 80 to 90, wherein the liquid droplet is a hydrophobic liquid droplet.

92. The method of any one of clauses 80 to 91, wherein the array of wells has a hydrophilic surface.

93. The method of any one of clauses 80 to 91, wherein the array of wells has a hydrophobic surface.

94. The method of any one of clauses 80 to 93, wherein the method is performed in an device comprising a first and second substrate and at least one substrate comprises a hydrophilic surface.

95. The method of any one of clauses 80 to 93, wherein the method is performed in an device comprising a first and second substrate and at least one substrate comprises a hydrophobic surface.

96. The method of any one of clauses 80 to 95, further comprising generating an electric actuation force with a plurality of electrodes to move the mixture to the array of wells to load the wells.

97. The method of any one of clauses 80 to 96, wherein one or more wells of the array are loaded with at least one detectable label.

98. The method of clause 97, further comprising removing any detectable labels that are not loaded into a well of the array after the loading.

99. The method of clause 98, wherein the removing comprises generating an electric actuation force with the plurality of electrodes to move a polarizable fluid droplet to the array of wells to move the at least a portion of the mixture to a distance from the array of wells.

100. The method of clause 99, wherein the removing comprises generating an electric actuation force with the plurality of electrodes to move an aqueous washing droplet across the array of wells.

101. The method of clause 100, wherein generating an electric actuation force comprises generating an alternating current.

102. The method of clause 101, wherein the alternating current has a root mean squared (rms) voltage of 10 V or more.

103. The method of any one of clauses 100 or 101, wherein the alternating current has a frequency in a radio frequency range.

104. The method of any one of the clauses 80 to 103, wherein the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

105. A method of measuring an analyte of interest in a liquid droplet, the method comprising:
(a) providing a first liquid droplet containing an analyte of interest;
(b) providing a second liquid droplet containing at least one solid support which contains a specific binding member that binds to the analyte of interest;
(c) using energy to exert a force to manipulate the first liquid droplet with the second liquid to create a mixture;
(d) moving all or at least a portion of the mixture to an array of wells, wherein one or more wells of the array is of sufficient size to accommodate the at least one solid support;
(e) adding a detectable label to the mixture either before or after moving a portion of the mixture to array of wells; and
(f) measuring the detectable label in the wells.

106. The method of clause 105, wherein the at least one solid support comprises at least one binding member that specifically binds to the analyte of interest.

107. The method of any one of clauses 105 or 106, further comprising adding a detectable label to the mixture before the moving at least a portion of the mixture to the array of wells.

108. The method of any one of clauses 105 or 106, further comprising adding a detectable label to the mixture after the moving at least a portion of the mixture to the array of wells 109. The method of any one of clauses 105 to 108, wherein the detectable label comprises at least one binding member that specifically binds to the analyte of interest.

110. The method of any one of clauses 105 to 109, wherein the detectable label comprises a chromagen, a fluorescent compound, an enzyme, a chemiluminescent compound or a radioactive compound.

111. The method of any one of clauses 105 to 109, wherein the binding member is a receptor or an antibody.

112. The method of any one of clauses 105 to 109, wherein the energy is an electric actuation force or acoustic force.

113. The method of clause 112, wherein the electric actuation force is droplet actuation, electrophoresis, electrowetting, dielectrophoresis, electrostatic actuation, electric field mediated, electrode mediated, capillary force, chromatography, centrifugation, or aspiration.

114. The method clause 112, wherein the acoustic force is surface acoustic wave.

115. The method of clauses 105 to 114, wherein the first liquid droplet is a polarizable liquid, the second liquid droplet is a polarizable liquid, the mixture is a polarizable liquid or both the first liquid droplet and second liquid droplet are each polarizable liquids.

116. The method of any one of clauses 105 to 112 and 115, further comprising manipulating the mixture over the array of wells using an electric actuation force.

117. The method of any one of clauses 105 to 116, further comprising manipulating the mixture over the array of wells using a capillary element configured to facilitate movement of the mixture to the array of wells.

118. The method of any one of clauses 105 to 117, wherein the solid supports are magnetic solid supports.

119. The method of clause 118, wherein an electric actuation force and the magnetic field are applied from opposite directions relative to the at least a portion of the mixture.

120. The method of any one of clauses 105 to 119, further comprising mixing the mixture by moving the mixture back and forth, moving the mixture in a circular pattern, splitting the mixture into two or more submixtures and merging the submixtures.

121. The method of any one of clauses 105 to 120, wherein the mixture is an aqueous liquid.

122. The method of any one of clauses 105 to 121, wherein the mixture is an immiscible liquid.

123. The method of any one of clauses 105 to 122, wherein the liquid droplet is a hydrophobic liquid droplet.

124. The method of any one of clauses 105 to 123, wherein the array of wells has a hydrophilic surface.

125. The method of any one of clauses 105 to 123, wherein the array of wells has a hydrophobic surface.

126. The method of any one of clauses 105 to 124, wherein the method is performed in an device comprising a first and second substrate and at least one substrate comprises a hydrophilic surface.

127. The method of any one of clauses 105 to 124, wherein the method is performed in an device comprising a first and second substrate and at least one substrate comprises a hydrophobic surface.

128. The method of any one of clauses 105 to 128, further comprising generating an electric actuation force with a plurality of electrodes to move the mixture to the array of wells to load the wells.

129. The method of any one of clauses 105 to 128, wherein one or more wells of the array are loaded with at least one solid support.

130. The method of clause 129, wherein the loading comprises applying a magnetic field to facilitate movement of at least one solid support into the one or more wells of the array.

131. The method of clause 130, further comprising removing any solid supports that are not loaded into a well of the array after the loading.

132. The method of clause 131, wherein the removing comprises generating an electric actuation force with the plurality of electrodes to move a polarizable fluid droplet to the array of wells to move the at least a portion of the mixture to a distance from the array of wells.

133. The method of clause 132, wherein the removing comprises generating an electric actuation force with the plurality of electrodes to move an aqueous washing droplet across the array of wells.

134. The method of clause 133, wherein generating an electric actuation force comprises generating an alternating current.

135. The method of clause 134, wherein the alternating current has a root mean squared (rms) voltage of 10 V or more.

136. The method of any one of clauses 134 or 135, wherein the alternating current has a frequency in a radio frequency range.

137. The method of any one of clauses 105 to 136, wherein the method is performed using a microfluidics device, digital microfluidics device (DMF), a surface acoustic wave based microfluidic device (SAW), an integrated DMF and analyte detection device, an integrated SAW and analyte detection device, or robotics based assay processing unit.

138. The method of any one of clauses 105 to 137, wherein the measuring involves determining the total number of solid supports in the wells of an array.

139. The method of clause 138, wherein the measuring involves determining the number of solid supports in the wells of the array that contain the detectable label.

140. The method of clause 139, wherein the measuring involves subtracting the number of solid supports that contain a detectable label from the total number of solid supports in the wells of the array to determine the number of solid supports in the wells of the array that do not contain any detectable label.

141. The method of clause 140, determining the ratio of solid supports that contain a detectable label to the number of solid supports that do not contain any detectable label.

142. A method of loading wells with particles, comprising:
  (a) generating an electric field with a plurality of electrodes to move a liquid droplet containing microparticles to an array of wells, wherein one or more wells of the array of wells is of sufficient size to have loaded therein a particle;
  (b) loading one or more wells with a particle; and
  (c) generating an electric field with the plurality of electrodes to move a polarizable fluid droplet to the array of wells to seal the array of wells.

143. The method of clause 142, further comprising manipulating liquid droplet over the array of wells using the electric field.

144. The method of any one of clauses 142 or 143, further comprising manipulating the liquid droplet over the array of wells using a capillary element configured to facilitate movement of the liquid droplet to the array of wells.

145. The method of any one of clauses 142 to 144, wherein the particle is a magnetic bead.

146. The method of clause 142, wherein the loading comprises applying a magnetic field to facilitate movement of the one or more magnetic beads into the one or more wells of the array.

147. The method of any one of clauses 142 to 146, wherein the array of wells has a hydrophilic surface.

148. The method of any one of clauses 142 to 146, wherein the array of wells has a hydrophobic surface.

149. The method of any one of clauses 142 to 148, wherein generating an electric field comprises generating an alternating current.

150. The method of clause 149, wherein the alternating current has a root mean squared (rms) voltage of 10 V or more.

151. The method of any of clauses 149 or 159, wherein the alternating current has a frequency in a radio frequency range.

152. A method of forming a digital microfluidic and analyte detection device, comprising:
  unwinding a first roll comprising a first substrate to position a first portion of the first substrate at a first position;
  forming a plurality of electrodes on the first portion of the first substrate at the first position; and
  forming an array of wells on a second portion of the first substrate at a second position.

153. The method of clause 152, further comprising:
  unwinding the first roll to position the second portion adjacent the first portion of the first substrate at the second position prior to forming the array of wells.

154. The method of clause 152 of clause 153, further comprising:
  unwinding a second roll comprising a second substrate to position a third portion of the third substrate at a third position; and
  bonding the second substrate with the first substrate at the third position in a manner sufficient to position the second substrate spaced apart from the first substrate.

155. A method of forming an integrated digital microfluidic and analyte detection device, comprising:
  unwinding a first roll comprising a first substrate to position a first portion of the first substrate at a first position;
  forming a plurality of electrodes on the first portion of the first substrate at the first position;
  unwinding a second roll comprising a second substrate to position a second portion of the second substrate at a second position;
  forming an array of wells on the second portion at the second position; and
  bonding the second substrate with the first substrate in a manner sufficient to:
    position the second substrate spaced apart from the first substrate; and
    position the second portion above the first portion, or above a third portion adjacent the first portion of the first substrate,
  wherein the array of wells faces the first substrate.

156. The method of any one of clauses 152 to 155, wherein the forming the array of wells comprises using thermal or ultraviolet nanoimprint lithography, nanoimprint roller, laser ablation, or by bonding a prefabricated substrate comprising an array of wells onto the first portion of the first substrate.

157. The method of any one of clauses 152 to 156, further comprising subjecting the first substrate to intense heat, pressure, or ultraviolet light to form phononic structures on or within the first substrate using a mold.

158. The method of any one of clauses 152 to 157, further comprising applying a hydrophobic and/or a dielectric material on electrodes of the series using a printer device.

159. The method of clause 158, wherein the hydrophobic and/or dielectric material comprises a curing material.

160. The method of clause 159, further comprising applying heat or ultraviolet light to cure the applied hydrophobic and/or dielectric material.

161. The method of any one of clauses 152 to 160, further comprising dicing the first and second substrates to generate a bonded substrates comprising the first and second portions.

162. A method of detecting an analyte of interest in a liquid droplet, the method comprising:
- (a) providing a first liquid droplet comprising an analyte of interest;
- (b) providing a second liquid droplet comprising a specific binding member and a labeled analyte, wherein the binding member is immobilized on at least one solid support, the specific binding member specifically binds to the analyte of interest, and the labeled analyte is an analyte of interest labeled with a detectable label;
- (c) using energy to exert a force to manipulate the first liquid droplet with the second liquid droplet to create a mixture; and
- (d) moving all or at least a portion of the mixture to an array of wells, wherein one or more wells of the array is of sufficient size to accommodate the at least one solid support;

163. A method of detecting an analyte of interest in a liquid droplet, the method comprising:
- (a) providing a first liquid droplet comprising an analyte of interest;
- (b) providing a second liquid droplet comprising an immobilized analyte and at least one specific binding member, wherein the immobilized analyte is an analyte of interest immobilized on at least one solid support, the at least one specific binding member specifically binds to the analyte of interest, and the at least one specific binding member is labeled with a detectable label;
- (c) using energy to exert a force to manipulate the first liquid droplet with the second liquid droplet to create a mixture;
- (d) moving all or at least a portion of the mixture to an array of wells, wherein one or more wells of the array is of sufficient size to accommodate the at least one solid support; and (e) detecting the analyte of interest in the wells.

164. A method of detecting an analyte of interest in a liquid droplet, the method comprising:
- (a) providing a first liquid droplet containing an analyte of interest;
- (b) providing a second liquid droplet containing at least one solid support which contains a specific binding member that binds to the analyte of interest;
- wherein the first and second liquid droplets are provided into a digital microfluidic and analyte detection device, comprising:
  - a first substrate and a second substrate, wherein the second substrate is separated from the first substrate by a gap, the first substrate comprising a plurality of electrodes to generate electrical actuation forces on a liquid droplet; and
  - an array of wells dimensioned to hold a portion of the liquid droplet, wherein at least a portion of the array of wells is positioned between one or more of the plurality of electrodes and the gap;
- (c) using the electrical actuation forces to manipulate the first liquid droplet with the second liquid droplet to create a mixture;
- (d) moving all or at least a portion of the mixture to the array of wells, wherein one or more wells of the array is of sufficient size to accommodate the at least one solid support;
- (e) adding a detectable label to the mixture either before or after moving a portion of the mixture to array of wells; and
- (f) detecting the analyte of interest in the wells.

165. The method of clause 164, wherein the at least one solid support comprises at least one binding member that specifically binds to the analyte of interest.

166. The method of any one of clauses 164 or 165, further comprising adding a detectable label to the mixture before the moving at least a portion of the mixture to the array of wells.

167. The method of any one of clauses 164 or 166, further comprising adding a detectable label to the mixture after the moving at least a portion of the mixture to the array of wells.

168. The method of any one of clauses 164 to 167, wherein the detectable label comprises at least one binding member that specifically binds to the analyte of interest.

169. The method of any one of clauses 164 to 168, wherein the detectable label comprises a chromagen, a fluorescent compound, an enzyme, a chemiluminescent compound or a radioactive compound.

170. The method of any one of clauses 164 to 168, wherein the binding member is a receptor or an antibody.

171. The method of any one of clauses 164 to 170, wherein the electric actuation forces are droplet actuation, electrophoresis, electrowetting, dielectrophoresis, electrostatic actuation, electric field mediated, electrode mediated, capillary force, chromatography, centrifugation, or aspiration.

172. The method of any one of clauses 164 to 171, wherein the first liquid droplet is a polarizable liquid, the second liquid droplet is a polarizable liquid, the mixture is a polarizable liquid or both the first liquid droplet and second liquid droplet are each polarizable liquids.

173. The method of any one of clauses 164 to 171, further comprising manipulating the mixture over the array of wells using an electric actuation force.

174. The method of any one of clauses 164 to 173, further comprising manipulating the mixture over the array of wells using a capillary element configured to facilitate movement of the mixture to the array of wells.

175. The method of any one of clauses 164 to 174, wherein the solid supports are magnetic solid supports.

176. The method of clause 175, wherein the electric actuation forces and the magnetic field are applied from opposite directions relative to the at least a portion of the mixture.

177. The method of any one of clauses 164 to 176, further comprising mixing the mixture by moving the mixture back and forth, moving the mixture in a circular pattern, splitting the mixture into two or more submixtures and merging the submixtures.

178. The method of any one of clauses 164 to 176, wherein the mixture is an aqueous liquid.

179. The method of any one of clauses 164 to 176, wherein the mixture is an immiscible liquid.

180. The method of any one of clauses 164 to 179, wherein the liquid droplet is a hydrophobic liquid droplet.

181. The method of any one of clauses 164 to 180, wherein the array of wells has a hydrophilic surface.

182. The method of any one of clauses 164 to 180, wherein the array of wells has a hydrophobic surface.

183. The method of any one of clauses 164 to 182, wherein the substrate comprises a hydrophilic surface.

184. The method of any one of clauses 164 to 182, wherein the substrate comprises a hydrophobic surface.

185. The method of any one of clauses 164 to 184, further comprising generating an electric actuation force with a plurality of electrodes to move the mixture to the array of wells totol load the wells.

186. The method of any one of clauses 164 to 185, wherein one or more wells of the array are loaded with at least one solid support.

187. The method of clause 186, wherein the loading comprises applying a magnetic field to facilitate movement of at least one solid support into the one or more wells of the array.

188. The method of clause 187, further comprising removing any solid supports that are not loaded into a well of the array after the loading.

189. The method of clause 188, wherein the removing comprises generating an electric actuation force with the plurality of electrodes to move a polarizable fluid droplet to the array of wells to move the at least a portion of the mixture to a distance from the array of wells.

190. The method of clause 189, wherein the removing comprises generating an electric actuation force with the electrodes to move an aqueous washing droplet across the array of wells.

191. The method of clause 190, wherein generating an electric actuation force comprises generating an alternating current.

192. The method of clause 191, wherein the alternating current has a root mean squared (rms) voltage of 10 V or more.

193. The method of any one of clauses 191 or 192, wherein the alternating current has a frequency in a radio frequency range.

194. A method of detecting an analyte of interest in a liquid droplet, the method comprising:
  (a) providing a first liquid droplet containing an analyte of interest;
  (b) providing a second liquid droplet containing at least one solid support which contains a specific binding member that binds to the analyte of interest;
  wherein the first and second liquid droplets are provided into a surface acoustic wave microfluidic and analyte detection device, comprising:
    a first substrate and a second substrate, wherein the second substrate is separated from the first substrate by a gap, wherein the device comprises a first portion and a second portion,
    the first portion comprising a superstrate coupled to a surface acoustic wave generating component; and
    the second portion comprising a plurality of wells positioned on the first substrate or the second substrate,
  (c) using surface acoustic forces to manipulate the first liquid droplet with the second liquid droplet to create a mixture;
  (d) moving all or at least a portion of the mixture to the array of wells, wherein one or more wells of the array is of sufficient size to accommodate the at least one solid support;
  (e) adding a detectable label to the mixture either before or after moving a portion of the mixture to array of wells; and
  (f) detecting the analyte of interest in the wells.

195. The method of clause 194, wherein the at least one solid support comprises at least one binding member that specifically binds to the analyte of interest.

196. The method of any one of clauses 194 or 195, further comprising adding a detectable label to the mixture before the moving at least a portion of the mixture to the array of wells.

197. The method of any one of clauses 194 or 196, further comprising adding a detectable label to the mixture after the moving at least a portion of the mixture to the array of wells.

198. The method of any one of clauses 194 to 197, wherein the detectable label comprises at least one binding member that specifically binds to the analyte of interest.

199. The method of any one of clauses 194 to 198, wherein the detectable label comprises a chromagen, a fluorescent compound, an enzyme, a chemiluminescent compound or a radioactive compound.

200. The method of any one of clauses 194 to 199, wherein the binding member is a receptor or an antibody.

201. The method of any one of clauses 194 to 200, wherein the first liquid droplet is a polarizable liquid, the second liquid droplet is a polarizable liquid, the mixture is a polarizable liquid or both the first liquid droplet and second liquid droplet are each polarizable liquids.

202. The method of any one of clauses 194 to 201, further comprising manipulating the mixture over the array of wells using a capillary element configured to facilitate movement of the mixture to the array of wells.

203. The method of any one of clauses 194 to 202, wherein the solid supports are magnetic solid supports.

204. The method of clause 70, wherein the method further comprises sealing the array of wells with a hydrophobic liquid.

205. The method of clause 96, wherein the method further comprises sealing the array of wells with a hydrophobic liquid.

206. The method of clause 185, wherein the method further comprises sealing the array of wells with a hydrophobic liquid.

The invention claimed is:

1. A digital microfluidic and analyte detection device, comprising:
  a first substrate and a second substrate aligned to define a gap therebetween, the first substrate comprising a plurality of electrodes to generate electrical actuation forces on a liquid droplet disposed in the gap;
  at least one reagent disposed in a printed or dried form on at least one of the first substrate and the second substrate and configured to be carried by the liquid droplet upon contact with the liquid droplet, wherein the liquid droplet with the at least one reagent further comprises at least one solid support and an analyte of interest; and
  an array of elements, each element dimensioned to hold a single one of the at least one solid support or the at least one analyte of interest, wherein each element of the array of elements comprises a first sidewall and a bottom surface, and wherein at least a top portion of the first sidewall is oriented at an obtuse angle with reference to the bottom surface.

2. The device of claim 1, wherein each element comprises a well.

3. The device of claim 2, wherein the first substrate comprises a first portion at which the liquid droplet is introduced and a second portion toward which a liquid droplet is moved, wherein the array is disposed proximate the second portion.

4. The device of claim 2, wherein at least one of the first and second substrates is substantially transparent to facilitate optical interrogation of the wells.

5. The device of claim 1, wherein the reagent is selected from the group consisting of a detectable label, a binding member, a dye, a surfactant, and a combination thereof.

6. The device of claim 5, wherein the detectable label comprises at least one binding member that specifically binds to the analyte of interest.

7. The device of claim 5, wherein the detectable label comprises a chromagen, a fluorescent compound, an enzyme, a chemiluminescent compound, or a radioactive compound.

8. The device of claim 5, wherein the binding member comprises a receptor or an antibody.

9. The device of claim 2, further comprising a first layer disposed on the surface of the first substrate and extending over the plurality of electrodes and a second layer disposed on a surface of the first layer, wherein the first layer is a dielectric layer and the second layer is a hydrophobic layer.

10. The device of claim 9, wherein each well is positioned in the second layer.

11. The device of claim 1, wherein a bottom portion of the first sidewall is oriented at the obtuse angle with reference to the bottom surface.

12. The device of claim 1, wherein each element of the array of elements comprises a second sidewall that is perpendicular to the bottom surface.

13. The device of claim 1, wherein each element of the array of elements comprises a second sidewall that is oriented at an acute angle with reference to the bottom portion.

14. A method of detecting an analyte of interest in a liquid droplet, comprising:
introducing a liquid droplet containing an analyte of interest into a device comprising:
a first substrate and a second substrate aligned to define a gap therebetween, the first substrate comprising a plurality of electrodes to generate electrical actuation forces on the liquid droplet when disposed in the gap;
at least one reagent disposed in a printed or dried form on at least one of the first substrate and the second substrate and configured to be carried by the liquid droplet upon contact with the liquid droplet, wherein the liquid droplet with the at least one reagent further comprises at least one solid support; and
an array of elements, each element dimensioned to hold at least a portion of the liquid droplet in a discrete region, wherein each element of the array of elements comprises a first sidewall and a bottom surface, and wherein at least a top portion of the first sidewall is oriented at an obtuse angle with reference to the bottom surface;
using an electrical actuation force to move the liquid droplet towards the array;
labeling the analyte of interest with a detectable label; and
detecting the analyte of interest in the array.

15. The method of claim 14, wherein the liquid droplet is a mixture comprising a first liquid including the analyte of interest and a second liquid including the at least one solid support,
the method further comprising mixing the mixture by moving the mixture back and forth, moving the mixture in a circular pattern, splitting the mixture into two or more submixtures and merging the submixtures.

16. The method of claim 14, wherein the electric actuation force is droplet actuation, electrophoresis, electrowetting, dielectrophoresis, electrostatic actuation, electric field mediated, or electrode mediated.

17. The method of claim 14, wherein the elements comprise wells, and the method further comprises sealing at least one of the wells within the array with a hydrophobic liquid.

18. The method of claim 14, further comprising measuring the analyte of interest, wherein the measuring comprises:
identifying solid supports in the array that contain the detectable label; and
calculating a ratio of the solid supports containing the detectable label to solid supports without the detectable label.

19. The device of claim 2, wherein the plurality of electrodes generates electrical actuation forces on a wash droplet disposed in the gap to wash the solid supports to remove molecules not bound to the solid supports.

20. The device of claim 19, wherein the plurality of electrodes generates electrical actuation forces on the wash droplet to move the wash droplet across the array of wells.

* * * * *